US008853437B2

(12) United States Patent
Arita et al.

(10) Patent No.: US 8,853,437 B2
(45) Date of Patent: Oct. 7, 2014

(54) ANTI-INFLAMMATORY COMPOUNDS

(75) Inventors: Makoto Arita, Tokyo (JP); Hiroyuki Arai, Tokyo (JP); Yousuke Isobe, Tokyo (JP); Ryo Taguchi, Tokyo (JP)

(73) Assignee: The University of Tokyo, Tokyo (JP)

( * ) Notice: Subject to any disclaimer, the term of this patent is extended or adjusted under 35 U.S.C. 154(b) by 368 days.

(21) Appl. No.: 13/202,489

(22) PCT Filed: Feb. 19, 2010

(86) PCT No.: PCT/JP2010/052509
§ 371 (c)(1),
(2), (4) Date: Aug. 19, 2011

(87) PCT Pub. No.: WO2010/095706
PCT Pub. Date: Aug. 26, 2010

(65) Prior Publication Data
US 2012/0059061 A1      Mar. 8, 2012

(30) Foreign Application Priority Data

Feb. 20, 2009  (JP) ................................. 2009-037939

(51) Int. Cl.
| C07C 59/42 | (2006.01) |
| C07C 233/09 | (2006.01) |
| A61K 31/16 | (2006.01) |
| A61K 31/11 | (2006.01) |
| C07C 291/00 | (2006.01) |
| C12P 7/64 | (2006.01) |

(52) U.S. Cl.
CPC ............... *C07C 59/42* (2013.01); *C12P 7/6436* (2013.01); *C12P 7/6427* (2013.01)
USPC ............. 554/213; 554/35; 554/219; 554/224; 554/227; 514/599; 514/703; 558/299; 560/222

(58) Field of Classification Search
CPC ....................................................... C07C 59/42
See application file for complete search history.

(56) References Cited

U.S. PATENT DOCUMENTS

| 6,670,396 B2 | 12/2003 | Serhan et al. |
| 7,030,159 B2 | 4/2006 | Serhan et al. |
| 2006/0241088 A1 | 10/2006 | Arterburn et al. |
| 2009/0318394 A1 | 12/2009 | Nauroth et al. |

FOREIGN PATENT DOCUMENTS

| WO | 01 60778 | 8/2001 |
| WO | 03 053423 | 7/2003 |
| WO | 2004 014835 | 2/2004 |
| WO | 2005 089744 | 9/2005 |

(Continued)

OTHER PUBLICATIONS

International Search Report Issued Apr. 27, 2010 in PCT/JP10/052509 filed Feb. 19, 2010.

(Continued)

*Primary Examiner* — Yate K Cutliff
(74) *Attorney, Agent, or Firm* — Oblon, Spivak, McClelland, Maier & Neustadt, L.L.P.

(57) ABSTRACT

An object of the present invention is to provide a compound having a novel structure for overcoming the defects of conventional steroid agents and NSAIDs. It is found that the particular dihydroxy bodies of eicosapentaenoic acid and docosahexaenoic acid, which have not conventionally been known (11,18-dihydroxy eicosapentaenoic acid (11,18-di-HEPE), 17,18-dihydroxy eicosapentaenoic acid (17,18-di-HEPE) etc.), have activity of inhibiting neutrophil, thereby solving the object. The present invention unexpectedly remarkably inhibits infiltration into a tissue of, and activation of neutrophil found out at acute inflammation. The compound of the present invention is a compound which has not conventionally been known. Therefore, utility as a new therapeutic is provided.

14 Claims, 31 Drawing Sheets

(56) References Cited

FOREIGN PATENT DOCUMENTS

| WO | 2006 055965 | 5/2006 |
|---|---|---|
| WO | 2006 078457 | 7/2006 |
| WO | 2006 105058 | 10/2006 |
| WO | 2007 127377 | 11/2007 |
| WO | 2008 011085 | 1/2008 |
| WO | 2008 057283 | 5/2008 |
| WO | 2008 070129 | 6/2008 |
| WO | 2008 103753 | 8/2008 |
| WO | 2009 038671 | 3/2009 |
| WO | 2009 051670 | 4/2009 |

OTHER PUBLICATIONS

Extended European Search Report issued Jul. 10, 2013 in Patent Application No. 10743831.9.

Ernst H. Oliw, et al., "Metabolism of polyunsaturated (n-3) fatty acids by monkey seminal vesicles: isolation and biosynthesis of omega-3 epoxides", Biochimica et Biophysica Acta, vol. 1086, No. 3, XP27222690A, 1991, pp. 287-294.

M. Takenaga, et al., "Comparison of the In Vitro Effect of Eicosapentaenoic Acid (EPA)—Derived Lipoxygenase Metabolites on Human Platelet Function with those of Arachidonic Acid", Thrombosis Research, vol. 41, No. 3, XP26360661A, 1986, pp. 373-384.

A. J. Hampson, et al., "Biosynthesis of eicosanoids by blood cells of the crab, *Carcinus maenas*", Biochimica et Biophysica Acta, vol. 1124, XP2699600A, 1992, pp. 143-150.

T. H. Lee, et al., "Characterization and biological properties of 5,12-dihydroxy derivatives of eicosapentaenoic acid, including leukotriene B5 and the double lipoxygenase product", Journal of Biological Chemistry, vol. 259, XP2699601A, 1984, pp. 2383-2389 with cover pages.

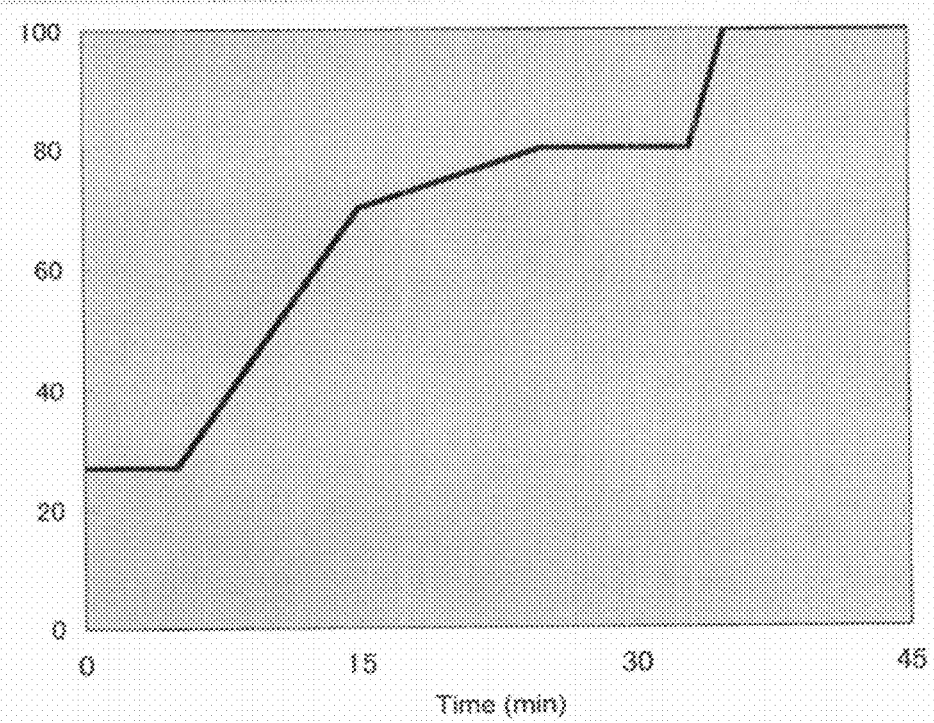

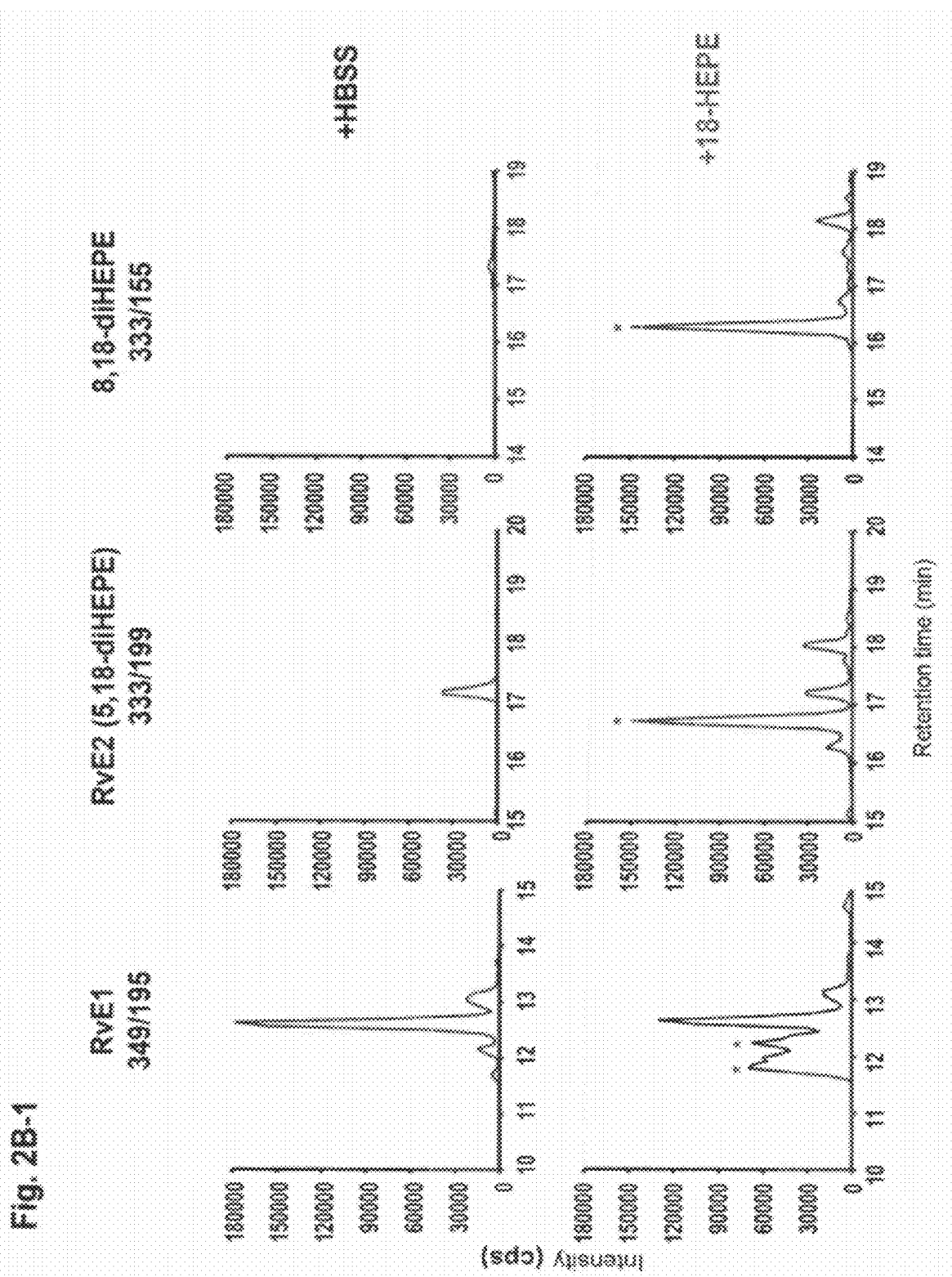

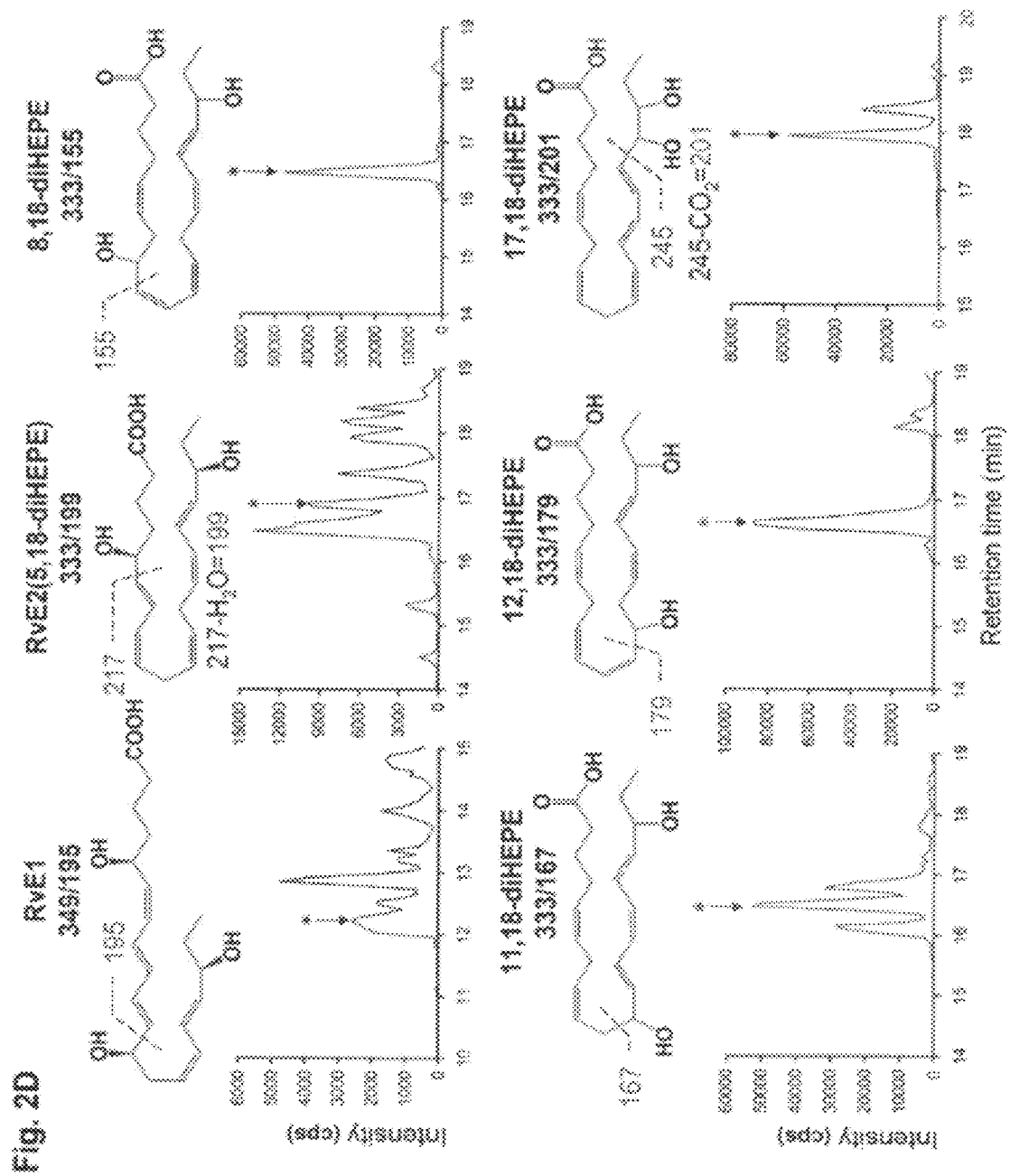

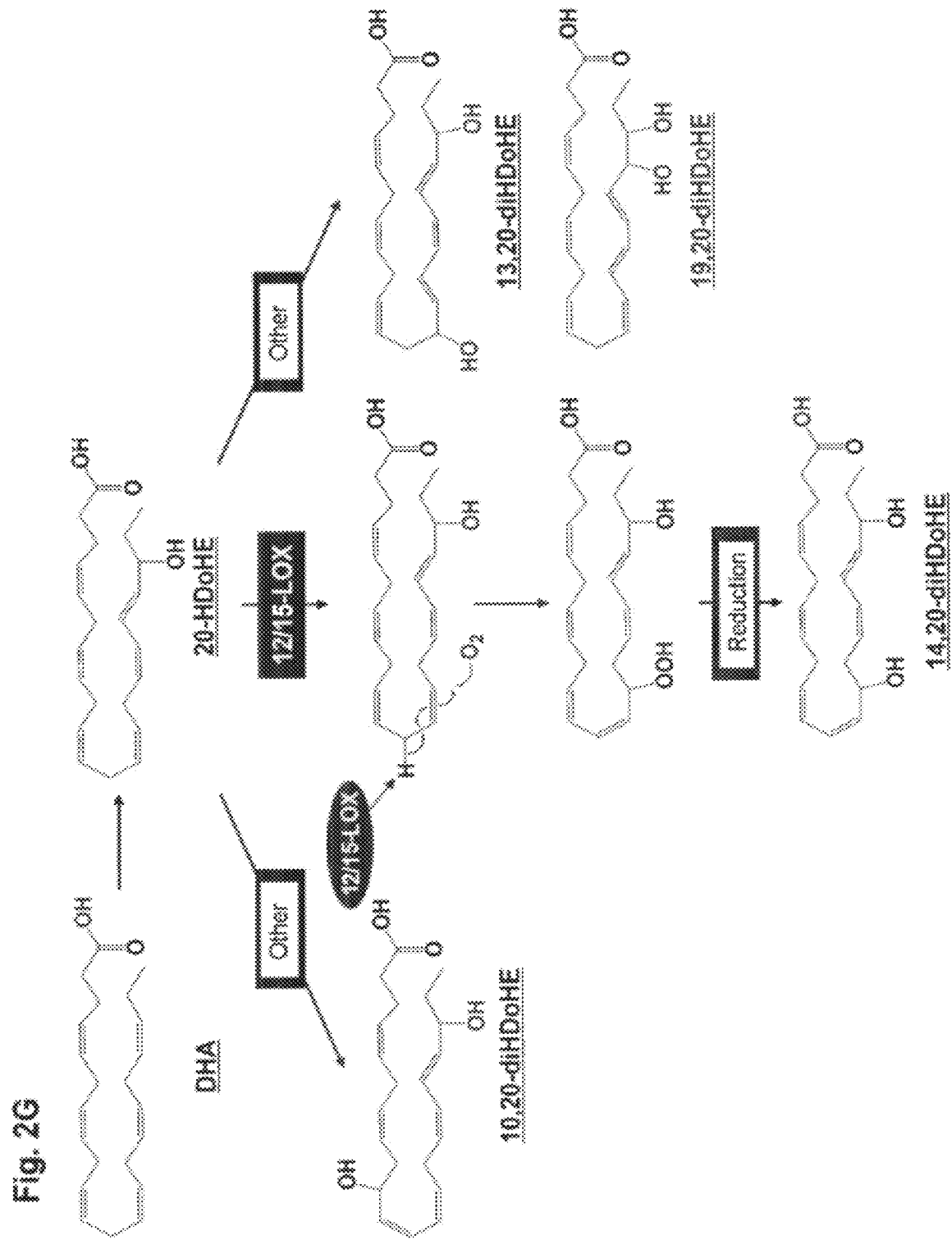

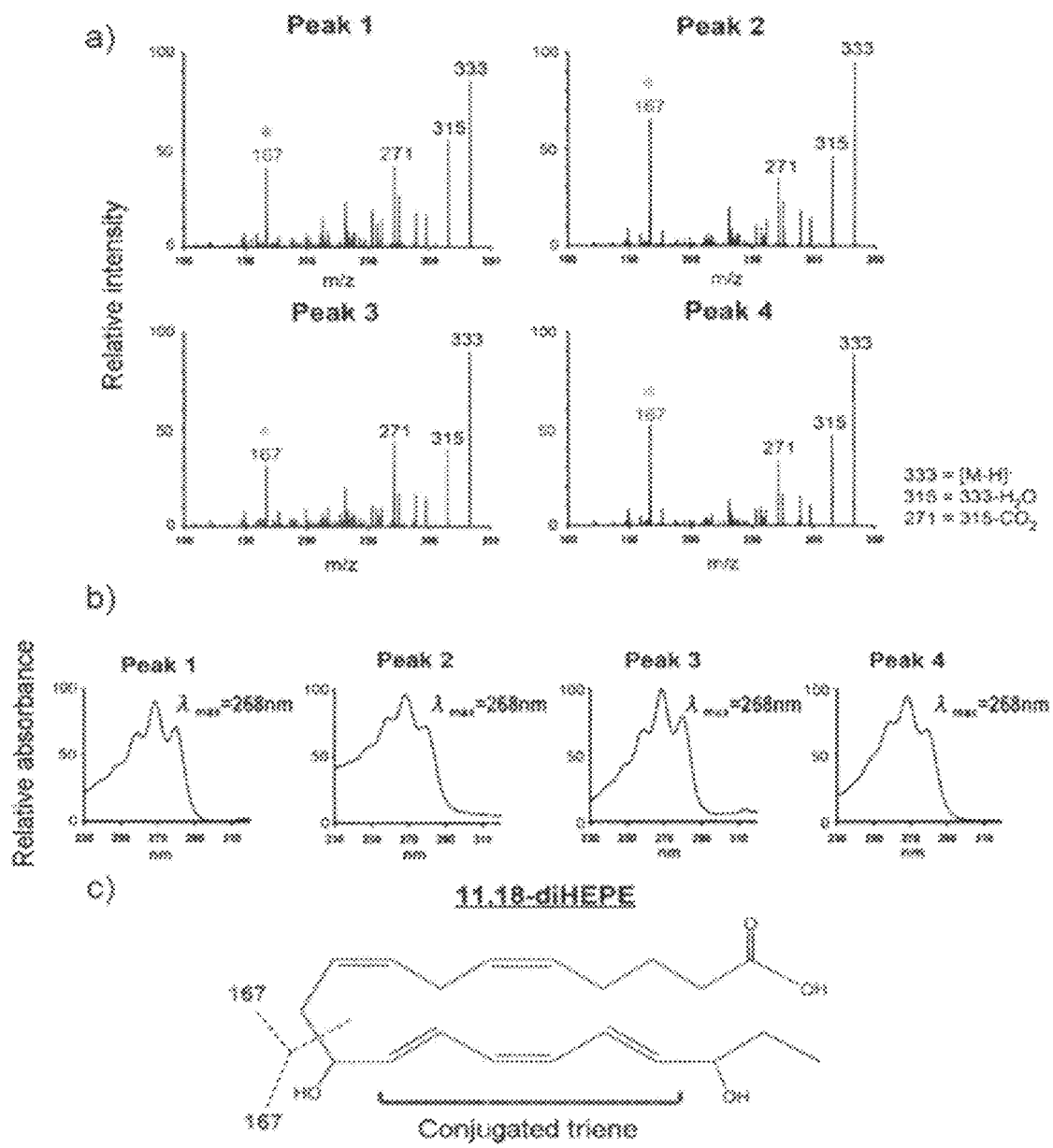

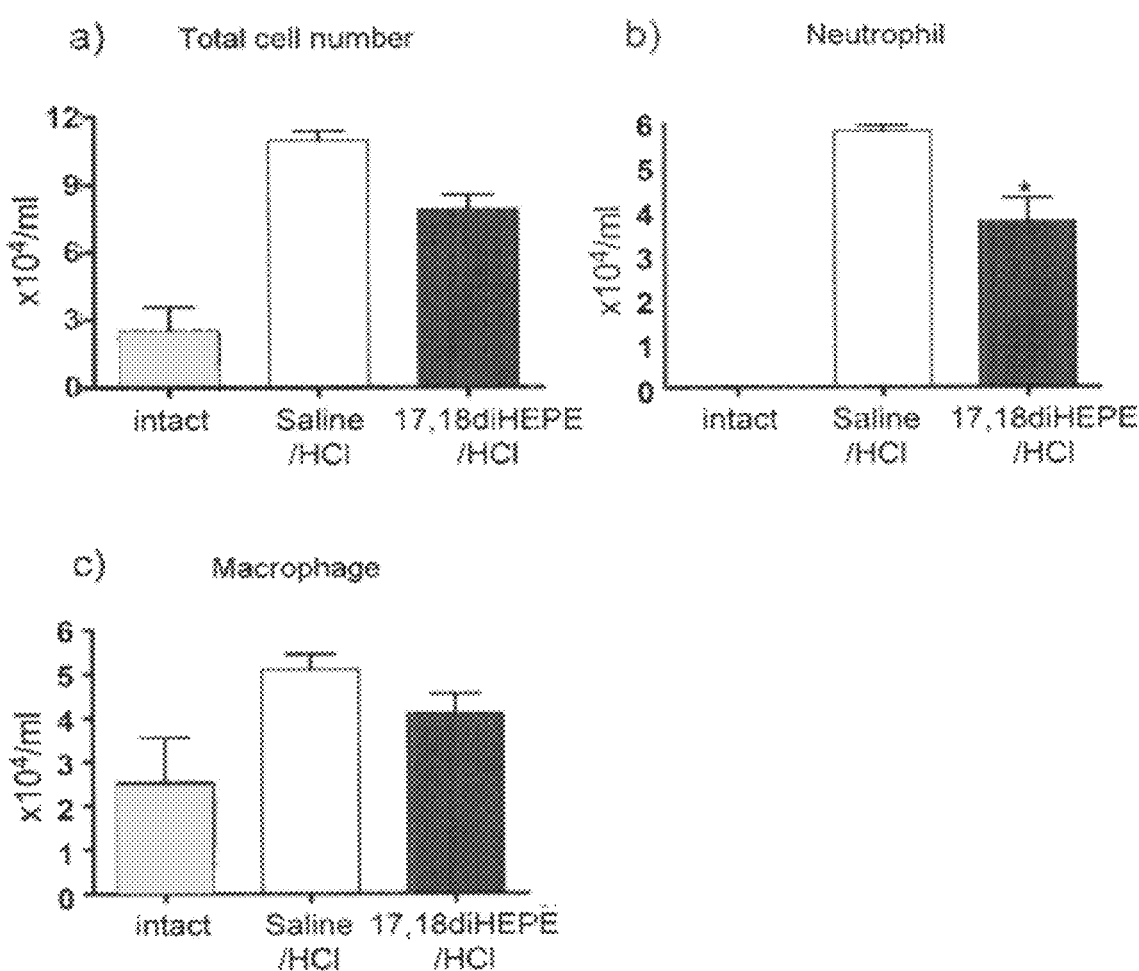

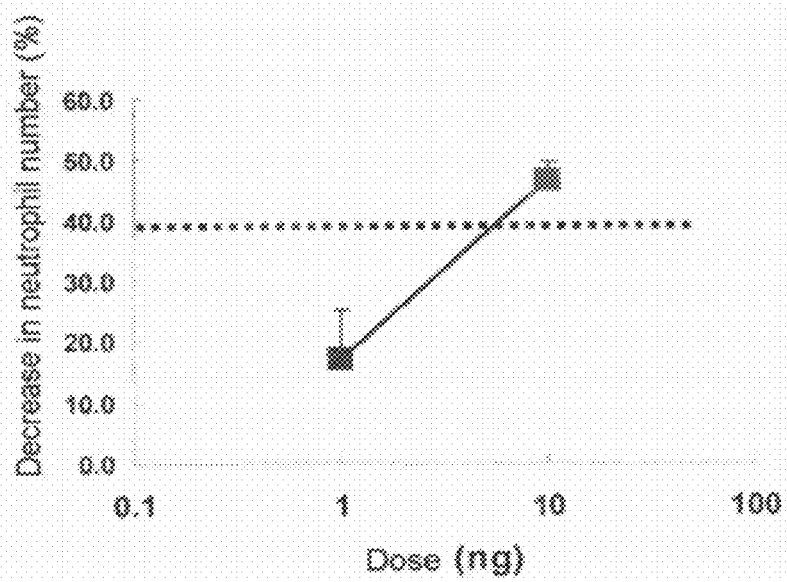

Fig. 5
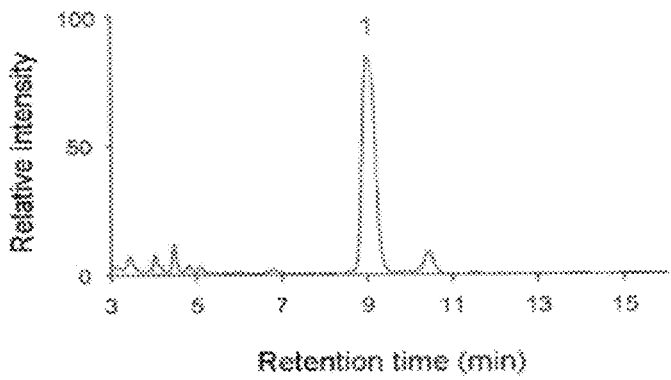
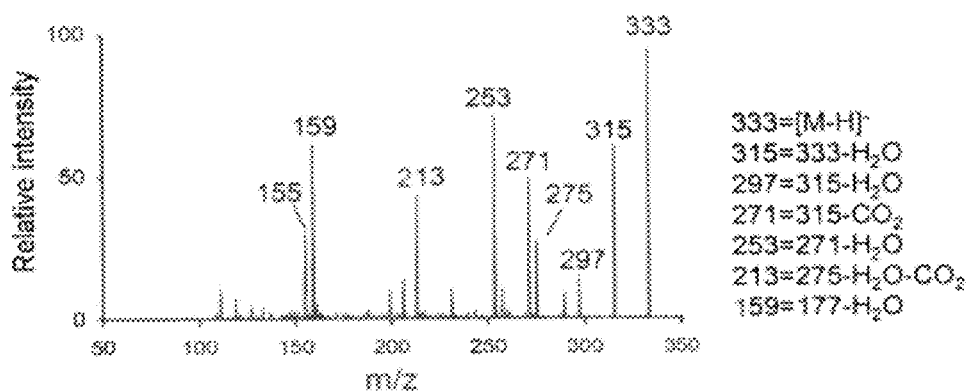
8,18-diHEPE
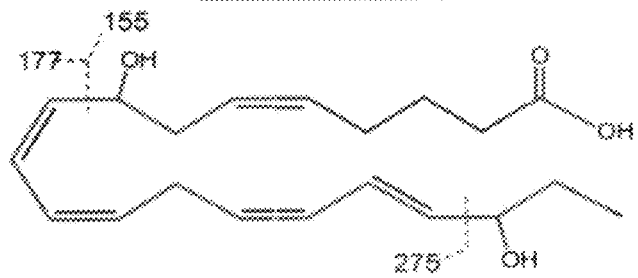

Fig. 6
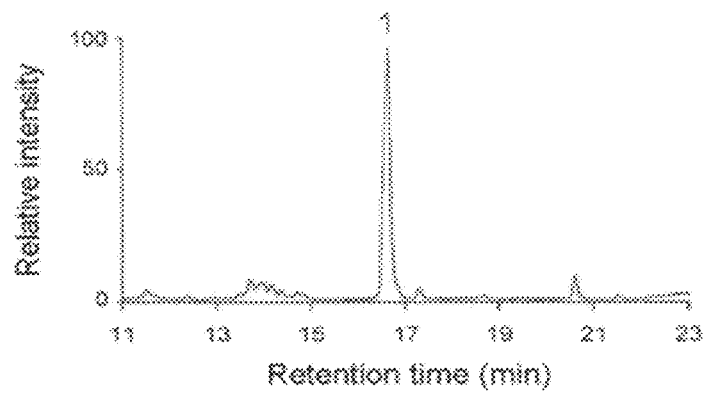
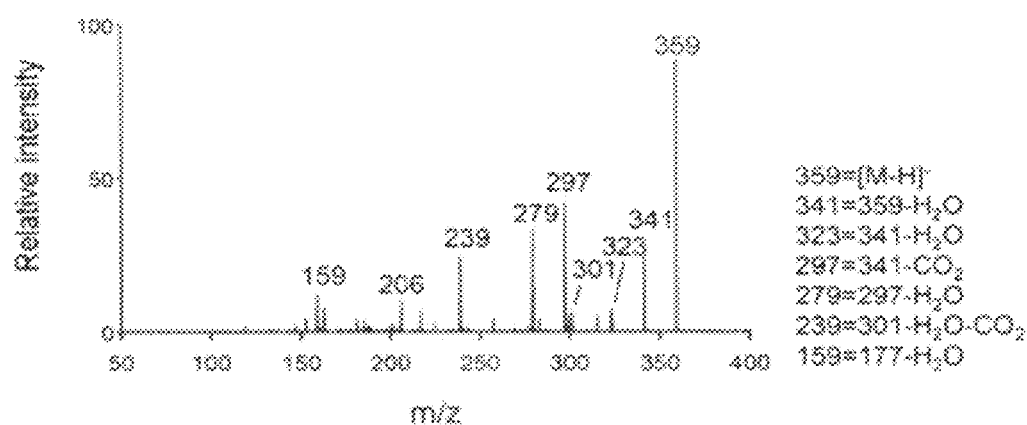
10,20-diHDoHE
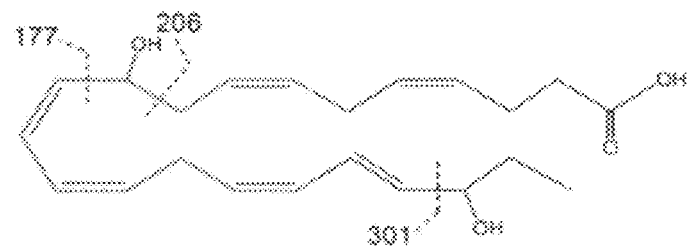

Fig. 8
A
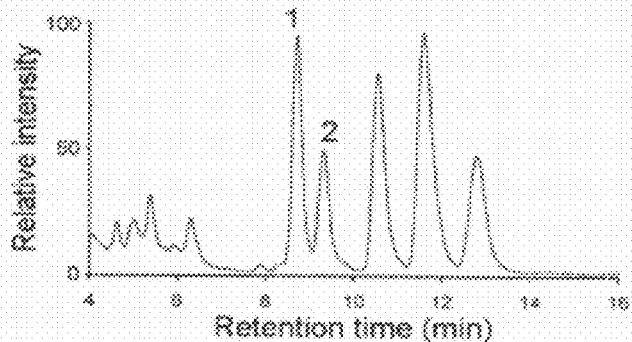
B
Peak 1
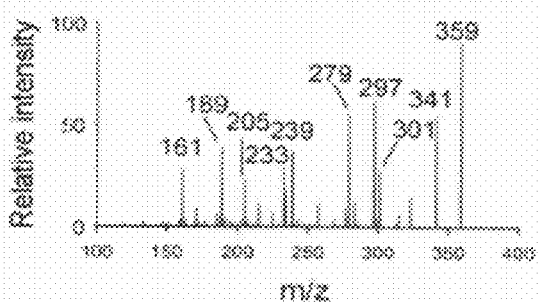
Peak 2
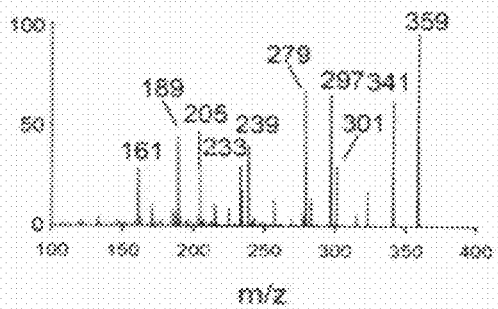
239=301-$H_2O$-$CO_2$
189=233-$CO_2$
161=189-$H_2O$
14,20-diHDoHE
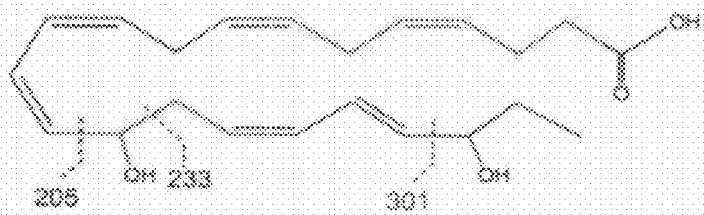

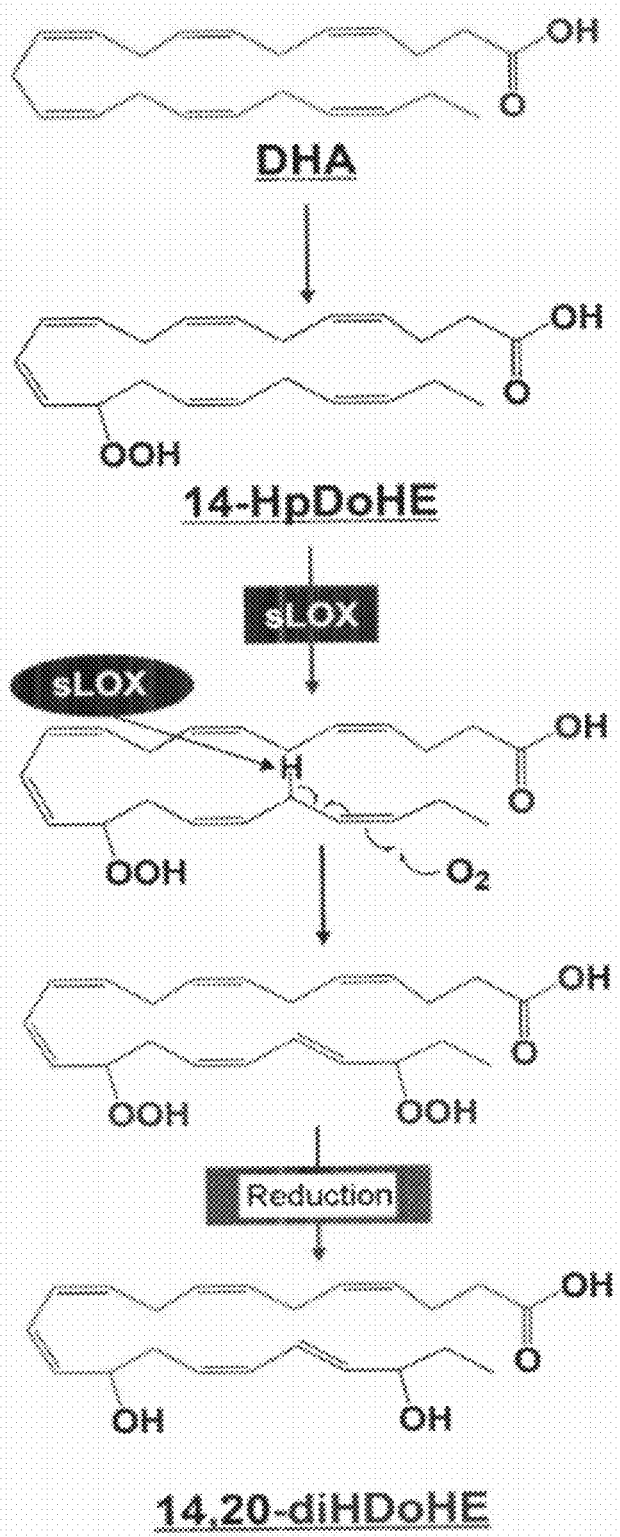

ANTI-INFLAMMATORY COMPOUNDS

This application is a National Stage of PCT/JP10/052509 filed Feb. 19, 2010 and claims the benefit of JP 2009-037939 filed Feb. 20, 2009.

TECHNICAL FIELD

The present invention relates to a novel anti-inflammatory compound.

BACKGROUND ART

An inflammatory disease, in a modern era, is one of the important disease fields for which countermeasure is necessary and, as a modern anti-inflammatory drug, representatively, substances such as a steroid agent, and aspirin and ibuprofen called non-steroid anti-inflammatory drugs (NSAIDS) are used.

However, among these substances, since the steroid agent has a high effect, it is used as a therapeutic for any of acute and chronic inflammatory diseases in the clinical site, but a problem such as acquisition of resistance due to frequent use, a side effect etc. has been pointed out.

Since NSAIDS have an antipyretic analgesic action, it has been used as symptomatic therapy, but it has also been known that in NSAIDS, due to ingestion for a long term, a disorder is generated in a digestive tract, a cardiac disease risk is increased, and progression of inflammatory tissue damage occurs, and this has become a serious problem (Non-Patent Documents 1 and 2).

In addition, it has been known that a substance having hydroxyl groups at the 18-position and the 5-position of eicosapentaenoic acid (EPA) called Resolvin such as Resolvin E1 (RvE1; 5S,12R,18R-trihydroxyeicosapentaenoic acid), and a derivative thereof, and a substance having hydroxyl groups at the 10-position and the 17-position of docosahexaenoic acid (DHA) called Protectin D1, and a derivative thereof have an anti-inflammatory activity (Non-Patent Documents 3 and 4).

PRIOR ART DOCUMENTS

Non-Patent Documents

Non-Patent Document 1: Singh G. Am. J. Med. 105, 31S-38S (1998)
Non-Patent Document 2: Funk C. D. and FitzGerald G. A. J. Cardiovasc Pharmacol 50, 470-479 (2007)
Non-Patent Document 3: Serhan C. N. et al. Prostaglandins and other Lipid Mediators 73, 155-172 (2004)
Non-Patent Document 4: E. Tjonahen et al., Chemistry & Biology 13, 1193-1202, November 2006

SUMMARY OF THE INVENTION

Problems to be Solved by the Invention

An object of the present invention is to provide a compound having a novel structure for overcoming the aforementioned defects of conventional steroid agents and NSAIDs.

Means for Solving the Problems

As a result of intensive study, the present inventors have found that particular dihydroxy bodies of eicosapentaenoic acid and docosahexaenoic acid (8,18-dihydroxyeicosapentaenoic acid (8,18-diHEPE), 11,18-dihydroxyeicosapentaenoic acid (11,18-diHEPE), 12,18-dihydroxyeicosapentaenoic acid (12,18-diHEPE), 17,18-dihydroxyeicosapentaenoic acid (17,18-diHEPE), 10,20-dihydroxydocosahexaenoic acid (10,20-diHDoHE), 14,20-dihydroxydocosahexaenoic acid (14,20-diHDoHE), 19,20-dihydroxydocosahexaenoic acid (19,20-diHDoHE) etc.), which have not been conventionally known unlike Resolvin/Protectin, have a neutrophil suppression activity, and have achieved the aforementioned object.

Therefore, the present invention provides the followings:
(1) A compound selected from 8,18-dihydroxyeicosapentaenoic acids (8,18-diHEPE)

[Chemical Formula 1]

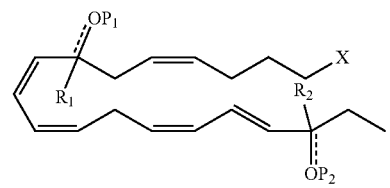

11,18-dihydroxyeicosapentaenoic acids (11,18-diHEPE)

[Chemical Formula 2]

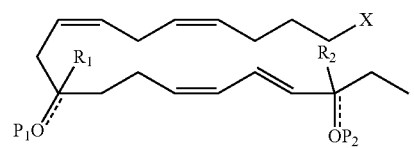

12,18-dihydroxyeicosapentaenoic acids (12,18-diHEPE)

[Chemical Formula 3]

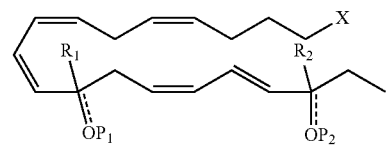

17,18-dihydroxyeicosapentaenoic acids (17,18-diHEPE)

[Chemical Formula 4]

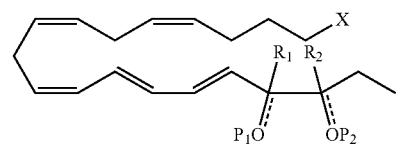

10,20-dihydroxydocosahexaenoic acids (10,20-diHDoHE)

[Chemical Formula 5]

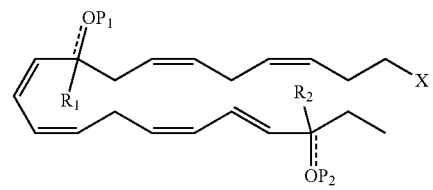

13,20-dihydroxydocosahexaenoic acids (13,20-diHDoHE)

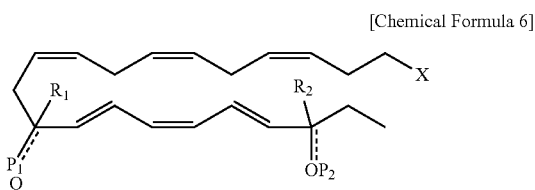

[Chemical Formula 6]

14,20-dihydroxydocosahexaenoic acids (14,20-diHDoHE)

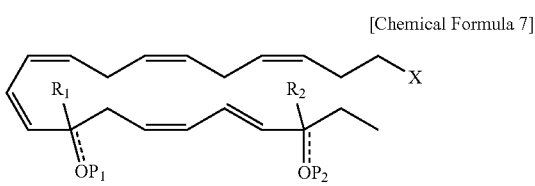

[Chemical Formula 7]

and 19,20-dihydroxydocosahexaenoic acids (19,20-diHDoHE)

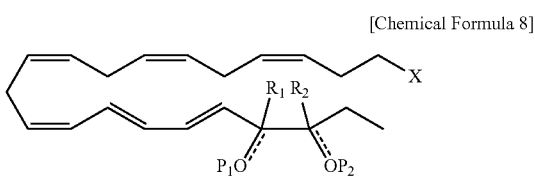

[Chemical Formula 8]

or a pharmaceutically acceptable salt or solvate thereof, wherein $P_1$ and $P_2$ are each independently a protective group, a hydrogen atom, alkyl, a hydroxyl group or a substituted hydroxyl group or a combination thereof, when ≈≈≈≈≈ [Chemical Formula 9]

indicates a single bond, $P_1$, $P_2$, $R_1$ and $R_2$ are not present, when

───── [Chemical Formula 10]

indicates a double bond, and when

≈≈≈≈≈ [Chemical Formula 11]

is a single bond, $R_1$ and $R_2$ are each independently a hydrogen atom, a halogen atom, a substituted or unsubstituted branched or non-branched alkyl group, a substituted or unsubstituted aryl group, a substituted or unsubstituted branched or non-branched alkylaryl group or a combination thereof;

X is —C(O)OR$_3$, —C(O)NR$_4$R$_5$, —C(O)H, —C(NH)NR$_4$R$_5$, —C(S)H, —C(S)OR$_3$, —C(S)NR$_4$R$_5$, or —CN;

$R_3$ is hydrogen, a protective group, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle or a group of the formula: —NR$_a$R$_b$ (wherein R$_a$ and R$_b$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or R$_a$ and R$_b$ may be taken together with an adjacent nitrogen atom to form a substituted or unsubstituted nitrogen-containing heterocyclic ring);

$R_4$ and $R_5$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocycle, or $R_4$ and $R_5$ may be taken together with an adjacent nitrogen atom to form a substituted or unsubstituted nitrogen-containing heterocyclic ring; and double bond configurations of the compound can be each independently any of cis or trans.

(2) The compound or pharmaceutically acceptable salt or solvate according to Item 1, wherein the compound is selected from the group consisting of the followings: 8,18-dihydroxyeicosapentaenoic acid (8,18-diHEPE)

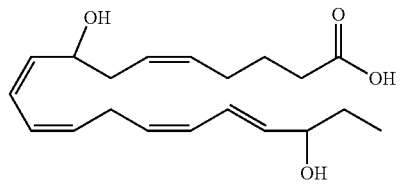

[Chemical Formula 12]

11,18-dihydroxyeicosapentaenoic acid (11,18-diHEPE)

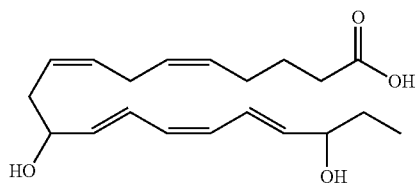

[Chemical Formula 13]

12,18-dihydroxyeicosapentaenoic acid (12,18-diHEPE)

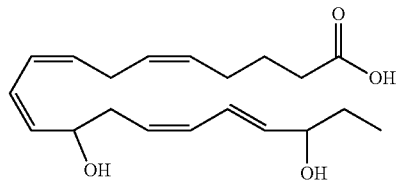

[Chemical Formula 14]

17,18-dihydroxyeicosapentaenoic acid (17,18-diHEPE)

[Chemical Formula 15]

10,20-dihydroxydocosahexaenoic acid (10,20-diHDoHE)

[Chemical Formula 16]

13,20-dihydroxydocosahexaenoic acid (13,20-diHDoHE)

[Chemical Formula 17]

14,20-dihydroxydocosahexaenoic acid (14,20-diHDoHE)

[Chemical Formula 18]

and 19,20-dihydroxydocosahexaenoic acid (19,20-diHDoHE)

[Chemical Formula 19]

(3) A neutrophil suppressing agent comprising the compound or pharmaceutically acceptable salt or solvate according to Item 1 or 2.
(4) A pharmaceutical comprising the compound or pharmaceutically acceptable salt or solvate according to Item 1 or 2.
(5) The pharmaceutical according to Item 4, wherein the pharmaceutical is used for treating or preventing a disease, a disorder or a state which is improved by suppressing neutrophil selected from pulmonary diseases selected from pulmonary distress syndrome, adult respiratory distress syndrome, and chronic obstructive pulmonary disease (COPD); ischemic diseases selected from ischemic cardiac disease, ischemic renal disease, ischemic brain disease and ischemic hepatic disease; inflammatory diseases; stress related diseases selected from erosive gastritis, gastric ulcer, duodenal ulcer, bronchial asthma, ulcerative colitis, arteriosclerosis, Crohn disease, malignant tumor, ovarian cyst, salpingitis, hysteromyoma, endometriosis, spontaneous abortion, gestosis, infertility and dysmenorrhea.
(6) A method of producing the compound or pharmaceutically acceptable salt or solvate according to Item 1 or 2, comprising the steps of:
A) contacting eicosapentaenoic acid (EPA), docosahexaenoic acid (DHA), 18-hydroxyl eicosapentaenoic acid (HEPE) or 20-hydroxyl docosahexaenoic acid (HDoHE) with at least one selected from the group consisting of 8-lipoxygenase (8-LOX), 12-lipoxygenase (12-LOX), 12/15-lipoxygenase (12/15-LOX), soybean lipoxygenase (sLOX) and eosinophil or an extract thereof to obtain an enzyme metabolite; and
B) reducing or oxidizing the enzyme metabolite as necessary, introducing a substituent as necessary, and separating or purifying the objective compound or a pharmaceutically acceptable salt or solvate thereof as necessary.
(7) A method of producing the compound or pharmaceutically acceptable salt or solvate according to Item 1 or 2, comprising the steps of:
A) contacting eicosapentaenoic acid (EPA), docosahexaenoic acid (DHA), 18-hydroxyl eicosapentaenoic acid (HEPE) or 20-hydroxyl docosahexaenoic acid (HDoHE) with at least one selected from the group consisting of 8-lipoxygenase (8-LOX), 12-lipoxygenase (12-LOX), 12/15-lipoxygenase (12/15-LOX), soybean lipoxygenase (sLOX) and eosinophil or an extract thereof to obtain an enzyme metabolite;
B) contacting the enzyme metabolite obtained in A) step, after purification or without purification, with at least one selected from the group consisting of 8-lipoxygenase (8-LOX), 12-lipoxygenase (12-LOX), 12/15-lipoxygenase (12/15-LOX), soybean lipoxygenase (sLOX) and eosinophil or an extract thereof to obtain a secondary enzyme metabolite; and
C) reducing or oxidizing the secondary enzyme metabolite as necessary, introducing a substituent as necessary, and separating or purifying the objective compound or a pharmaceutically acceptable salt or solvate thereof as necessary.
(8) The method according to Item 7, further comprising the step of repeating B) step and C) step as necessary.
(9) A method of treating or preventing an inflammatory disease, comprising the step of administering the compound or pharmaceutically acceptable salt or solvate according to Item 1 or 2 to a subject in need of the treatment or the prevention.
(10) Use of the compound or pharmaceutically acceptable salt or solvate according to Item 1 or 2 for producing a medicament.
(11) Use of the compound or pharmaceutically acceptable salt or solvate according to Item 1 or 2 for producing a medicament for treating or preventing a disease, a disorder or a state associated with neutrophil.
(12) A method of analyzing the compound according to Item 1 or 2 or a PUFA metabolite, comprising employing the following liquid chromatography conditions:
using A liquid: water/acetic acid=100/0.1, and B liquid: acetonitrile/methanol=4/1 as a solvent system, using a flow rate: 0 to 30 minutes→50 µL/minute, 30 to 33 minutes→80 µL/minute, 33 to 45 minutes→100 µL/minute, using a gradient described in FIG. 1B or a altered system thereof as a gradient, and using parameters described in FIG. 1C.

(13) A product produced by a method comprising the steps of:

A) contacting eicosapentaenoic acid (EPA), docosahexaenoic acid (DHA), 18-hydroxyl eicosapentaenoic acid (HEPE) or 20-hydroxyl docosahexaenoic acid (HDoHE) with at least one selected from the group consisting of 8-lipoxygenase (8-LOX), 12-lipoxygenase (12-LOX), 12/15-lipoxygenase (12/15-LOX), soybean lipoxygenase (sLOX) and eosinophil or an extract thereof to obtain an enzyme metabolite; and B) reducing or oxidizing the enzyme metabolite as necessary, introducing a substituent as necessary, and separating or purifying the objective compound or a pharmaceutically acceptable salt or solvate thereof as necessary, provided that Resolvin E1, Resolvin E2 and Protectin D1 are excluded.

In setting of the aforementioned conditions, regarding synthesized compounds (e.g., compounds synthesized with an enzyme; 11,18-diHEPE and 17,18-diHEPE correspond thereto), a pair of a parent mass and a child mass of MRM can be optimized (optimization of collision energy) from measured values of MS/MS. In addition, when a calibration curve is produced, quantitative analysis becomes possible. Regarding not synthesized compounds, MRM for the purpose of detection is performed by setting hypothetical conditions.

In these all aspects, it is understood that respective embodiments described in the present specification can be applied in other aspects as far as they are applicable.

A plurality of embodiments are disclosed, however, still other embodiments of the present invention will become apparent to a person skilled in the art from the following detailed description. As is apparent, the present invention can be modified in a variety of evident aspects without departing from the technical idea and the scope of the present invention. Therefore, the drawings and the detailed description are deemed to be illustrative actually, and are not deemed to be restrictive.

Advantages of the Invention

The present invention unexpectedly remarkably suppresses infiltration into tissues and activation of neutrophil found at the time of acute inflammation. The compound of the present invention is a compound which has not been conventionally known. Therefore, utility as a new therapeutic is provided.

In addition, since it has been found in the present invention that the compound of the present invention is also found in a living body, the compound of the present invention is expected to be a therapeutic having little side effect in administration for a medium and long term. In addition, since the compound of the present invention is different from steroid agents and NSAIDs in its action, the compound of the present invention is expected to have an effect as an anti-inflammatory agent by joint use with the existing steroid agents, etc.

BRIEF DESCRIPTION OF THE DRAWINGS

FIG. 1B shows an example of a solvent gradient used in MRM of the present invention.

FIG. 2A-2 shows incubation of peritoneal exudate cells (PEC) at an inflammation early stage (after 4 hours) with 18-hydroxy eicosapentaenoic acid (HEPE). An asterisk indicates a peak of a metabolite including respective isomers. From the left side, an asterisk indicates 11,18-diHEPE, 12,18-diHEPE and 17,18-diHEPE in this order.

FIG. 2B-1 shows incubation of PEC at an inflammation later stage (after 48 hours) with 18-HEPE. An asterisk indicates a peak of a metabolite including respective isomers. From the left side, an asterisk indicates Resolvin E1, Resolvin E2, and 8,18-diHEPE in this order.

FIG. 2B-2 shows incubation of PEC at an inflammation later stage (after 48 hours) with 18-HEPE. An asterisk indicates a peak of a metabolite including respective isomers. From the left side, an asterisk indicates 11,18-diHEPE, 12,18-diHEPE and 17,18-diHEPE.

FIG. 2D shows the analysis results of each metabolite generated as the result of incubation of 18-HEPE with eosinophil. An asterisk indicates a peak of each main metabolite. From the left upper side to the right upper side, an asterisk indicates Resolvin E1, Resolvin E2, and 8,18-diHEPE in this order and, from the left lower side to the right lower side, an asterisk indicates 11,18-diHEPE, 12,18-diHEPE and 17,18-diHEPE in this order.

FIG. 2G shows a metabolism route using 20-HDoHE which is a metabolite of docosahexaenoic acid (DHA) as an origin. In addition, experimentally, 10,20-diHDoHE can be synthesized using 8-LOX.

FIG. 3B shows (a) mass spectroscopy (MS/MS) and (b) light absorption spectrum of peaks 1 to 4 of Example 3, and (c) structure of 11,18-diHEPE.

FIG. 4B shows assessment of physiological activity of an 18-HEPE-derived metabolite (17,18-diHEPE) in an acute lung damage model. From the left side, the total number of cells (a), the number of neutrophil (b) and the number of macrophage (c) which have infiltrated into lung at the time point of 12 hours after non-treatment (intact), intrabronchial hydrochloric acid administration (saline/HCl), and intrabronchial hydrochloric acid administration after tail vein administration of 10 ng of 17,18-diHEPE (17,18diHEPE/HCl) are shown. The average of 3 or more times experiments is taken, respectively, and the value is shown as an average±SEM. * represents p<0.05 for saline/HCl.

FIG. 4F is a graph showing a relationship of dose-decrease in the neutrophil number for studying a dose of $IC_{40}$.

FIG. 5 shows (A) reverse phase HPLC chromatogram of a sample obtained by incubation of 18-HEPE with 8-LOX, and (B) mass spectroscopy (MS/MS) of peak 1 and the structure of 8,18-diHEPE.

FIG. 6 shows (A) reverse phase HPLC chromatogram of a sample obtained by incubation of 20-HDoHE with 8-LOX, and (B) mass spectroscopy (MS/MS) of a peak 1 and the structure of 10,20-diHDoHE.

FIG. 8 shows (A) reverse phase HPLC chromatogram of a sample obtained by incubation of 14-HpEPE with sLOX, and (B) mass spectroscopy (MS/MS) of peak 1 and the structure of 14,20-diHDoHE.

FIG. 9B shows a metabolism route using 14-HpDoHE which is a metabolite of docosahexaenoic acid (DHA) as an origin.

MODE FOR CARRYING OUT THE INVENTION

Figure 1A:
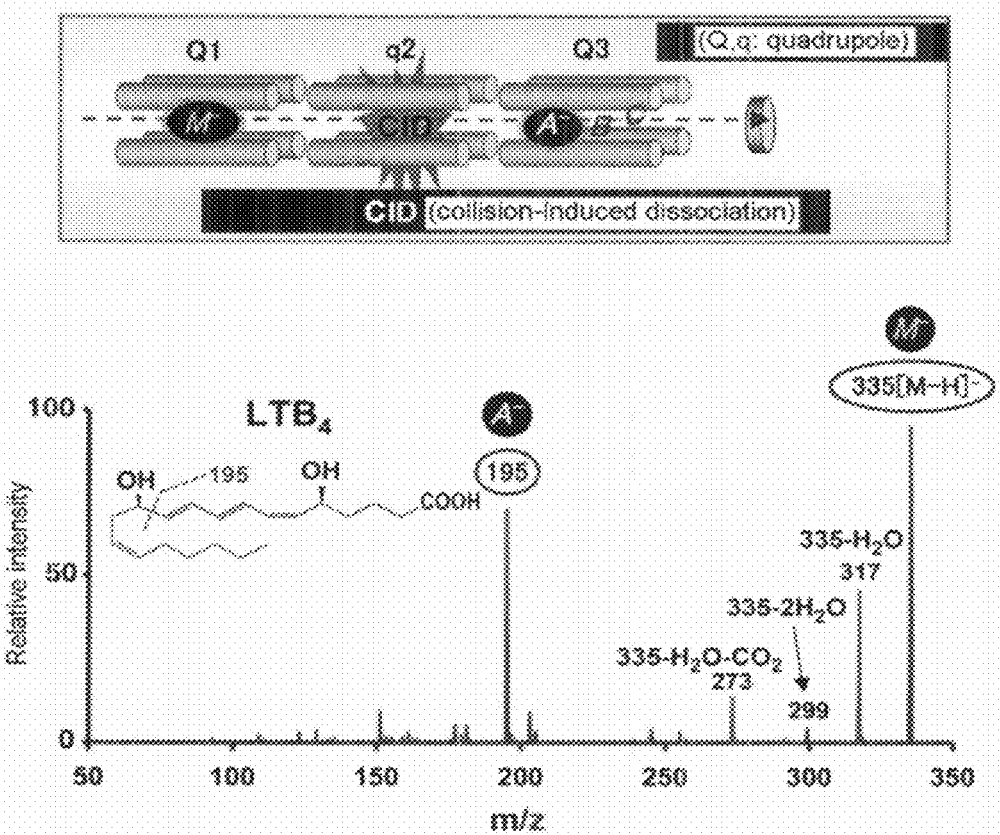
FIG. 1A is a view showing the principle of multiple reaction monitoring (MRM). The figure below shows an example of measurement with $LTB_4$. $M^-$ indicates a parent mass value, and $A^-$ indicates a child mass value.

The present invention will be described below. It should be understood that expression of a singular form also includes concept of a plural form thereof unless otherwise is indicated, throughout the present specification. Therefore, it should be understood that an article in a singular form (e.g., "a", "an", "the" etc. in the case of English) also includes concept of a plural form thereof unless otherwise is indicated. In addition, it should be understood that the terms used in the present specification are used in the meaning usually used in the art unless otherwise is indicated. Therefore, unless defined elsewhere, all the terminology and the scientific and technical terms used in the present specification have the same meanings as those that are generally understood by a person skilled in the art to which the present invention pertains. In the case of contradiction, the present specification (including definitions) prevails.

(Definition of Terms)

In the present specification, the following abbreviations are used as necessary.

AA: arachidonic acid
CCR: chemokine (C—C motif)-receptor
COX: cyclooxygenase
DHA: docosahexaenoic acid
DPA: docosapentaenoic acid
EET: epoxy eicosatrienoic acid
Ep: epoxy
EpDPE: epoxy docosapentaenoic acid
EpETE: epoxy eicosatetraenoic acid
EPA: eicosapentaenoic acid
ETE: eicosatetraenoic acid HESS: Hanks' balanced salt solution
HDoHE: hydroxy docosahexaenoic acid
HEPE: hydroxy eicosapentaenoic acid
HETE: hydroxy eicosatetraenoic acid
HpDoHE: hydroperoxy docosapentaenoic acid
HpEPE: hydroperoxy eicosapentaenoic acid
LC: liquid chromatography
LOX: lipoxygenase
LT: leukotriene
LX: lipoxin
MRM: multiple reaction monitoring
N: normal
PBS: phosphate buffered saline
PEC: peritoneal exudate cells
PD1: protectin D1
PG: prostaglandin
ppt.: pellet
PUFA: polyunsaturated fatty acid
Rv: resolvin
sLOX: soybean lipoxygenase
Tg: transgenic
HPLC: ultra performance liquid chromatography
(Terms)

The meaning of each term used in the present specification will be described below. Each term is used in a unified meaning in the present specification, and is used in the same meaning when used alone, and when used in combination with other terms.

In the present specification, "halogen" means fluorine, chlorine, bromine and iodine. Fluorine, chlorine, and bromine are preferable.

In the present specification, "alkyl" refers to a saturated or unsaturated, branched, straight or cyclic monovalent hydrocarbon group having carbon atoms in the referred number (that is, C1-C6 means 1 to 6 carbon atoms), which is derived by removing one hydrogen atom from a single carbon atom of a parent alkane, as itself, or as a part of other substituents. Representatively, the alkyl includes a straight or branched monovalent hydrocarbon group having 1 to 8 carbon atoms. Examples thereof include methyl, ethyl, n-propyl, isopropyl, n-butyl, isobutyl, sec-butyl, tert-butyl, n-pentyl, isopentyl, neo-pentyl, n-hexyl, isohexyl, n-heptyl, and n-octyl. Preferable examples thereof include C1-C6 alkyl. Further preferable examples thereof include C1-C4 alkyl. Particularly, when the carbon number is designated, the alkyl means "alkyl" having carbon atoms in a range of the number.

In the present specification, "alkenyl" refers to an unsaturated and branched, straight, or cyclic hydrocarbon group, having at least one carbon-carbon double bond, which is derived by removing one hydrogen atom from a single carbon atom of a parent alkene, as itself, or as a part of other substituents. Representatively, the alkenyl includes a straight or branched monovalent hydrocarbon group having 2 to 8 carbon atoms, and having one or two or more double bonds. The group may have either of cis configuration or trans configuration regarding a double bond. Examples thereof include vinyl, allyl, 1-propenyl, 2-butenyl, 2-pentenyl, 2-hexenyl, 2-heptenyl, and 2-octenyl. Preferable examples thereof include C2-C6 alkenyl. Further preferable examples thereof include C2-C4 alkenyl.

In the present specification, "alkynyl" includes a straight or branched monovalent hydrocarbon group having 2 to 8 carbon atoms and having one or two or more triple bonds. Examples thereof include ethynyl, 1-propynyl, 2-propynyl, 2-butynyl, 2-pentynyl, 2-hexynyl, 2-heptynyl, and 2-octynyl. Preferable examples thereof include C2-C6 alkynyl. Further preferable examples thereof include C2-C4 alkynyl.

In the present specification, "diyl" of alkyl, alkenyl or alkynyl refers to a saturated or unsaturated, branched, straight or cyclic divalent hydrocarbon group having carbon atoms in the referred number (that is, C1-C6 means 1 to 6 carbon atoms), which is derived by removing one hydrogen atom from each of two different carbon atoms of parent alkane, alkene or alkyne, or removing two hydrogen atoms from a single carbon atom of parent alkane, alkene or alkyne, as itself, or as a part of other substituents. A bond can be formed with atoms, in which each valence of a center of two monovalent groups or a center of a divalent group is the same or different. Typical Examples of the diyl group include, but are not limited to, the followings: methanediyl; ethyldiyls such as ethane-1,1-diyl, ethane-1,2-diyl, ethene-1,1-diyl, or ethene-1,2-diyl; propyldiyl such as propane-1,1-diyl, propane-1,2-diyl, propane-2,2-diyl, propane-1,3-diyl, cyclopropane-1,1-diyl, cyclopropane-1,2-diyl, prop-1-ene-1,1-diyl, prop-1-ene-1,2-diyl, prop-2-ene-1,2-diyl, prop-1-ene-1,3-diyl, cycloprop-1-ene-1,2-diyl, cycloprop-2-ene-1,2-diyl, cycloprop-2-ene-1,1-diyl, and prop-1-yne-1,3-diyl; butyldiyls such as butane-1,1-diyl, butane-1,2-diyl, butane-1,3-diyl, butane-1,4-diyl, butane-2,2-diyl, 2-methyl-propane-1,1-diyl, 2-methyl-propane-1,2-diyl, cyclobutane-1,1-diyl; cyclobutane-1,2-diyl, cyclobutane-1,3-diyl, but-1-ene-1,1-diyl, but-1-ene-1,2-diyl, but-1-ene-1,3-diyl, but-1-ene-1,4-diyl, 2-methyl-prop-1-ene-1,1-diyl, 2-methanylidene-propene-1,1-diyl, buta-1,3-diene-1,1-diyl, buta-1,3-diene-1,2-diyl, buta-1,3-diene-1,3-diyl, buta-1,3-diene-1,4-diyl, cyclobut-1-ene-1,2-diyl, cyclobut-1-ene-1,3-diyl, cyclobut-2-ene-1,2-diyl, cyclobuta-1,3-diene-1,2-diyl, cyclobuta-1,3-diene-1,3-diyl, but-1-yne-1,3-diyl, but-1-yne-1,4-diyl, and buta-1,3-diyne-1,4-diyl; etc. When saturation at a particular level is intended, nomenclature alkyldiyl, alkenyldiyl and/or alkynyldiyl is used. When it is particularly intended that two valences are on the same carbon atom, nomenclature "alkylidene" is used. In a preferable embodiment, an alkyldiyl group is (C1-C6) alkyldiyl. A saturated non-cyclic alkanyldiyl group in which a center of group is on carbon at an end, for example, methanediyl (methano); ethane-1,2-diyl (ethano); propane-1,3-diyl (propano); butane-1,4-diyl (butano); etc. are also preferable (also referred to as "alkyleno").

In the present specification, "cycloalkyl" refers to an unsaturated and branched, straight or cyclic hydrocarbon group having at least one carbon-carbon triple bond, which is derived by removing one hydrogen atom from a single carbon atom of parent alkene, as itself, or as a part of other substituents. Representatively, cycloalkyl includes cycloalkyl having 3 to 8 carbon atoms. Examples thereof include cyclopropyl, cyclobutyl, cyclopentyl, cyclohexyl, cycloheptyl, and cyclooctyl. Preferable examples thereof include C3-C6 cycloalkyl.

In the present specification, "cycloalkenyl" includes cycloalkenyl having 3 to 8 carbon atoms. Examples thereof include cyclopropenyl, cyclobutenyl, cyclopentenyl, cyclohexenyl, and cycloheptenyl, and preferable examples thereof include C3-C6 cycloalkenyl.

In the present specification, examples of "alkoxy" include methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, and n-octyloxy. Preferable examples thereof include C1-C6 alkyloxy. Further preferable examples thereof include C1-C4 alkyloxy. Particularly, when the carbon number is designated, the alkoxy means "alkoxy" having carbon atoms in a range of the number.

In the present specification, examples of "alkylsulfonyl" include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, and n-octylsulfonyl. Preferable examples thereof include C1-C6 alkylsulfonyl. Further preferable examples thereof include C1-C4 alkylsulfonyl.

In the present specification, examples of "alkyloxycarbonyl" include methyloxycarbonyl, ethyloxycarbonyl, n-propyloxycarbonyl, isopropyloxycarbonyl, n-butyloxycarbonyl, tert-butyloxycarbonyl, and n-pentyloxycarbonyl. Preferable examples thereof include C1-C4 alkyloxycarbonyl. Particularly preferable examples thereof include C1-C2 alkyloxycarbonyl.

In the present specification, "acyl" includes formyl, alkylcarbonyl, alkenylcarbonyl, cycloalkylcarbonyl, cycloalkenylcarbonyl, arylcarbonyl, heteroarylcarbonyl, and heterocyclecarbonyl. Examples thereof include acetyl, propionyl, butyroyl, and benzoyl.

In the present specification, "lower alkyl" includes straight or branched alkyl having 1 to 6 carbon atoms, and preferably 1 to 3 carbon atoms, and examples thereof include methyl, ethyl, n-propyl, isopropyl, n-butyl, isobutyl, sec-butyl, tert-butyl, n-pentyl, isopentyl, neopentyl, hexyl, and isohexyl.

The lower alkyl part of "lower alkoxy", "hydroxy lower alkyl", "hydroxy lower alkoxy", "lower alkoxycarbonyl", "lower alkylamino", "lower alkoxy lower alkoxy", "lower alkylcarbamoyl", "hydroxy lower alkylcarbamoyl", "lower alkoxyimino", "lower alkylthio", "lower alkylsulfonyl", "lower alkylsulfonyloxy", "lower alkylsulfamoyl", and "lower alkylsulfinyl" is also the same as the above "lower alkyl".

In the present specification, "substituted or unsubstituted lower alkyl" may be substituted, and may be preferably substituted with one or more groups selected from a substituent group α.

Herein, the substituent group α is a group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, imino, hydroxyimino, lower alkoxyimino, lower alkylthio, carbamoyl, lower alkylcarbamoyl, hydroxy lower alkylcarbamoyl, sulfamoyl, lower alkylsulfamoyl, lower alkylsulfinyl, cyano, nitro, a carbocyclic group and a heterocyclic group.

In the present specification, "lower alkenyl" includes a straight or branched alkenyl having 2 to 15 carbon atoms, preferably 2 to 10 carbon atoms, more preferably 2 to 6 carbon atoms, and further preferably 2 to 4 carbon atoms, and having one or more double bonds at an arbitrary position. Specific examples thereof include vinyl, aryl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

In the present specification, "lower alkynyl" includes a straight or branched alkynyl having 2 to 10 carbon atoms, preferably 2 to 8 carbon atoms, and further preferably 3 to 6 carbon atoms, and having one or more triple bonds at an arbitrary position. Specific examples thereof include ethynyl, propynyl, butynyl, pentynyl, hexynyl, heptynyl, octynyl, nonynyl, and decynyl. These may further have a double bond at an arbitrary position.

In the present specification, "carbocyclic group" includes cycloalkyl, cycloalkenyl, aryl, and non-aromatic condensed carbocyclic group, etc.

In the present specification, "substituted or unsubstituted amino" includes amino which may be substituted at one or two positions with the "alkyl" described above, the "aryl" described later, the "heteroaryl" described later, the "heterocycle" described later, the "acyl" described above, the "alkyloxycarbonyl" described above, the "alkylsulfonyl" described above, the "arylsulfonyl" described later, the "heteroarylsulfonyl" described later, and the "heterocyclesulfonyl" described later. Examples thereof include amino, methylamino, dimethylamino, ethylamino, diethylamino, ethylmethylamino, benzylamino, acetylamino, benzoylamino, methyloxycarbonylamino, and methylsulfonylamino. Preferable examples thereof include amino, methylamino, dimethylamino, ethylmethylamino, diethylamino, acetylamino, and methylsulfonylamino.

In the present specification, "substituted or unsubstituted carbamoyl" includes substituted or unsubstituted aminocarbonyl in which the substituted or unsubstituted amino part is the above "substituted or unsubstituted amino". Examples thereof include carbamoyl, N-methylcarbamoyl, N,N-dimethylcarbamoyl, N-ethyl-N-methylcarbamoyl, N,N-diethylcarbamoyl, N-benzylcarbamoyl, N-acetylcarbamoyl, and N-methylsulfonylcarbamoyl. Preferable examples thereof include carbamoyl, N-methylcarbamoyl, N,N-dimethylcarbamoyl, and N-methylsulfonylcarbamoyl.

In the present specification, "aryl" includes a monocyclic or condensed cyclic aromatic hydrocarbon. This may be condensed at possible all positions with the "cycloalkyl" described above, the "heteroaryl" described later, and the "heterocycle" described later. When the aryl is any of monocyclic and a condensed ring, the aryl can bind at all possible positions. Examples thereof include phenyl, 1-naphthyl, 2-naphthyl, anthryl, tetrahydronaphthyl, 1,3-benzodioxolyl, and 1,4-benzodioxanyl. Preferable examples thereof include phenyl, 1-naphthyl, and 2-naphthyl. Further preferable examples thereof include phenyl.

In the present specification, "heterocyclic" or "heterocycle" includes a non-aromatic heterocyclic group which may contain 1 to 4 heteroatoms such as an oxygen atom, a sulfur atom and a nitrogen atom in a ring, and may have a combined hand at a replaceable arbitrary position. In addition, such a non-aromatic heterocyclic group may be further crosslinked with an alkyl chain having 1 to 4 carbon atoms, or may be condensed with cycloalkane (5- to 6-membered ring is preferable), or a benzene ring. It may be saturated or unsaturated as far as it is non-aromatic. Preferably, it is a 5- to 8-membered ring and, further, may be condensed with a non-aromatic heterocyclic ring. Examples thereof include pyrrolinyl (e.g., 1-pyrrolinyl, 2-pyrrolinyl, 3-pyrrolinyl), pyrrolidinyl (e.g., 1-pyrrolidinyl, 2-pyrrolidinyl, 3-pyrrolidinyl), pyrrolidinone, imidazolinyl (e.g., 1-imidalinyl, 2-imidazolinyl, 4-imidazolinyl), imidazolidinyl (e.g., 1-imidazolidinyl, 2-imidazolidinyl, 4-imidazolidinyl), imidazolidinone, pyrazolinyl (e.g., 1-pyrazolinyl, 3-pyrazolinyl, 4-pyrazolinyl), pyrazolidinyl (e.g., 1-pyrazolidinyl, 3-pyrazolidinyl, 4-pyrazolidinyl), piperidinone, piperidino, piperidinyl (e.g., 2-piperidinyl, 3-piperidinyl, 4-piperidinyl), piperazinyl (e.g., 1-piperazinyl, 2-piperazinyl), piperazinone, morpholinyl (e.g., 2-morpholinyl, 3-morpholinyl), morpholino, tetrahydropyranyl, and tetrahydrofuranyl.

In the present specification, "heteroaryl" includes a 5- to 6-membered aromatic ring containing one or more heteroatoms arbitrarily selected from an oxygen atom, a sulfur atom or a nitrogen atom, etc. in a ring. "Heteroaryl" includes an aromatic cyclic group among the "heterocyclic groups". This may be condensed at possible all positions with the "cycloalkyl" described above, the "aryl" described above, the "heterocycle" described above, or other heteroaryls. When the heteroaryl is any of monocyclic and a condensed ring, it can bind at all possible positions. Examples thereof include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl, 4-pyrazolyl), isothiazolyl (e.g., 3-isothiazolyl), isoxazolyl (e.g., 3-isoxazolyl), oxazolyl (e.g., 2-oxazolyl, 4-oxazolyl, 5-oxazolyl), thiazolyl (e.g., 2-thiazolyl, 4-thiazolyl, 5-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-inidolizinyl, 6-indolizinyl), isoindolyl (e.g., 2-isoindolyl), indolyl (e.g., 1-indolyl, 2-indolyl, 3-indolyl), indazolyl (e.g., 3-indazolyl), purinyl (e.g., 8-purinyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acrinidyl, 2-acrynidyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), benzodioxolyl (e.g. 1,3-benzodioxolyl) etc.

In the present specification, "heterocyclic group" includes a heterocyclic group having one or more heteroatoms arbitrarily selected from oxygen, sulfur and nitrogen, etc. in a ring and, specific examples thereof include 5- to 6-membered heteroaryls such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, or thiadiazolyl; a non-aromatic heterocyclic group such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, and tetrahydropyridazinyl; dicyclic condensed heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotriazinyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzoxezinyl, dihydrobenzodioxepinyl, and dihydrothienodioxynyl; and tricyclic condensed heterocyclic groups such as carbazolyl, acridinyl, xanthenyl, phenothiazinyl, phenoxathiinyl, phenoxazinyl, dibenzofuryl, imidazoquinolyl, and tetrahydrocarbazolyl; etc. Preferable are 5- to 6-membered heteroaryls or non-aromatic heterocyclic groups.

In the present specification, "alkylene" means straight or branched alkylene having 1 to 10 carbon atoms, and examples thereof include methylene, 1-methylmethylene, 1,1-dimethylmethylene, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene, and 2,2-di-n-propyltrimethylene. Particularly, straight or branched alkylene having 2 to 6 carbon atoms is preferable.

In the present specification, "alkenylene" means straight or branched alkenylene having 2 to 10 carbon atoms, and examples thereof include ethenylene, 1-methylethenylene, 1-ethylethenylene, 1,2-dimethylethenylene, 1,2-diethylethenylene, 1-ethyl-2-methylethenylene, propenylene, 1-methyl-2-propenylene, 2-methyl-2-propenylene, 1,1-dimethyl-2-propenylene, 1,2-dimethyl-2-propenylene, 1-ethyl-2-propenylene, 2-ethyl-2-propenylene, 1,1-diethyl-2-propenylene, 1,2-diethyl-2-propenylene, 1-butenylene, 2-butenylene, 1-methyl-2-butenylene, 2-methyl-2-butenylene, 1,1-dimethyl-2-butenylene, and 1,2-dimethyl-2-butenylene. Particularly, straight or branched alkenylene having 2 to 6 carbon atoms is preferable.

In the present specification, "alkynylene" includes a straight or branched divalent carbon chain having 2 to 10 carbon atoms, preferably 2 to 6 carbon atoms, preferably 2 to 4 carbon atoms, which has a triple bond at an arbitrary position and, further, may have a double bond. Specific examples thereof include ethynylene, propynylene, butynylene, pentynylene and hexynylene.

In the present specification, the alkyl part of "alkylcarbonyl" means the above "alkyl".

In the present specification, the alkenyl parts of "alkenyloxy" and "alkenylcarbonyl" mean the above "alkenyl".

In the present specification, the aryl parts of "aryloxy" and "arylcarbonyl" mean the above "aryl".

In the present specification, the heteroaryl part of "heteroarylcarbonyl" means the above "heteroaryl".

In the present specification, the heterocycle part of "heterocyclecarbonyl" means the above "heterocycle".

In the present specification, the aryl part of "arylsulfonyl" means the above "aryl".

In the present specification, the heteroaryl part of "heteroarylsulfonyl" means the above "heteroaryl".

In the present specification, the heterocycle part of "heterocyclesulfonyl" means the above "heterocycle".

In the present specification, examples of a typical heteroatom and/or heteroatom group which can replace a carbon atom include, but are not limited to, the followings: —O—, —S—, —S—O—, —NR'—, —PH—, —S(O)—, —S(O)$_2$—, —S(O)NR'—, —S(O)$_2$NR'—, etc., and a combination thereof. Herein, each R' is independently hydrogen or (C1-C6) alkyl.

In the present specification, "aromatic ring system" refers to an unsaturated ring or a polycyclic ring system having a conjugated π electron system. A condensed ring system in which one or more rings are aromatic, and one or more rings are saturated or unsaturated, for example, fluorene, indane, indene, phenalene, and tetrahydronaphthalene are specifically included in definition of "aromatic ring system". Typical examples of the parent aromatic ring system include, but are not limited to, the followings: aceanthrylene, acenaphthylene, acephenanthrylene, anthracene, azlene, benzene, chrysene, coronene, fluorancene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, and trinaphthalene, as well as a variety of hydro isomers thereof.

In the present specification, "non-aromatic condensed carbocyclic group" includes a group in which two or more cyclic groups selected from the above "cycloalkyl", "cycloalkenyl" and "aryl" are condensed and, specific examples thereof include indanyl, indenyl, tetrahydronaphthyl and fluorenyl.

In the present specification, examples of a substituent of "substituted or unsubstituted carbocyclic group" and "substituted or unsubstituted heterocyclic group" include arbitrary substituents, preferably, one or more groups selected from the group consisting of lower alkyl and a substituent group α.

In the present specification, a substituent in "substituted or unsubstituted alkyl", "substituted or unsubstituted alkenyl", "substituted or unsubstituted alkynyl", "substituted or unsubstituted aryl", "substituted or unsubstituted cycloalkyl", "substituted or unsubstituted cycloalkenyl", "substituted or unsubstituted heteroaryl", "substituted or unsubstituted heterocycle", "substituted or unsubstituted acyl", "substituted or unsubstituted alkoxy", "substituted or unsubstituted alkylene", "substituted or unsubstituted alkenylene", and "substituted or unsubstituted alkynylene" is selected, for example, from the group consisting of hydroxy, carboxy, halogen, halogenated alkyl (e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), aryl (e.g., phenyl, naphthyl), arylalkyl (e.g., benzyl, phenethyl), heteroaryl (e.g., pyridyl, furyl), heteroarylalkyl (e.g., pyridylmethyl), heterocycle (e.g., piperidyl), heterocycloalkyl (e.g., morpholylmethyl), alkoxy (e.g., methoxy, ethoxy, propoxy, butoxy), halogenated alkyloxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino (e.g., alkylamino (e.g., methylamino, ethylamino, dimethylamino), acylamino (e.g., acetylamino, benzoylamino), arylalkylamino (e.g., benzylamino, tritylamino), hydroxyamino, alkylaminoalkyl (e.g., diethylaminomethyl), sulfamoyl, etc. The group can be substituted with 1 to 4 of the substituents. Alternatively, the group may be substituted with one or more groups selected from the group consisting of lower alkyl and a substituent group α.

The above-defined groups may further include a prefix and/or a suffix which is generally used in the art for producing a sufficiently recognized substituent. As an example, "alkyloxy" or "alkoxy" refers to a group of the formula —OR", "alkylamine" refers to a group of the formula —NHR", and "dialkylamine" refers to a group of NR"R", wherein each R" is independently alkyl. As another example, "haloalkoxy" or "haloalkyloxy" refers to a group of the formula —OR'", wherein R'" is haloalkyl.

In the present specification, "solvate" means a solvate of the compound of the present invention or a pharmaceutically acceptable salt thereof and, for example, includes a solvate with an organic solvent (e.g., alcoholate (e.g., ethanolate)), and a hydrate. When a hydrate is formed, it may be coordinated with any number of water molecules. Examples of the hydrate include monohydrate, and dihydrate.

In the present specification, "prodrug" refers to a substance which is modified so that it does not exhibit the drug action in an original form, or only exhibits very weak activity, but exhibits pharmacological activity for the first time or increases pharmacological activity by being metabolized in a living body, taking advantages of a metabolism mechanism of a living body. As the pharmaceutically acceptable prodrug of the present invention, any form known in the art can be adopted. Examples of the prodrug include an ester and an amide, in addition to a salt and a solvate.

In the present specification, a term of "pharmaceutically acceptable salt, ester, amide, and prodrug", as used herein, refers to carboxylate, amino acid adduct salt, ester, amide, and prodrug of the compound of the present specification, and this refers to a substance which is in a range of normal medical determination, is suitable for use in contact with a tissue of a patient without excessive toxicity, inflammation and allergic response, and is effective for the intended use of the compound of the present invention.

In the present specification, a term of "salt" refers to relatively non-toxic inorganic or organic acid addition salts of the compound of the present invention. These salts can be prepared by separately reacting purified compounds with a suitable organic or inorganic acid, transiently or in the form of a free base, during final isolation and purification of the compound, and isolating the thus formed salts.

Examples of the pharmaceutically acceptable salt of the compound of the present invention include the following salts.

Examples of a pharmaceutically acceptable basic salt of the compound of the present invention include alkali metal salts such as a sodium salt, and a potassium salt; alkaline earth metal salts such as a calcium salt, and a magnesium salt; ammonium salts; aliphatic amine salts such as a trimethylamine salt, a triethylamine salt, a dicyclohexylamine salt, an ethanolamine salt, a diethanolamine salt, a triethanolamine salt, a procaine salt, a meglumine salt, a diethanolamine salt and an ethylenediamine salt; aralkylamine salts such as N,N-dibenzylethylenediamine, and a benethamine salt; heterocyclic aromatic amine salts such as a pyridine salt, a picoline salt, a quinoline salt, and an isoquinoline salt; quaternary ammonium salts such as a tetramethylammonium salt, a tetraethylammonium salt, a benzyltrimethylammonium salt, a benzyltriethylammonium salt, a benzyltributylammonium salt, a methyltrioctylammonium salt, and a tetrabutylammonium salt; basic amino acid salts such as an arginine salt, and a lysine salt; etc.

Examples of a pharmaceutically acceptable acidic salt of the compound of the present invention include inorganic acid salts such as hydrochloride, sulfate, nitrate, phosphate, carbonate, bicarbonate, and perchlorate; organic acid salts such as acetate, propionate, lactate, maleate, fumarate, tartarate, malate, citrate, and ascorbate; sulfonic acid salts such as methanesulfonate, isethionate, benzenesulfonate, and p-toluenesulfonate; acidic amino acid salts such as aspartate, and glutamate; etc.

Particularly, hydrochloric acid, phosphoric acid, tartaric acid or methanesulfonic acid is preferable. These salts can be formed by a generally performed method.

In the present specification, a term of "pharmaceutically acceptable ester" refers to relatively non-toxic esterified products of the compound of the present invention. These esters can be prepared by separately reacting purified compounds with a suitable esterifying agent, in situ, or in the form of a free acid form or hydroxyl, during final isolation and purification of the compound. Carboxylic acid can be converted into an ester via treatment with an alcohol in the presence of a catalyst. It is further intended that this term includes a lower hydrocarbon group which can be solvated under the physiological conditions, for example, an alkyl ester, a methyl ester, an ethyl ester and a propyl ester.

In the present specification, "isomer" is used in the same meaning as that generally used in the art, and refers to substances which have the same molecular formula, but are different in a structural formula and a nature. The isomer used in the present invention is not limited to a particular isomer, but includes all possible isomers (e.g., keto-enol isomer, imine-enamine isomer, diastereoisomer, optical isomer, diastereomer, geometric isomer, steric isomer, cis-trans isomer, conformational isomer and rotamer, etc.) and racemates. It is to be understood that one or more chiral centers are present in each of the compound of the present invention. It is to be understood that the present invention includes all stereochemistry types of each compound, for example, an enantiomer, a diastereomer and a racemic compound. When an asymmetric carbon atom is present, more than one steric isomers are possible, and it is intended that all possible isomers are included in expression of an indicated structure. Arbitrarily, active (R) and (S) isomers may be separated using a conventional technique known to a person skilled in the art. It is intended that the present invention includes possible diastereomers as well as racemic compounds and optically resolved isomers.

Throughout the following description, it is to be understood that when a particular double bond is shown, both of cis configuration and trans configuration are included. An exemplary chemical formula is provided with particular configuration and, for completeness, a double bond can be changed. For the purpose of maintaining simplicity of the specification, not all structural isomers are shown. However, it should not be, in fact, deemed to be limitation. In addition, it is to be understood that when a synthesis scheme is provided, all cis/trans configuration isomers are also intended, and are included in a range of a synthesis method.

Hydroxyl in the compound of the present invention can be protected with a variety of protective groups such as those known in the art.

In the present specification, "protective group" refers to a group of atoms which, when bound to a reactive functional group in a molecule, masks, decreases or hampers reactivity of the functional group. Typically, the protective group may be selectively removed as desired during a process of synthesis. Examples of the protective group can be seen in Greene and Wuts, Protective Groups in Organic Chemistry, third edition, 1999, John Wiley & Sons, NY and Harrison et al., Compendium of Synthetic Organic Methods, Vols. 1-8, 1971-1996, John Wiley & Sons, NY. Examples of a representative nitrogen protective group include, but are not limited to, the followings: formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and a substituted trityl group, allyloxycarbonyl, 9-fluorenylmethyloxycarbonyl ("FMOC"), nitro-veratryloxycarbonyl ("NVOC"), etc. Examples of a representative hydroxyl protective group include, but are not limited to, those in which a hydroxyl group has been acetylated (esterified) or alkylated, for example, benzyl ether and trityl ether, as well as alkyl ether, tetrahydropyranyl ether, trialkylsilyl ether (e.g., a TMS group or a TIPPS group), glycol ether, for example, ethylene glycol and propylene glycol derivatives, and allyl ether.

A person skilled in the art can easily determine which protective group can be useful for protecting a hydroxyl group. A standard method is known in the art, and is more completely described in documents. For example, a suitable protective group can be selected by a person skilled in the art, and is described in Green and Wuts, "Protecting Groups in Organic Synthesis", John Wiley and Sons, Chapters 5 and 7, 1991, and this teaching is incorporated in the present specification by reference. A preferable protective group includes methyl and ethyl ether, a TMS or TIPPS group, acetic acid (ester) or a propionic acid group, and glycol ether, for example, ethylene glycol and propylene glycol derivatives.

For example, one or more hydroxyl groups are treated with a mild base, for example, triethylamine in the presence of an acid chloride or silyl chloride, and therefore, a reaction between hydroxyl ions and a halide can be made easy. Alternatively, alkyl halide is reacted with hydroxyl ions (generated by a base such as lithium diisopropylamide), and therefore, formation of an ether can be made easy.

Resolvins/Protectins refer to the followings: 5S,12R,18R-trihydroxy-6Z,8E,10E,14Z,16E-eicosapentaenoic acid; Resolvin E1a; 5S,18R-dihydroxy-6E,8Z,11Z,14Z,16E-eicosapentaenoic acid: Resolvin E2; 7S,8,17R-trihydroxy-docosa-4Z,9E,11E,13Z,15E,19Z-hexaenoic acid: aspirin trigger-type Resolvin D1; 7S,16,17R-trihydroxy-docosa-4Z,8E,10Z,12E,14E,19Z-hexaenoic acid: aspirin trigger-type Resolvin D2; 4S, 11,17R-trihydroxy-docosa-5,7E,9E,13Z,15E,19Z-hexaenoic acid: aspirin trigger-type Resolvin D3; 4S,5,17R-trihydroxy-docosa-6E,8E,10Z,13Z,15E,19Z-hexaenoic acid: aspirin trigger-type Resolvin D4; 7S,17R-DiHDHA7S,17R-dihydroxy-docosa-5Z,8E,10Z,13Z,15E,19Z-hexaenoic acid: aspirin trigger-type Resolvin D5; 4S,17R-DiHDHA4S,17R-dihydroxy-docosa-5E,7Z,10Z,13Z,15E,19Z-hexaenoic acid: aspirin trigger-type Resolvin D6; 10,17R-DiHDHA10,17R-dihydroxy-docosa-4Z,7Z,11,13,15,19Z-hexaenoic acid: aspirin trigger-type 10,17R-docosatriene; 7S,8,17S-TriHDHA7S,8,17S-trihydroxy-docosa-4Z,9E,11E,13Z,15E,19Z-hexaenoic acid: Resolvin D1a; 7S,16,17S-TriHDHA7S,16,17S-trihydroxy-docosa-4Z,8E,10Z,12E,14E,19Z-hexaenoic acid: Resolvin D2a; 4S,11,17S-TriHDHA4S,11,17S-trihydroxy-docosa-5,7E,9E,13Z,15E,19Z-hexaenoic acid: Resolvin D3a; 4S,5,17S-TriHDHA4S,5,17S-trihydroxy-docosa-6E,8E,10Z,13Z,15E,19Z-hexaenoic acid; Resolvin D4a; 7S,17S-DiHDHA7S,17S-dihydroxy-docosa-5Z,8E,10Z,13Z,15E,19Z-hexaenoic acid: Resolvin D5; 4S,17S-DiHDHA4S, 17S-dihydroxy-docosa-5E,7Z,10Z,14Z,16E,19Z-hexaenoic acid: Resolvin D6a; 10,17S-DiHDHA10,17S-dihydroxy-docosa-4Z,7Z,11E,13E,15Z,19Z-hexaenoic acid: 10,17S-docosatriene, Neuroprotectin D1; 16,17S-dihydroxy-docosa-4Z,7Z,10Z,12E,14E,19Z-hexaenoic acid: 16,17S-docosatriene; 16,17-epoxy-docosa-4Z,7Z,10Z,12E,14E,19Z-hexaenoic acid: 16,17-epoxy-docosatriene.

The compound of the present invention is a substance which is different from Resolvin/Protectin and is thought not to be a conventionally known substance.

PREFERABLE EMBODIMENTS

Preferable embodiments of the present invention are shown below. Embodiments provided below are provided for better understanding of the present invention, and the scope of the present invention is not limited by the following descriptions. Therefore, it is apparent that a person skilled in the art can appropriately make modification within the scope of the present invention, in view of the descriptions in the present specification.

(Compound)

In one aspect, the present invention provides the following compound.

There is provided a compound selected from:

[Chemical Formula 20]

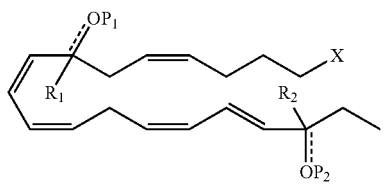

[Chemical Formula 21]

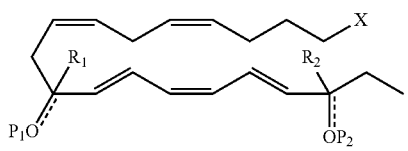

[Chemical Formula 22]

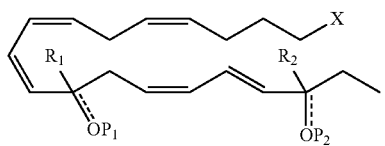

[Chemical Formula 23]

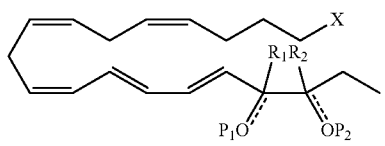

[Chemical Formula 24]

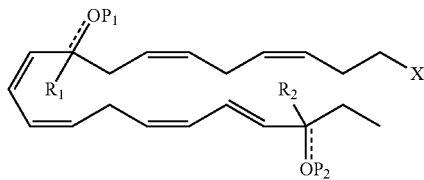

[Chemical Formula 25]

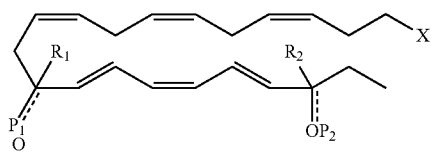

[Chemical Formula 26]

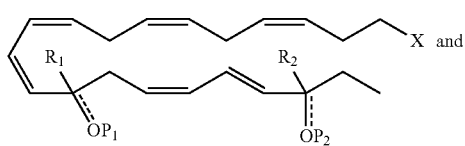 and

[Chemical Formula 27]

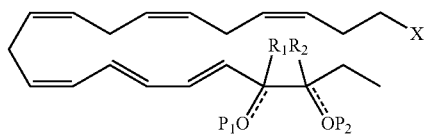

or a pharmaceutically acceptable salt or solvate thereof;
wherein
$P_1$ and $P_2$ are each independently a protective group, a hydrogen atom, alkyl, a hydroxyl group or a substituted hydroxyl group or a combination thereof, when

[Chemical Formula 28]

----- indicates a single bond,
$P_1$, $P_2$, $R_1$ and $R_2$ are not present, when

[Chemical Formula 29]

----- indicates a double bond, and when

[Chemical Formula 30]

----- is a single bond,
$R_1$ and $R_2$ are each independently a hydrogen atom, a halogen atom, a substituted or unsubstituted branched or non-branched alkyl group, a substituted or unsubstituted aryl group, a substituted or unsubstituted branched or non-branched alkylaryl group, or a combination thereof;
X is —C(O)OR$_3$, —C(O)NR$_4$R$_5$, —C(O)H, —C(NH)NR$_4$R$_5$, —C(S)H, —C(S)OR$_3$, —C(S)NR$_4$R$_5$, or —CN;
$R_3$ is hydrogen, a protective group, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle or a group of the formula: —NR$_a$R$_b$ (wherein R$_a$ and R$_b$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or R$_a$ and R$_b$ may be taken together with an adjacent nitrogen atom to form a substituted or unsubstituted nitrogen-containing heterocyclic ring); R$_4$ and R$_5$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or R$_4$ and R$_5$ may be taken together with an adjacent nitrogen atom to form a substituted or unsubstituted nitrogen-containing heterocyclic ring; and double bond configurations of the compound can be each independently any of cis or trans.

These compounds will be described in more detail below.

8,18-diHEPE-Associated Compound

In one aspect, the present invention provides a compound having the chemical formula:

[Chemical Formula 31]

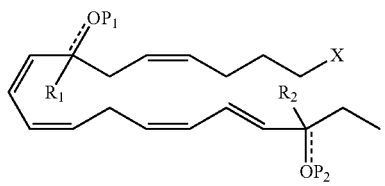

and a pharmaceutical composition. Herein,

[Chemical Formula 32]

-----, $P_1$, $P_2$, $R_1$, $R_2$ and X are independently as defined above.

In a particular embodiment, $P_1$ and $P_2$ are each a hydrogen atom, $R_1$ and $R_2$ are each independently a methyl group or a hydrogen atom or a combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

11,18-diHEPE-Associated Compound

In one aspect, the present invention provides a compound having the chemical formula:

[Chemical Formula 33]

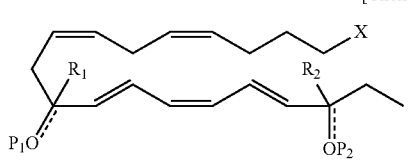

and a pharmaceutical composition. Herein,

[Chemical Formula 34]

-----, $P_1$, $P_2$, $R_1$, $R_2$ and X are each independently as defined above.

In a particular embodiment, $P_1$ and $P_2$ are each a hydrogen atom, $R_1$ and $R_2$ are each independently a methyl group or a hydrogen atom or a combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

12,18-diHEPE-Associated Compound

In one aspect, the present invention provides a compound having the chemical formula:

[Chemical Formula 35]

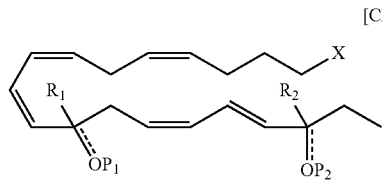

and a pharmaceutical composition. Herein,

[Chemical Formula 36]

-----, $P_1$, $P_2$, $R_1$, $R_2$ and X are each independently as defined above.

In a particular embodiment, $P_1$ and $P_2$ are each a hydrogen atom, $R_1$ and $R_2$ are each independently a methyl group or a hydrogen atom or a combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

17,18-diHEPE-Associated Compound

In one aspect, the present invention provides a compound having the chemical formula:

[Chemical Formula 37]

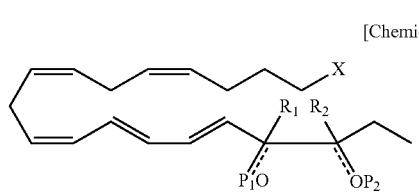

and a pharmaceutical composition. Herein,

[Chemical Formula 38]

-----, $P_1$, $P_2$, $R_1$, $R_2$ and X are each independently as defined above.

In a particular embodiment, $P_1$ and $P_2$ are each a hydrogen atom, $R_1$ and $R_2$ are each independently a methyl group or a hydrogen atom or a combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

10,20-diHDoPE-Associated Compound

In one aspect, the present invention provides a compound having the chemical formula:

[Chemical Formula 39]

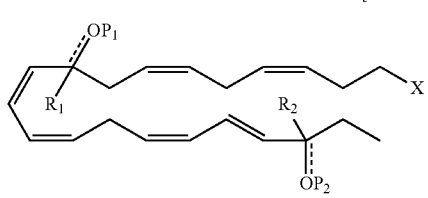

and a pharmaceutical composition. Herein,

[Chemical Formula 40]

-----, $P_1, P_2, R_1, R_2$ and X are each independently as defined above.

In a particular embodiment, $P_1$ and $P_2$ are each a hydrogen atom, $R_1$ and $R_2$ are each independently a methyl group or a hydrogen atom or a combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

13,20-diHDoPE-Associated Compound

In one aspect, the present invention provides a compound having the chemical formula:

[Chemical Formula 41]

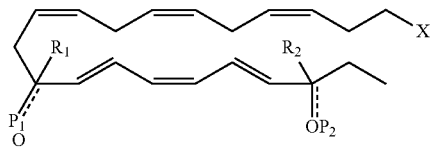

and a pharmaceutical composition. Herein,

[Chemical Formula 42]

-----, $P_1, P_2, R_1, R_2$ and X are each independently as defined above.

In a particular embodiment, $P_1$ and $P_2$ are each a hydrogen atom, $R_1$ and $R_2$ are each independently a methyl group or a hydrogen atom or a combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

14,20-diHDoPE-Associated Compound

In one aspect, the present invention provides a compound having the chemical formula:

[Chemical Formula 43]

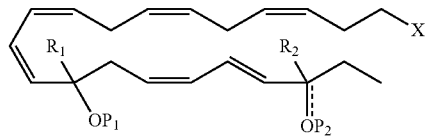

and a pharmaceutical composition. Herein,

[Chemical Formula 44]

-----, $P_1, P_2, R_1, R_2$ and X are each independently as defined above.

In a particular embodiment, $P_1$ and $P_2$ are each a hydrogen atom, $R_1$ and $R_2$ are each independently a methyl group or a hydrogen atom or combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

19,20-diHDoPE-Associated Compound

In one aspect, the present invention provides a compound having the chemical formula:

[Chemical Formula 45]

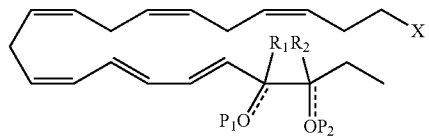

and a pharmaceutical composition, Herein,

[Chemical Formula 46]

-----, $P_1, P_2, R_1, R_2$ and X are each independently as defined above.

In a particular embodiment, $P_1$ and $P_2$ are each a hydrogen atom, $R_1$ and $R_2$ are each independently a methyl group or a hydrogen atom or a combination thereof, and X is carboxylic acid or a carboxylic acid ester.

X can be carboxylic acid, ester, amide, thiocarbamate, carbamate, thioester, thiocarboxamide, or nitrile. Preferably, X is carboxylic acid, a carboxylic acid ester, or pharmaceutically acceptable carboxylate.

These compounds are all metabolites of eicosapentaenoic acid (EPA) and docosahexaenoic acid (DHA) belonging to ω3 series PUFA, are metabolites such as 12/15LOX and 8-LOX which have not been conventionally known, and can be said to be an entirely novel compound group in that they belong to other series metabolites which are different from metabolites such as known resolvins and protectins.

In a particular embodiment, when $R_1$, $R_2$, $P_1$ and $P_2$ are each a hydrogen atom and Z is carboxylic acid, a compound may be either isolated, and/or purified. The purity of such a compound, based on analysis measurement using GC, MS, or $^1$H NMR, is a purity of at least 80%, particularly, a purity of at least about 90%, more particularly, a purity of at least 95%, and more preferably, a purity of at least about 99%. This applies in all isolated compounds and/or purified compounds, throughout the present specification.
(Other Altered Forms of Compounds)
In other aspect, the present invention can be expressed as follows.
A compound selected from:

[Chemical Formula 47]

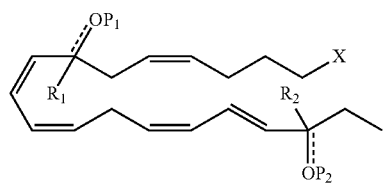

[Chemical Formula 48]

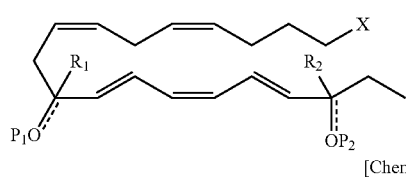

[Chemical Formula 49]

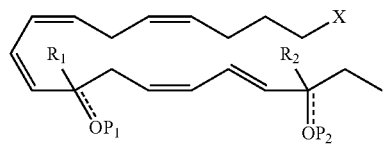

[Chemical Formula 50]

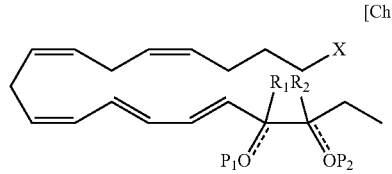

[Chemical Formula 51]

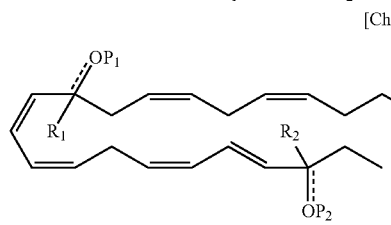

[Chemical Formula 52]

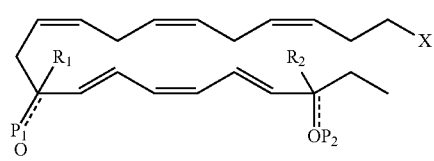

[Chemical Formula 53]

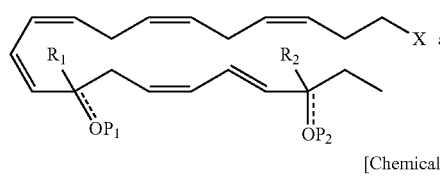

[Chemical Formula 54]

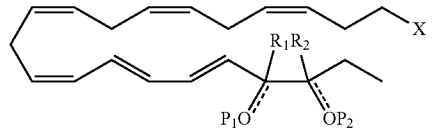

or a pharmaceutically acceptable salt or solvate thereof, wherein
$P_1$ and $P_2$ are each independently a protective group, a hydrogen atom, alkyl, a hydroxyl group or a substituted hydroxyl group or a combination thereof, when

[Chemical Formula 55]

----- indicates a single bond,
$P_1$, $P_2$, $R_1$ and $R_2$ are not present, when

[Chemical Formula 56]

----- indicates a double bond, and when

[Chemical Formula 57]

----- is a single bond,
$R_1$ and $R_2$ are each independently a hydrogen atom, a halogen atom, a substituted or unsubstituted branched or non-branched alkyl group, a substituted or unsubstituted aryl group, a substituted or unsubstituted branched or non-branched alkylaryl group or a combination thereof;
X is —C(O)ORd, —C(O)NRcRc, —C(O)H, —C(NH)NRcRc, —C(S)H, —C(S)ORd, —C(S)NRcRc, or —CN;
each Ra, when present, is independently selected from the group consisting of hydrogen, (C1-C6)alkyl, (C3-C8)cycloalkyl, cyclohexyl, (C4-C11)cycloalkylalkyl, (C5-C10)aryl, phenyl, (C6-C16)arylalkyl, benzyl, 2- to 6-membered heteroalkyl, 3- to 8-membered cycloheteroalkyl, morpholinyl, piperazinyl, homopiperazinyl, piperidinyl, 4- to 11-membered cycloheteroalkylalkyl, 5- to 10-membered heteroaryl and 6- to 16-membered heteroarylalkyl;
each Rb, when present, is a suitable group independently selected from the group consisting of =O, —ORd, (C1-C3) haloalkyloxy, —OCF$_3$, =S, —SRd, =NRd, —NRcRc, halogen, —CF$_3$, —CN, —NC, —OCN, —SCN, —NO, —NO$_2$, =N$_2$, —N$_3$, —S(O)Rd, —S(O)$_2$Rd, —S(O)$_2$ORd, —S(O)NRcRc, —S(O)$_2$NRcRc, —OS(O)Rd, —OS(O)$_2$Rd, —OS(O)$_2$ORd, —OS(O)$_2$NRcRc, —C(O)Rd, —C(O)ORd, —C(O)NRcRc, —C(NH)NRcRc, —C(NRa)NRcRc, —C(NOH)Ra, —C(NOH)NRcRc, —OC(O)Rd, —OC(O)ORd, —OC(O)NRcRc, —OC(NH)NRcRc, —OC(NRa)NRcRc, —[NHC(O)]$_n$Rd, —[NRaC(O)]$_n$Rd, —[NHC(O)]$_n$ORd, —[NRaC(O)]$_n$ORd, —[NHC(O)]$_n$NRcRc, —[NRaC(O)]$_n$NRcRc, —[NHC(NH)]$_n$NRcRc and —[NRaC(NRa)]$_n$NRcRc;
each Rc, when present, is independently a protective group or Ra, or alternatively, each Rc may be taken together with a nitrogen atom to which it binds to form 5- to 8-membered cycloheteroalkyl or heteroaryl, and these may optionally comprise one or more same or different further heteroatoms, and may be optionally substituted with one or more same or different Ra groups or suitable Rb groups;
each n, when present, is independently an integer of 0 to 3; and
each Rd, when present, is independently a protective group or Ra.
In one embodiment, X is carboxylic acid, ester, pharmaceutically acceptable carboxylate, or a prodrug thereof.

In a particular embodiment, X is a pharmaceutically acceptable salt of carboxylic acid and, particularly, is an ammonium salt, or forms a prodrug.

In addition, in one embodiment, when C-5, C-6, C-12, C-13, C-14, C-15, C-16, C-17, C-18, C-19 or C-20 is present, if it is a chiral center, each may independently have R configuration or S configuration or R/S configuration.

In a certain embodiment, $P_1$ and $P_2$, when present, are each independently a hydrogen atom, and X is carboxylic acid or ester.

In another embodiment, one or more of $P_1$ and $P_2$ are a hydrogen atom, and X is carboxylic acid or ester.

In a particular embodiment, $R_1$ and $R_2$, when present, are each independently a lower alkyl group such as methyl, ethyl or propyl, and can be halogenated like trifluoromethyl. In one embodiment, at least one of $R_1$ and $R_2$, when present, is not a hydrogen atom. Generally, X is carboxylic acid, and one or more of $P_1$ and $P_2$ are a hydrogen atom.

In a particular embodiment, $P_1$ and $P_2$ are each independently a hydrogen atom, and X is a carboxyl ester. In another embodiment, $P_1$ and $P_2$ are each independently a hydrogen atom, and X is carboxylic acid. In another embodiment, $P_1$ and $P_2$ are each independently a hydrogen atom, and X is not carboxylic acid.

In one aspect, the compound described in the present specification is isolated and/or purified and, particularly, a compound in which $P_1$ and $P_2$ are each independently a hydrogen atom, and X is carboxylic acid is isolated and/or purified.

The compound of the present invention is useful for treating a disease which can be treated or prevented by suppression of neutrophil, for example, an inflammatory disease. Such utility is variously present in addition to an inflammatory disease, and those described elsewhere in the present specification are exemplified.

Accordingly, in a preferable embodiment, the present invention provides the following compound or a pharmaceutically acceptable salt or solvate thereof:

[Chemical Formula 58]

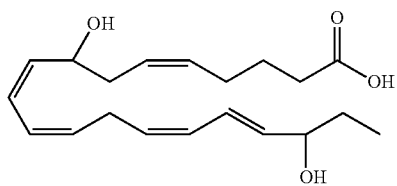

[Chemical Formula 59]

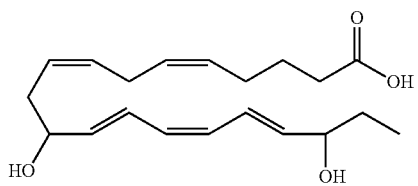

[Chemical Formula 60]

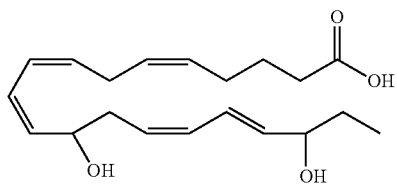

-continued

[Chemical Formula 61]

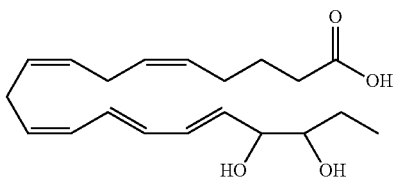

[Chemical Formula 62]

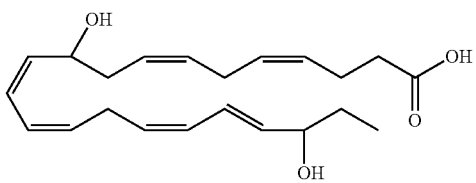

[Chemical Formula 63]

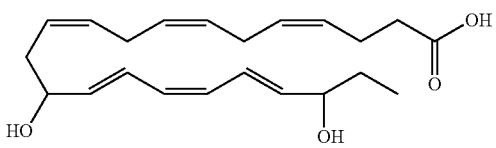

[Chemical Formula 64]

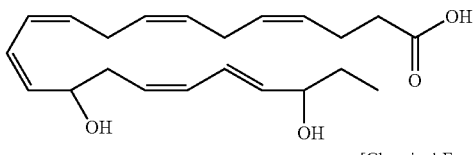

[Chemical Formula 65]

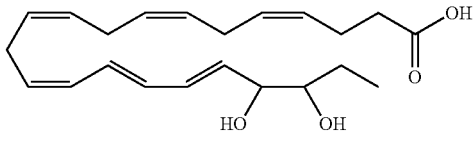

The compound described in the present specification has anti-inflammatory activity as recognized by down regulation of neutrophil infiltration in a peritonitis model.

It is to be understood that "X" found in the compound of the present invention can be changed from one particular part to another part by a person skilled in the art. In order to attain this, in a certain particular example, one or more groups can necessitate protection. This is also within a range of a person skilled in the art. For example, a carboxylic acid ester can be converted into an amide by treatment using an amine. Such interconversion is known in the art.

It is to be understood that, in the compound of the present invention, reference to "hydroxyl" stereochemistry is exemplary, and this term means to include a protected hydroxyl group and a free hydroxyl group. In a particular embodiment, the C-17 position has R configuration. In another embodiment, the C-17 position has S configuration. In another embodiment, a particular embodiment of the present invention has R configuration at the C-18 position.

The compound of the present invention can be protected with a variety of protective groups such as those known in the art. A person skilled in the art can easily determine which protective group can be useful for protecting a hydroxyl group using procedures etc. described in Green and Wuts, "Protecting Groups in Organic Synthesis", John Wiley and Sons, Chapters 5 and 7, 1991, and the present specification.

It is to be understood that, regarding the compound of the present invention, not all hydroxyl groups are necessary to be protected. One or two all hydroxyl groups can be protected. This can be attained by stoichiometric selection of reagents used for protecting a hydroxyl group, using procedures described in the known documents such as Green and Wuts, "Protecting Groups in Organic Synthesis", John Wiley and Sons, Chapters 5 and 7, 1991, and elsewhere in the present specification. The methods known in the art, for example, HPLC, liquid chromatography (LC), flash chromatography, gel permeation chromatography, crystallization, distillation, etc. can be used for separating a mono-protected or di-protected hydroxy compound.

It is understood that each of the above-identified compounds can take a variety of forms of isomers. Particularly, it is to be understood that one or more chiral centers are present in the compound of the present invention. It is to be understood that the present invention includes all stereochemistry types of each compound, for example, enantiomers, diastereomers or racemic compounds. When an asymmetric carbon atom is present, more than one steric isomers are possible, and it is intended that all possible isomer types are included in expression of an indicated structure. Optionally, active (R) and (S) isomers may be separated using a conventional technique known to a person skilled in the art. It is intended that the present invention includes possible diastereomers as well as racemic compounds and optically resolved isomers.

The compound of the present invention comprises an acetylenic and/or ethylenic unsaturated site. When a carbon double bond is present, steric configuration chemistry can be any of cis or trans (Z or E), and expression throughout the present specification does not mean limitation. The expression is generally presented based on steric configuration chemistry of an associated DHA or EPA compound, and is not limited by a theory, but is thought to have the same steric configuration chemistry. Throughout the present specification, a bond between carbons is simplified, particularly, in order to show a manner of finally arranging a bond to each other. For example, the acetylene part of resolvin actually comprises about 180° geometry, but it is to be understood that, in order to assist understanding of a relationship between synthesis, and a final product and a starting substance, in such an angle, extreme expression is used in order to assist understanding.

It is understood that the present invention also includes a compound which can generate one or more kinds of products by hydrogenation of the acetylene part. It is intended that all possible products are included in the present specification. For example, hydrogenation of the diacetylenic compound of the present invention can produce up to eight kinds of products (when hydrogenation of both acetylene parts are completed (it can be monitored by a known method), four kinds of diene products, that is, cis, cis; cis, trans; trans, cis; trans, trans), and four kinds of monoacetylene-monoacetylene products (cis or trans "monoene"-acetylene; acetylene-cis or trans "monoene"). All the products can be separated and identified by HPLC, GC, MS, NMR or IR.

A technique known in the art can be used for converting the carboxylic acid/ester functional group of the compound of the present invention into carboxamide, thioester, nitrile, carbamate or thiocarbamate, and is incorporated in the present specification. A suitable part such as an amide can be further substituted as known in the art.

(Production of the Compound of the Present Invention)

The compound of the present invention is synthesized by a general organic chemistry procedure, or can be produced by acting an enzyme such as lipoxygenase of 12/15-LOX etc. on 18-HEPE or 20-HDoHE etc. present relatively abundantly as a precursor.

Accordingly, the present invention provides a method of producing the compound of the present invention or a pharmaceutically acceptable salt or solvate thereof. This method includes the steps of A) contacting eicosapentaenoic acid (EPA) or docosahexaenoic acid (DHA), or 18-hydroxy eicosapentaenoic acid (18-HEPE) or 20-hydroxy docosahexaenoic acid (HDoHE) with 8-lipoxygenase (e.g., mouse recombinant 8-lipoxygenase (8-LOX)), 12-lipoxygenase (12-LOX) (e.g., platelet-type 12-LOX), 12/15-lipoxygenase (12/15-LOX) (e.g., lymphocyte-type 12/15-LOX), soybean lipoxygenase, or eosinophil or an extract thereof to obtain an enzyme metabolite; and B) reducing or oxidizing the enzyme metabolite as necessary, introducing a substituent as necessary, and separating or purifying the objective compound or a pharmaceutically acceptable salt or solvate thereof as necessary. When a peroxide (perhydroxy body) is generated, reduction of the peroxide produces a hydroxy body. When the hydroxy body is further oxidized, a corresponding ketone body is produced. Any of them has a possibility as a physiologically active substance. As these enzymes, the following can be utilized using a known technique. Mouse recombinant 8-LOX: Jisaka M. et al. J Biol Chem, 272, 24410-24416 (1997); platelet-type 12-LOX: Yoshimoto T. et al. Prostaglandins and Other Lipid Mediators Vol. 68-69, 245-262 (2002); lymphocyte-type 12/15-LOX: Kuhn H. et al. Prostaglandins and Other Lipid Mediators Vol. 68-69, 263-290 (2002); sLOX: Oliw E. H. Prostaglandins and Other Lipid Mediators Vol. 68-69; 313-324 (2002). Eosinophil may be used as it is, or an extract thereof may be used as far as objective enzyme activity is seen. It can be said that it is unexpected that 10,20-HDoPE is produced using 8-LOX. Therefore, a desired oxidized body can be obtained by, subsequently to A) step, carrying out the steps of B') contacting the enzyme metabolite obtained in A) step, after purification or without purification, with at least one selected from the group consisting of 8-lipoxygenase (8-LOX), 12-lipoxygenase (12-LOX), 12/15-lipoxygenase (12/15-LOX), soybean lipoxygenase (sLOX) and eosinophil or an extract thereof to obtain a secondary enzyme metabolite; as well as C') reducing or oxidizing the secondary enzyme metabolite as necessary, introducing a substituent as necessary, and separating or purifying the objective compound or a pharmaceutically acceptable salt or solvate thereof as necessary; as well as repeating these B') and C') steps as necessary. In B') step, since a plurality of peroxidized bodies can be obtained in A) step, they can be further oxidized by contacting them with the same enzyme or another enzyme again while they are individually separated (purified), or they are not subjected to purification. As purification used herein, the method described in the present specification is exemplified, and examples thereof include, but are not limited to, HPLC, and it is understood that a degree of separation or purification can be appropriately adjusted.

Figure 9A:
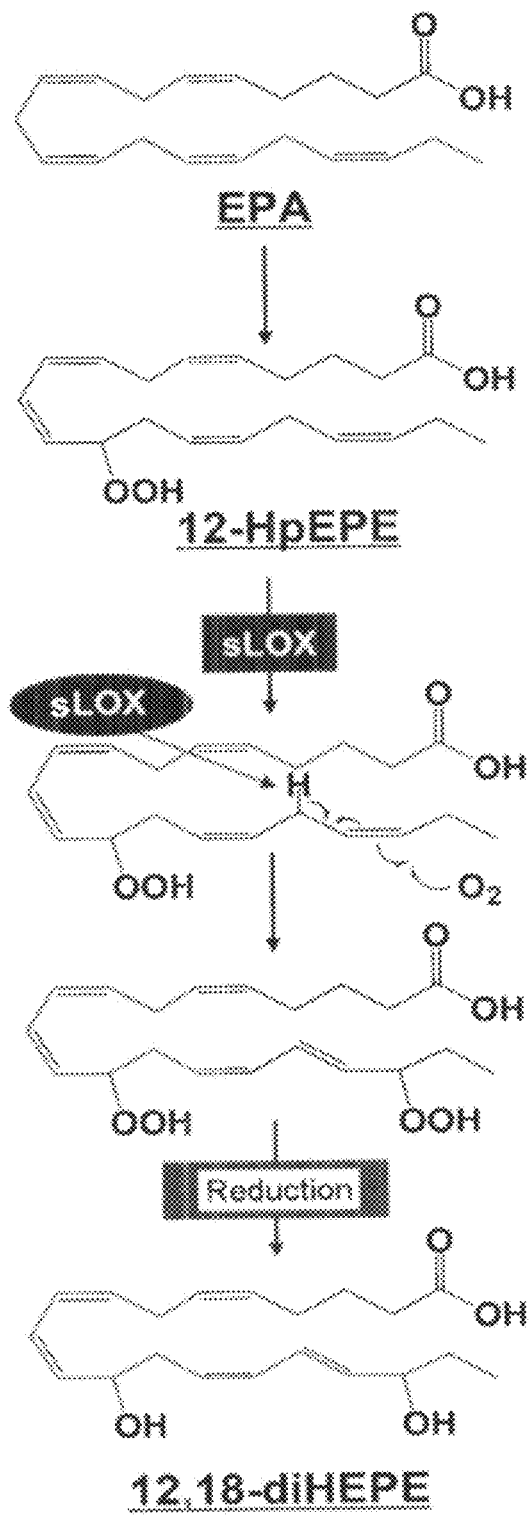
FIG. 9A shows a metabolism route using 12-HpEPE which is a metabolite of eicosapentaenoic acid (EPA) as an origin.

For example, an exemplary method includes a method comprising the steps of producing 12-hydroperoxy eicosapentaenoic acid (12-HpEPE) or 14-hydroperoxy docosahexaenoic acid (HpDoHE) using 12-LOX as necessary and, thereafter, A) contacting 12-hydroperoxy eicosapentaenoic acid (12-HpEPE) or 14-hydroperoxy docosahexaenoic acid (HpDoHE) with soybean lipoxygenase to obtain an enzyme metabolite; and B) reducing or oxidizing the enzyme metabolite as necessary, introducing a substituent as necessary, and separating or purifying the objective compound or a pharmaceutically acceptable salt or solvate thereof as necessary (FIG. 9A and FIG. 9B).

Using the above technique or other known techniques, the compound of the present invention can be produced using the following compounds:

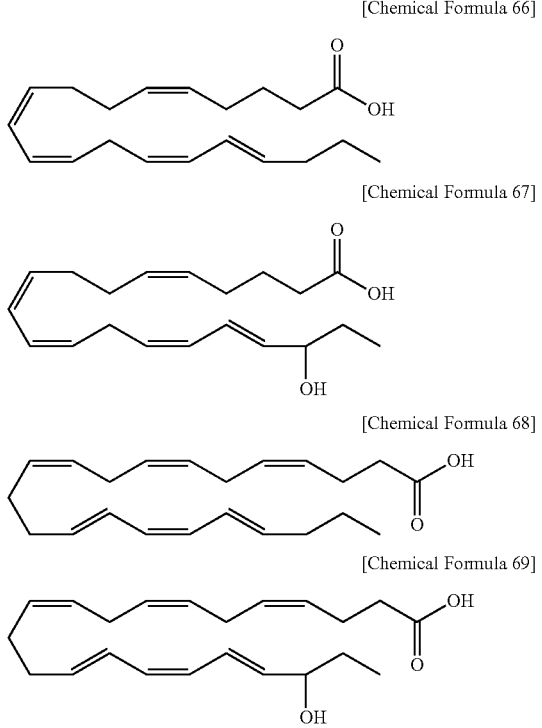

as a raw material.

Since EPA and DHA are present abundantly in a living body, they can be extracted using a food etc. as a raw material, or commercially available ones may be purchased. Herein, as 18-HEPE and 20-HDoPE, commercially available ones (available from Cayman) can be used, or they can be produced using the following procedure. 18-HEPE and 20-HDoHE are both metabolites in which just the ω3 site of ω3 PUFA has been oxidized.

Examples of the enzyme used in the method of production of the present invention include 8-lipoxygenase (e.g., mouse recombinant 8-lipoxygenase (8-LOX)), 12-lipoxygenase (12-LOX) (e.g., platelet-type 12-LOX), 12/15-lipoxygenase (12/15-LOX) (e.g., lymphocyte-12/15-LOX), soybean lipoxygenase, and an enzyme obtained from eosinophil, it is understood that a suitable enzyme can be appropriately utilized while the substrate specificity thereof is taken into consideration.

As the following precursor materials (18-HEPE and 20-HDoPE), commercially available substances (available from Cayman Inc.) can be utilized, or they can be obtained by chemical synthesis or extraction from a living body.

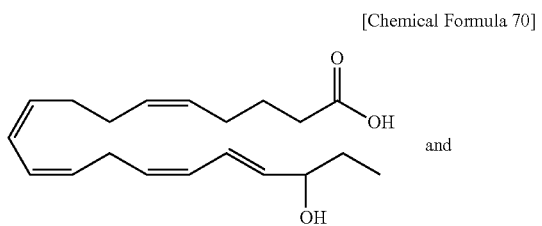 [SMILES: CCC(O)/C=C/C=C\C/C=C\C=C/C(O)C/C=C\CCCC(=O)O]

and

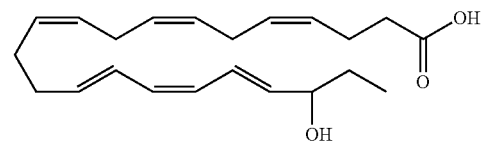

The method or technique of purification, separation or isolation used in the present specification, when necessary, includes column chromatography, high performance liquid chromatography (HPLC), gas chromatography (GC), crystallization, and distillation. Characterization can be performed by such as ultraviolet (UV) analysis, mass analysis (MS), MS/MS, GC/MS, or nuclear magnetic resonance (NMR). A person skilled in the art can utilize various methods for preparing, isolating and characterizing these novel compounds, based on the teaching of the present specification.

It is understood that, when $P_1$ and $P_2$ are other than hydrogen, for example, are each a protective group, a hydrogen atom, alkyl, a hydroxyl group or a substituted hydroxyl group or a combination thereof, the compound of the present invention can be produced by a method of introducing these substituents into a precursor, and performing an enzyme reaction using a technique known in the art, or a method of producing a compound in which each is hydrogen by the procedure described in the present specification, and thereafter introducing a substituent, or a combination thereof. As such a technique, the known technique of producing a derivative in resolvin/protectin can be applied.

For example, a compound in which $P_1$ and $P_2$ are other than hydrogen can be produced by producing a compound in which $P_1$ and $P_2$ are hydrogen and, thereafter, substituting the hydroxyl of the compound with an alkyl group or a variety of protective groups (e.g., those known in the art). A person skilled in the art can easily determine which protective group can be useful for protecting these hydroxyl groups. A standard method is known in the art, and is sufficiently described in documents. For example, substitution with an alkyl group, and substitution with a suitable protective group are carried out, and easily selected by a person skilled in the art, and a content described in Green and Wuts, "Protecting Groups in Organic Synthesis", John Wiley and Sons, Chapters 5 and 7, 1991 (the teaching content of which is incorporated in the present specification as reference) can be taken into consideration. Preferable examples of the protective group include methyl and ethyl esters, TMS and TIPPS groups, an acetic acid ester or a propionic acid ester, and glycol ether (e.g., ethylene glycol and propylene glycol derivatives). As such a technique, the known technique of producing a derivative in resolvin/protectin can be applied.

Alternatively, when $P_1$ and $P_2$ are each a hydroxyl group or a substituted hydroxyl group, that is, regarding a peroxide body, a product obtained by an enzyme reaction may be separated, or in the case of a substituted hydroxyl group, a peroxide body may be further substituted with a substituent such as an alkyl group, or a protective group using the known technique. As such a technique, the known technique of producing a derivative in resolvin/protectin can be applied.

When $R_1$ and $R_2$ are other than hydrogen, for example, are each a halogen atom, a substituted or unsubstituted branched or non-branched alkyl group, a substituted or unsubstituted aryl group, a substituted or unsubstituted branched or non-branched alkylaryl group or a combination thereof, it is understood that the compound of the present invention can be produced by a method of introducing these substituents into a precursor, and performing an enzyme reaction using a technique known in the art, or a method of producing a compound in which each is hydrogen by the procedure described in the present specification, and thereafter introducing a substituent, or a combination thereof. As such a technique, the known technique of producing a derivative in resolvin/protectin can be applied.

Herein, when $R_1$ and $R_2$ are other than hydrogen, that is, use of "R protecting chemistry" is not necessarily required in an adjacent diol in the compound of the present invention. Typically, the adjacent diol is not easily oxidized and, for this reason, generally, such protection is not required by substitution of a hydrogen atom adjacent to the oxygen atom of a hydroxyl group. Therefore, it is generally deemed that such protection is not necessary, and it is possible to prepare a compound in which the hydroxyl group of an adjacent diol "can be protected" independently by substitution of a hydrogen atom adjacent to the oxygen atom of a hydroxyl group, using the aforementioned substituent as a protective group. As such a technique, the known technique of producing a derivative in resolvin/protectin can be applied.

For introducing such $R_1$ and $R_2$ groups, for example, a hydroxyl group is oxidized by Pfitzner-Moffatt oxidation, Swern oxidation, Jones oxidation etc., to obtain a ketone, and a substituent such as alkyl, aryl, or alkylaryl can be introduced into $R_1$ and $R_2$ together with reduction into an alcohol, by Grignard reaction, Barbier coupling reaction, Kagan-Molander reaction in the presence of diiodosamarium, etc. and, if necessary, $P_1$, $P_2$, etc. can be further introduced thereinto. As such a technique, the known technique of producing a derivative in resolvin/protectin can be applied.

The following synthesis route illustrates a method of preparing the objective compound of the present invention. A preparation product does not intend limitation, but more traditionally, works as another means for preparing the compound of the present invention in line with implementation, and should be deemed as complementation for the biological synthesis.

The compound of the present invention can be also synthesized by an organic synthesis method.

(Biological Activity, Drug and Medicament, Therapy, and Use In Production of Medicament)

In one aspect, the present invention provides a neutrophil suppressing agent comprising the compound of the present invention or a pharmaceutically acceptable salt or solvate thereof.

Alternatively, in another aspect, the present invention provides a method of treating or preventing an inflammatory disease comprising the step of administering the compound of the present invention or a pharmaceutically acceptable salt or solvate thereof to a subject in need of the treatment or the prevention.

In still another aspect, the present invention relates to use of the compound of the present invention or a pharmaceutically acceptable salt or solvate thereof for producing a medicament, in the method of treating or preventing an inflammatory disease.

In still another aspect, the present invention relates to use of the compound of the present invention or a pharmaceutically acceptable salt or solvate thereof for producing a medicament for treating or preventing a disease, a disorder or a state associated with neutrophil.

In the medicament, drug (neutrophil suppressing agent etc.), treating method, preventing method, and production of a medicament for treatment or prevention, there are the followings embodiments. They will be described in turn below.

Therefore, the present invention can, for example, prevent infiltration into a tissue of, and activation of neutrophil at acute inflammation. Such preventing ability is useful for preventing infiltration into a tissue of, and activation of neutrophil found in ischemic reperfusion disorder, cerebral apoplexy, cardiac infarction, acute nephritis, etc. Therefore, since the present invention strongly suppresses infiltration into a tissue of, and activation of neutrophil at a very low dose, it is understood that it is useful as having an effect thereof as a therapeutic. In addition, also in chronic inflammatory diseases such as rheumatoid arthritis, inflammatory colitis and asthma, since the compound of the present invention has been found to be an endogenous substance originally present in a living body, a therapy improving effect having little side effect for intermediate to long term administration is expected.

In the present specification, "disease, disorder or symptom associated with neutrophil" refers to a disease, a disorder or a symptom which is improved by inhibiting neutrophil. Such a disease state or symptom is described throughout the present specification, the entire of which is incorporated in the present specification. The currently unknown state associated with neutrophil regulation, which may be found in the future, is included in the present invention, because characterization as a state associated with neutrophil regulation can be easily determined by a person skilled in the art.

In one embodiment, the present invention also relates to a method of treating, remitting or curing a disease state or a symptom associated with inflammation.

A disease which is a target of the present invention includes the followings. Many gastrointestinal inflammatory disorders of an alimentary system (mouth, stomach, esophagus, small intestine and large intestine), for example, stomatitis, periodontal disease, esophagitis, gastritis, inflammatory intestinal diseases such as ulcerative colitis and Crohn disease, infectious enterocolitis (viral, bacterial, parasitic organismic), antibiotic-associated diarrhea, *Clostridium difficile* colitis, microscopic or lymphocytic colitis, collagenous colitis, colon polyp and familiar polyp syndrome (e.g., familiar polyposis syndrome, Gardner syndrome), *Helicobacter pylori*, irritable bowel syndrome, non-specific diarrhea, and intestine cancer; inflammatory diseases such as inflammatory bowel disease (IBD), colitis which is induced by stimulation from external world (e.g., inflammation of gastrointestine (e.g., colitis) which is caused by therapeutic regimens such as administration of chemotherapy, and radiation therapy, or is associated therewith (e.g., as side effect)), chronic granulomatous disease, Celiac disease, celiac sprue (genetic disease in which the back layer of an intestine causes inflammation in response to ingestion of protein known as gluten), food allergy, gastritis, infectious gastritis, or enterocolitis (e.g., *Helicobacter pylori* infectious chronic active gastritis) and other type of gastrointestine inflammation caused by an infectious factor; lung diseases such as lung distress syndrome, adult respiratory distress syndrome, and chronic obstructive pulmonary syndrome (COPD); ischemic diseases such as ischemic cardiac disease, ischemic renal disease, ischemic brain disease, and ischemic liver disease; stress-associated diseases such as erosive gastritis, stomach ulcer, duodenal ulcer, bronchial asthma, ulcerative colitis, arteriosclerosis, Crohn disease, malignant tumor, ovarian cyst, salpingitis, uterine myoma, endometriosis, spontaneous abortion, gestosis, infertility and dysmenorrhea.

Inflammation includes acute and chronic inflammatory states. Acute inflammation is generally characterized by onset in a short time, and infiltration or inflow of neutrophil. Chronic inflammation is generally characterized by onset in a relatively long term (e.g., a few days, a few weeks, a few months, or a few years, and up to a life of a subject) and infiltration or inflow of mononuclear cells. Chronic inflammation is also typically characterized by a term of spontaneous recovery and spontaneous development.

In one aspect, the present invention provides a medicament comprising the compound of the present invention or a pharmaceutically acceptable salt or solvate thereof.

The compound of the present invention or a pharmaceutically acceptable salt thereof can be administered alone as it is, but is usually preferably provided as various medical formulations. Those medical formulations can be used in an animal and human.

As an administration route, a route which is the most effective upon therapy is preferably used, and examples thereof include oral routes and parenteral routes such as intrarectal, intravaginal, intranasal, oral cavity, sublingual, transdermal, subcutaneous, intramuscular, and intravenous. The amount of an active ingredient which can be combined with a carrier material for producing a single dosage form is generally an amount of a compound generating a therapeutic effect. Generally, among 100 percent, this amount is in a range of about 1 percent to about 99 percent of an active ingredient, preferably, about 5 percent to about 70 percent, and most preferably, about 10 percent to about 30 percent.

As an administration form, there are capsules, tablets, pills, granules, powders, syrups, lozenges (preferable base, usually, sucrose and acacia or tragacanth are used), emulsions, suppositories, injectables, etc. Liquid preparations such as emulsions and syrups which are suitable for oral administration can be produced employing water, sugars such as sucrose, sorbit, and fructose, glycols such as polyethylene glycol, and propylene glycol, oils such as a sesame oil, an olive oil, and a soybean oil, antiseptics such as p-hydroxybenzoic acid esters, flavors such as strawberry flavor, and peppermint, etc. In addition, capsules, tablets, powders, granules etc. can be produced by using excipients such as lactose, glucose, sucrose, and mannit, disintegrating agents such as starch, and sodium alginate, lubricants such as magnesium stearate, and talc, binding agents such as polyvinyl alcohol, hydroxypropylcellulose, and gelatin, surfactants such as fatty acid ester, plasticizers such as glycerin, etc. Alternatively, the preparations may be as solutions or suspensions in an aqueous or non-aqueous liquid, or as oil in water or water in oil liquid emulsions, or as elixirs or syrups, or aromatic tablets (using inactive bases such as gelatin and glycerin, or sucrose and acacia) and/or mouth wash, and each comprises a predetermined amount of the compound of the present invention as an active ingredient. The compound of the present invention can also be administered as boluses, electuaries or pastes.

Formulations suitable for parenteral administration comprised of sterilized aqueous formulations comprising an active compound which is preferably isotonic with blood of a recipient. For example, in the case of injectables, solutions for injection are prepared using carries comprised of salt solutions, glucose solutions or a mixture of an aqueous salt and a glucose solution, etc.

In the present specification, "pharmaceutically acceptable carrier" means a pharmaceutically acceptable material, composition or vehicle, for example, a liquid or solid filler, diluent, excipient, solvent or capsulating material, which is contained upon carriage or transportation of the compound of the present specification into or to a subject so that the carrier conducts the intended performance. Typically, such a compound can be carried or transported from one organ or a part of a body to another organ or part of a body. Each carrier must be "acceptable" in a sense that it is compatible with other ingredients of formulations, and is not harmful to a patient. Some examples of a material which can work as a pharmaceutically acceptable carrier include: sugars such as lactose, glucose and sucrose; starches such as corn starch and potato starch; cellulose such as carboxymethylcellulose sodium, ethylcellulose and cellulose acetate and derivatives thereof; powdery tragacanth; malt; gelatin; talc; excipients such as cocoa butter and suppository wax; oils such as a peanuts oil, a cottonseed oil, a safflower oil, a sesame oil, an olive oil, a corn oil and a soybean oil; glycols such as propylene glycol, polyols such as glycerin, sorbitol, mannitol, and polyethylene glycol; esters such as ethyl oleate and ethyl laurate; agar; buffers such as magnesium hydroxide and aluminum hydroxide; alginic acid; water not containing a pyrogen; isotonic physiological saline; Ringer's solution; ethyl alcohol; phosphate buffer; other non-toxic compatible materials utilized in pharmaceutical formulations.

In a particular embodiment, the compound of the present invention may comprise one or more acidic functional groups and, therefore, can form a pharmaceutically acceptable salt with a pharmaceutically acceptable base. Regarding such a salt or base, for example, Berge S. M. et al., "Pharmaceutical Salts", J. Pharm. Sci, 1977; 66:1-19 ca be referred (this is incorporated in the present specification as reference).

Local formulations are prepared by dissolving or suspending an active compound in one or more kinds of media, for example, mineral oils, petroleum, and polyhydric alcohols or other bases used in local pharmaceutical formulations. Formulations for intraintestinal administration are provided as suppositories by preparation using normal carriers, for example, cacao butter, hydrogenated fat, and hydrogenated fat carboxylic acid.

In the present invention, also in parenteral agents, one or more kinds of auxiliary ingredients selected from glycols, oils, flavors, antiseptics (including antioxidants), excipients, disintegrating agents, lubricants, binding agents, surfactants, plasticizers, etc. exemplified in oral agents can also be added.

Examples of a pharmaceutically acceptable antioxidant include water-soluble antioxidants such as ascorbic acid, cysteine hydrochloride, sodium bisulfate, sodium metabisulfate, and sodium sulfite; oil-soluble antioxidants such as ascorbyl palmitate, butylated hydroxyanisole (BHA), butylated hydroxytoluene (BHT), lecithin, propyl gallate, and α-tocopherol; and metal chelating agents such as citric acid, ethylenediaminetetraacetic acid (EDTA), sorbitol, tartaric acid, and phosphoric acid.

A suitable dose for one day or one time of the compound of the present invention or a pharmaceutically acceptable salt thereof, etc. is an amount of the compound which is an effective minimum dose for generating a therapeutic effect, and it is understood that an effective dose and an administration time of the compound of the present invention or a pharmaceutically acceptable salt thereof, etc. are different depending on an administration form, an age and a weight of a patient, a nature and severity of symptom to be treated, etc. Usually, an oral administration amount is 0.01 to 1000 mg/person, preferably 5 to 500 mg/person per one day, and it is preferable that as an administration time, the compound is administered once a day or by division. Generally, the intravenous dose and subcutaneous dose of the compound of the present invention or a pharmaceutically acceptable salt thereof, etc. for a patient, when used for the indicated analgesic effect, are in a range of about 0.0001 to about 100 mg/kg weight per one day, more preferably about 0.01 to about 50 mg/kg weight per one day, and further more preferably about 0.1 to about 40 mg/kg weight per one day, and a therapeutic or preventive effective amount is, for example, 0.1 to 20 mg/kg weight, and more preferably 1 to 10 mg/kg weight. For example, the compound of the present invention at between about 0.01 μg to 20 μg, between about 20 μg to 100 μg, or between 10 μg to 200 μg is administered per 20 g of a subject weight. It should be noted that there is a possibility that the value of an administered dose may vary along with a type and severity of the state to be alleviated.

A method of preparing these formulations or compositions includes the step of combining the compound of the present invention with a carrier and, optionally, one or more kinds of auxiliary ingredients. Generally, formulations are prepared by the steps of uniformly and closely combining the compound of the present invention with a liquid carrier, or a finely divided solid carrier, or both of them and, then, molding a product if necessary.

In the present specification, in the solid dosage form (capsules, tablets, pills, sugar-coated tablets, powders, granules, etc.) of the present invention for oral administration, an active ingredient is mixed with one or more kinds of pharmaceutically acceptable carries, for example, sodium citrate or dipotassium phosphate and/or any of the followings: fillers or bulking agents such as starch, lactose, sucrose, glucose, mannitol, and/or silicic acid; binding agents such as carboxymethylcellulose, alginate, gelatin, polyvinylpyrrolidone, sucrose and/or acacia; humectants such as glycerol; disintegrating agents such as agar, calcium carbonate, potato or tapioca starch, alginic acid, particular silicic acid, and sodium carbonate; solution retardants such as paraffin; absorption accelerating agents such as a quaternary ammonium compound; wetting agents such as cetyl alcohol and monostearic acid glycerol; absorbents such as kaolin and bentonite clay; lubricants such as talc, calcium stearate, magnesium stearate, solid polyethylene glycol, sodium laurylsulfate and a mixture thereof; as well as coloring agents. In the case of capsules, tablets and pills, a pharmaceutical composition may also comprise buffers. The same type of a solid composition may also be utilized as fillers in filled soft and hard gelatin capsules employing an excipient such as lactose or milk sugar, as well as a high-molecular polyethylene glycol.

Tablets may be prepared by compression and molding with optionally selective one or more kinds of auxiliary ingredients. Compressed tablets may be prepared employing binding agents (e.g., gelatin or hydroxypropylmethylcellulose), lubricants, inactive diluents, preservatives, disintegrating agents (e.g., starch glycolate sodium or crosslinked carboxymethyl-cellulose sodium), surface active agents or dispersants. Molded tablets may be prepared by molding a mixture of powdery compounds wetted with an inactive liquid diluent using a suitable machine.

Tablets or other solid dosage forms of the pharmaceutical composition of the present invention, for example, sugar-coated tablets, capsules, pills, and granules may be optionally given or prepared with coatings and shells, for example, enteric coatings and other coatings well-known in the field of medicament formulations. These also may be prepared into formulations employing a variety of proportions of hydroxypropylmethylcellulose, other polymer matrices, liposomes and/or microspheres in order to provide delayed release or controlled release of an active ingredient therein, for example, in order to provide a desired release profile. These may be sterilized, for example, by filtration by passing through a bacterium-retaining filter, or incorporating a sterilizing drug in a type of a sterilizing solid composition which can be dissolved in sterilized water or a certain other sterilized injectable medium immediately before use. These compositions may also include optionally an opaquer, or they may be a composition which releases only an active ingredient, or preferentially releases an active ingredient to a particular part of a gastrointestinal tract optionally in a delayed manner. Examples of an embedding composition which can be used include polymeric substances and waxes. An active ingredient, when appropriate, can be a microcapsulated type accompanying one or more kinds of the excipients.

A liquid dosage form for oral administration of the compound of the present invention includes pharmaceutically acceptable emulsions, microemulsions, solutions, suspensions, syrups, and elixirs. In addition to an active ingredient which can be used in the present invention, the liquid dosage form can include inactive diluents which are generally used in the art, for example, water and other solvents, solubilizers and emulsifying agents, for example, ethyl alcohol, isopropyl alcohol, ethyl carbonate, ethyl acetate, benzyl alcohol, benzyl benzoate, propylene glycol, 1,3-butylene glycol, oils (particularly, cottonseed oil, peanut oil, corn oil, germ oil, olive oil, castor oil, and sesame oil), glycerol, tetrahydrofuryl alcohol, polyethylene glycol, and fatty acid ester of sorbitan, and a mixture thereof.

The oral composition of the present invention can also include, in addition to the inactive diluents, adjuvants such as wetting agents, emulsifying agents and suspending agents, sweeteners, perfumes, coloring materials, aromatic agents, and preservatives.

The suspension of the present invention may include, in addition to an active compound of the present invention, suspensions, for example, ethoxylated isostearyl alcohol, polyoxyethylene sorbitol, and sorbitan ester, microcrystalline cellulose, aluminum metahydroxide, bentonite, agar and tragacanth, and a mixture thereof.

A formulation of the pharmaceutical composition of the present invention may be provided as a suppository for rectal or vaginal administration, and this can be prepared by mixing one or more kinds of suitable non-stimulating excipients or carriers including, for example, cocoa butter, polyethylene glycol, suppository wax or salicylate, which are solid at room temperature but are liquid at a body temperature and, therefore, are dissolved in rectum or vaginal cavity, and release an active compound, with at least one compound of the present invention.

The formulation of the present invention encompasses also pessaries, tampons, creams, gels, pastes, foams, or spray preparations, including carries which are known in the art to be appropriate for vaginal administration.

A dosage form for locally or transdermally administering the compound of the present invention includes powders, sprays, ointments, pastes, creams, lotions, gels, solutions, patches, and inhalants. An active compound may be mixed with a pharmaceutically acceptable carrier, and an optional preservative, buffer or aerosol agent which can be necessary under the sterilized condition.

To ointments, pastes, creams, and gels may be added excipients such as animal and vegetable fats, oils, waxes, paraffins, starches, tragacanth, cellulose derivatives, polyethylene glycol, silicone, bentonite, silicic acid, talc and zinc dioxide, or a mixture thereof, in addition to an active compound of the present invention.

Powders and sprays can include, in addition to the compound of the present invention, excipients such as lactose, talc, silicic acid, aluminum hydroxide, calcium silicate, and a polyamide powder, or a mixture of these substances. Sprays can further include conventional aerosol agents, such as volatile unsubstituted hydrocarbons such as chlorofluorohydrocarbon as well as butane and propane.

Transdermal patches have an additional advantage of providing controlled delivery of the compound of the present invention to a body. Such a dosage form can be made by dissolving or dispersing a compound in a suitable medium. An absorption potentiating agent can be also used for increasing inflow of a compound crossing a skin. A rate of such inflow can be controlled by either of provision of a rate controlling membrane, or dispersion of an active compound in a polymer matrix or a gel.

It is intended that the present invention encompasses ophthalmic formulations, ocular ointments, powders or solutions, and such solutions are useful for treating conjunctivitis.

The pharmaceutical composition of the present invention is used for parenteral administration, includes at least one composition of the present invention combined with a pharmaceutically acceptable sterilized isotonic aqueous solution or non-aqueous solution, a dispersion, a suspension or an emulsion, or a sterilized powder which can be reconstituted into a sterilized injection solution or a dispersion immediately before use, and this may include antioxidants, buffers, bacteriostatic agents, solutes which are isotonic with blood of a recipient who is intended for formulations, or suspensions or thickeners.

Examples of a suitable aqueous and non-aqueous carrier which may be utilized in the pharmaceutical composition of the present invention include water, ethanol, polyol (e.g., glycerol, propylene glycol, and polyethylene glycol), and a suitable mixture thereof, a vegetable oil, for example, an olive oil, and an injectable organic ester, for example, ethyl oleate. Suitable flowability can be maintained by use of a coating material such as lecithin, maintenance of a particle size required in the case of dispersion, and use of a surfactant.

These compositions may also include adjuvants such as preservatives, wetting agents, emulsifying agents, and dispersants. Hampering of the action of microorganisms may be guaranteed by inclusion of a variety of antibacterial agents and anti-fungal agents, for example, paraben, chlorobutanol, phenol, and sorbic acid. It can be also desired that an isotonic, for example, a sugar and sodium chloride be contained in the composition. In addition, prolongation of absorption of an injectable pharmaceutical type can be attained by inclusion of an agent which delays absorption such as aluminum monostearate and gelatin.

In some cases, in order to prolong the effect of a drug, it is desired that absorption of a drug from subcutaneous or intramuscular injection be delayed. This may be attained by using a liquid suspension of a crystalline or amorphous substance having poor water-solubility. Then, a rate of absorption of a drug can depend on a rate of its dissociation and, then, can depend on a crystal size and a crystal type. Alternatively, delayed absorption of a drug type which has been parenterally administered is attained by dissolving or suspending a drug in an oil vehicle.

An injectable depo-type can be prepared by forming a microcapsule matrix of a subject compound in a biodegradable polymer such as polylactide-polyglycolide. Depending on a ratio of a drug relative to a polymer, a nature of a utilized particular polymer and a rate of drug release can be controlled. Examples of other biodegradable polymer include poly(orthoester) and poly(anhydride). A depo-injectable formulation can be also prepared by inclusion of a drug in a liposome or a microemulsion which is compatible with a body tissue.

The present invention also provides a packaged medicament including a novel compound described throughout the present specification, for use in treating or preventing a variety of disease states and symptoms.

In the present specification, "prevention" refers to no occurrence or at least delaying of a disease, a disorder or a symptom, by any means, before occurrence of the disease, the disorder or the symptom which is a target of the present invention, or making the state where even if a cause itself for a disease, a disorder or a symptom occurs, a disorder does not occur based on the cause.

In the present specification, "treatment" refers to arrestment of progression of a disease, a disorder or a symptom which is a target of the present invention, which has been already developed, or improvement in a disease, a disorder or a symptom which is a target of the present invention, whether complete or partial.

In the present specification, "subject" refers to an animal to be handled for a disease, a disorder or a symptom which is a target of the present invention. An animal to be handled by the present invention may be, for example, birds and mammals. Preferably, such an animal can be a mammal (e.g., monotreme, marsupial, edentate, dermatopteran, chiroptera, carnivore, insectivore, proboscideans, perissodactyl, artiodactyla, tubulidentata, squamata, sirenia, Cetacea, primate, rodent and Lagomorpha). Examples of an exemplary subject are not limited to, but include an animal such as cow, pig, horse, chicken, cat, and dog. Further preferably, a small animal such as mouse, rat, rabbit, hamster and guinea pig can be used. Of course, a subject of the present invention includes human, dog, cat, cow, goat and mouse.

Preparations of the present invention can be given orally, parenterally, locally or rectally. These, of course, are given by a suitable type regarding each administration route. For example, these are administered in tablets or capsules by administration by injection, infusion or inhalation of injections, inhalations, ocular lotions, ointments, suppositories etc.; in lotions or ointments locally; and in suppositories rectally.

In the present specification, phrases "oral administration" and "orally administered", when used in the present specification, usually mean an administration manner other than enteral and local administration by injection and, without limitation, include intravenous, intramuscular, intra-arterial, intrathecal, intravesical, intraorbital, intracardial, intradermal, intraperitoneal, transtracheal, subcutaneous, subepidermal, intra-articular, subcapsular, subarachnoid, intraspinal and sternal injections and infusions.

In the present specification, phrases "systemic administration", "systemically administered", "peripheral administration" and "peripherally administered", when used in the present specification, mean administration of a compound, a drug or other substance other than direct administration to a central nervous system, in which, as a result, it enters a system of a patient and, therefore, it is subjected to metabolism and other similar process, for example, subcutaneous administration.

The compound of the present invention can be administered to a human and other animal for treatment, orally, to noses, for example, by spraying, or by an optional suitable route including by powders, ointments or drops including buccals and sublingual formulations, rectally, intravaginally, parenterally, intracisternally, and locally.

Regardless of a selected administration route, the compound of the present invention which may be used in a suitable hydrate type, and/or the pharmaceutical composition of the present invention can be formulated into a pharmaceutically acceptable dosage form by the conventional method known to a person skilled in the art.

An actual drug administration level of an active ingredient in the pharmaceutical composition of the present invention can vary so that an amount of an active ingredient effective for attaining a desired therapeutic response to a particular patient, a composition, and an administration manner is obtained without accompanying toxicity to a patient.

A selected drug administration level depends on a variety of factors including activity of a particular compound of the present invention to be utilized, an ester, a salt or an amide thereof, a route of administration, a time of administration, a rate of excretion of a particular compound to be utilized, a term of treatment, other drug, compound and/or substance to be used in combination with a particular compound to be utilized, an age, a sex, a weight, the state, general health state, and the previous medical history of a patient to be treated, as well as the similar factors well-known in the medical field.

A physician or a veterinarian having normal skill in the art can easily determine and formulate a required effective amount of the pharmaceutical composition. For example, a physician or a veterinarian can initiate administration of the compound of the present invention in the pharmaceutical composition at a level less than that required for attaining the desired therapeutic effect, and gradually increase an administration amount until the desired effect is attained.

Generally, a suitable one day dose of the compound of the present invention is an amount of a compound which is an effective minimum dose for generating the therapeutic effect. Such an effective dose generally depends on the aforementioned factors. Generally, an intravenous dose and a subcutaneous dose of the compound of the present invention for a patient, when used for the indicated analgesic effect, are in a range of about 0.0001 to about 100 mg/kg weight per one day, more preferably, about 0.01 to about 50 mg/kg weight per one day, and further more preferably, about 0.1 to about 40 mg/kg weight per one day. For example, the compound of the present invention in a range from about 0.01 μg to 20 μg, from about 20 μg to 100 μg, or from 10 μg to 200 μg is administered per 20 g of a weight of a subject.

When desired, an effective one day dose of an active compound is separately administered, optionally, as 2, 3, 4, 5, 6 or more divided doses at a suitable interval throughout one day in a unit dosage form.

The pharmaceutical composition of the present invention includes a "therapeutically effective amount" or "preventively effective amount" of at least one compound of the present invention. The "therapeutically effect amount" refers to an effective amount at an administration amount and a time necessary for attaining the desired therapeutic result, for example, decrease or prevention of the effect associated with a variety of disease states or symptoms. A therapeutically effective amount of the compound of the present invention can vary according to factors such as a disease state, an age, a sex and a weight of an individual, and the ability of the therapeutic compound which induces the desired effect in an individual. The therapeutically effective amount also increases the therapeutically advantageous effect for arbitrary toxicity or harmful influence of a therapeutic. The "preventively effective amount" refers to an effective amount at an administration amount and a time necessary for attaining the desired preventive result. Typically, since a preventive dose is used before a disease or at an initial stage thereof, a preventive effective amount is smaller than a therapeutically effective amount.

A regimen can be adjusted for providing an optimal desired response (e.g., therapeutic response or preventive response). For example, a single time bolus can be administered, some divided doses can be administered over a time, or this dose can be proportionally decreased or increased as shown by the requirement of the therapeutic state. For easiness of administration and uniformity of drug administration, it is particularly advantageous to formulate a parenteral composition in a unit dosage form. A unit dosage form, when used in the present specification, refers to a physically discrete unit suitable as a unit administration amount for a mammal subject to be treated; each unit contains a predetermined amount of an active ingredient calculated to generate the desired effect in cooperation with a required pharmaceutical carrier. Details of a unit dosage form of the present invention are determined by (a) the peculiar properties of the compound of the present invention and the particular therapeutic or preventive effect which is attained, as well as (b) inherent limitation in the art of constitution of such an active compound in order to treat sensitivity in an individual, and directly depend on them.

An illustrative non-limiting range of a therapeutically or preventively effective amount of the compound of the present invention is 0.1 to 20 mg/kg, and more preferably 1 to 10 mg/kg. It should be noted that there is a possibility that a value of an administration amount varies with a type and severity of the state to be alleviated. It is to be further understood that, for an arbitrarily particular subject, a particular administration amount • an administration frequency etc. should be adjusted with time according to necessity of an individual, as well as professional determination of a person who manages a composition or supervises administration of a composition, and an administration amount range shown in the present specification is only illustrative, and does not intend to limit the scope and implementation of the present invention.

Delivery of the compound of the present invention to lung by inhalation is one method described throughout the present specification, for treating a variety of respiratory states (airway inflammation) including the general local state such as COPD such as bronchial asthma and chronic obstructive lung disease. The compound of the present invention can be administered to lung in an aerosol type having a respirable sized particle (diameter of less than about 10 μm). This aerosol preparation can be provided as a liquid or a dry powder. In order to guarantee the suitable particle size in a liquid aerosol, a particle can be prepared as a suspension at a respiratory size and, then, can be incorporated into a suspension formulation including an aerosol agent. Alternatively, a formulation can be prepared in a solution type in order to avoid a fear regarding a suitable particle size in a formulation. A solution formulation should be dispersed in a manner for producing particles or liquid droplets of a respiratory size.

Once prepared, the aerosol formulation is filled into an aerosol canister provided with a metered-dose valve. The formulation is dispensed via an actuator adapted to direct a dose from the valve to a subject.

The formulation of the present invention can be prepared by combining (i) a sufficient amount of at least one compound for providing a plurality of therapeutically effective doses; (ii) addition of water at an effective amount for stabilizing respective formulations; (iii) a sufficient amount of an aerosol agent for spraying a plurality of doses from an aerosol canister; and (iv) an optional further selective ingredient, for example, ethanol as a co-solvent; and dispersing ingredients. Ingredients can be dispersed by shaking using the conventional mixer or homogenizer, or by ultrasound energy. A bulk formulation can be moved to smaller individual aerosol vials by using a method of moving from a valve to a valve by filling a pressure, or by using the conventional cold filling method. It is not required that a stabilizer used is soluble in an aerosol agent in a suspension aerosol formulation. A stabilizer which is not well soluble can be coated on a suitable amount of a drug particle and, then, the coated particle can be incorporated into a formulation as described above.

In order to deliver the preparation of the present invention, the common valve, preferably an aerosol canister provided with a metered-dose valve can be also used. The conventional neoprene and buna valve rubbers used in a metered-dose valve for delivering the conventional CFC formulation can be used with a formulation including HFC-134a or HFC-227. A partition formed by extrusion, injection molding or compression molding from a thermoplastic elastomer material, for example, FLEXOMER™GERS 1085 NT polyolefin (Union Carbide) is also suitable.

The formulation of the present invention can be contained in the coated or not coated, anodized or not anodized conventional aerosol canister, for example, that of aluminum, glass, stainless steel, polyethylene terephthalate.

The formulation of the present invention can be delivered to a respiratory tract and/or lung by oral inhalation, in order to result in bronchodilation or treat the state sensitive to treatment by inhalation, for example, asthma, and chronic obstructive lung disease, as described throughout the present specification.

The formulation of the present invention can be also delivered by nasal inhalation as known in the art, in order to treat or prevent the aspiration state as referred throughout the present specification.

It is possible to administer the compound of the present invention alone, but it is preferable to administer the compound as a pharmaceutical composition.

The present invention also includes a packaging material, and a product including a formulation of the compound of the present invention contained in the packaging material. This formulation includes at least one compound of the present invention, and the packaging material includes a label or a package insert showing that the formulation can be administered to a subject at a constant amount, at a constant frequency, and for an effective term for treating or preventing one or more kinds of the states described in the present specification in order to treat such states. Such states are referred throughout the present specification, and are incorporated into the present specification by reference. As a suitable compound, the compound described in the present specification can be utilized.

More specifically, the present invention features a packaging material, and a product including at least one compound of the present invention contained in the packaging material. The packaging material includes a label or a manual showing that the formulation can be administered to a subject in order to treat or prevent a symptom associated with a disease discussed throughout the present specification.

From the foregoing, in a preferable aspect, the medicament of the present invention is useful in treatment or prevention of a disease, a disorder, a state or the like which is not limited to, but includes the following: lung diseases such as lung distress syndrome, adult respiratory distress syndrome, and chronic obstructive pulmonary syndrome (COPD); ischemic diseases such as ischemic cardiac disease, ischemic renal disease, ischemic brain disease, and ischemic liver disease; many gastrointestinal inflammatory disorders of an alimentary system (mouth, stomach, esophagus, small intestine and large intestine), for example, stomatitis, periodontal disease, esophagitis, gastritis, inflammatory intestinal disease such as ulcerative colitis and Crohn's disease, infectious enterocolitis (viral, bacterial, parasitic organismic), antibiotic-associated diarrhea, *Clostridium difficile* colitis, microscopic or lymphocytic colitis, collagenous colitis, colon polyp and familiar polyp syndrome (e.g., familiar polyposis syndrome and Gardner syndrome), *Helicobacter pylori*, irritable bowel syndrome, non-specific diarrhea, and intestine cancer; inflammatory diseases such as inflammatory bowel disease (IBD), colitis induced by stimulation from external world (e.g., inflammation of gastrointestine (e.g., colitis) caused by therapeutic regimen such as administration of chemotherapy, radiation therapy etc., or is associated therewith (e.g., as side effect)), chronic granulomatous disease, Celiac disease, celiac sprue (genetic disease in which aback layer of an intestine causes inflammation in response to ingestion of a protein known as gluten), food allergy, gastritis, infectious gastritis, or enterocolitis (e.g., *Helicobacter pylori* infectious chronic active gastritis) and other type of gastrointestine inflammation caused by an infectious factor; stress diseases such as erosive gastritis • stomach ulcer • duodenal ulcer • bronchial asthma, ulcerative colitis, arteriosclerosis, Crohn's disease, malignant tumor, ovarian cyst, salpingitis, uterine myoma, endometriosis, spontaneous abortion, pregnant toxicosis, infertility and dysmenorrheal.

More particularly, the present invention can also treat or prevent the following: enterogastritis, ulcerative colitis, Crohn's disease, infectious enteritis, antibiotic-associated diarrhea, *Clostridium difficile* colitis, microscopic or lymphotic colitis, collagenous colitis, large intestine polyp, familiar polyp, familiar polyposis syndrome, Gardner syndrome, *Helicobacter pylori*, irritable bowel syndrome, non-specific diarrhea, and intestine cancer, or inflammatory disease (allergic disease (allergic dermatitis • allergic rhinitis etc.), rheumatoid arthritis, anaphylaxis etc.), arteriosclerosis, vascular • circulatory disease, cancer • tumor (hypertrophic deconditioning), immune disease, cell proliferative disease, infectious disease and the like. For example, psoriasis, pulmonary fibrosis, glomerular nephritis, cancer, atherosclerosis, and anti-angiogenesis (e.g., tumor growth, diabetic retinopathy) are included. Specifically, for example, the pharmaceutical composition of the present invention is an agent for treating and/or preventing diseases such as encephalitis, myelitis and encephalomyelitis, meningitis, inflammatory multiple neuropathy, neuritis, dacryoadenitis, orbital inflammation, conjunctivitis (allergic conjunctivitis, spring keratoconjuctivitis etc.), keratitis, chorioretinal scar, endophthalmitis, retrobulbar neuritis, retinopathy, glaucoma, cellulitis, external otitis, perichondritis, tympanitis, salpingitis, mastoiditis, myringitis, labyrinthitis, pulpitis, periodontitis, sialitis, stomatitis, glossitis, thyroiditis, pericarditis, endocarditis, myocarditis, hypertension, cardiac failure, arteriosclerosis (atherosclerosis etc.), restenosis, ischemic reperfusion disorder, thrombosis (cardiac infarct, cerebral infarct etc.), obesity, angiitis, vasculitis, multiple arteritis, lymphadenitis, lymphoma, Hodgkin's disease, eosinophilic disease (eosinophilia, pulmonary eosinophilia, pulmonary aspergillosis etc.), inflammatory or obstructive airway disease (allergic rhinitis, chronic sinusitis, pneumonia, laryngitis, laryngotracheitis, bronchitis, asthma, acute lung disorder, acute respiratory distress syndrome, emphysema, chronic obstructive pulmonary disease etc.), pleurisy, pneumoconiosis, mesothelioma, esophagitis, gastro-jejunal ulcer, gastritis, duodenitis, food allergy, sepsis, hepatitis, hepatic fibrosis, hepatic cirrhosis, cholecystitis, pancreatitis, peritonitis, diabetes (type I diabetes, type II diabetes), inflammatory or allergic skin disease (atopic dermatitis, contact dermatitis (allergic contact dermatitis, irritant contact dermatitis etc.), psoriasis, hives, light allergic response, alopecia greata etc.), skin hypertrophic disorder (skin eosinophilic granuloma etc.), skin polymyositis, inflammation of subcutaneous adipose tissue, hyperthyroidism, sarcoidosis, autoimmune blood disease (hemolytic anemia, idiopathic thrombocytopenic purpura etc.), (systemic) lupus erythematodes, relapsing polychondritis, multiple leptomeningitis, sclerodoma, Wegener's granulomatosis, dermatomyositis, chronic active hepatitis, myasthenia gravis, Stevens-Johnson syndrome, idiopathic sprue, autoimmune inflammatory bowel disease (ulcerative colitis, Crohn's disease etc.), endocrine ophthalmopathy, sarcoidosis, alveolitis, chronic hypersensitivity pneumonitis, multiple sclerosis, primary biliary cirrhosis, uveitis, keratoconjunctivitis sicca, interstitial pulmonary fibrosis, iridocyclitis, psoriatic arthritis, glomerular nephritis, systemic sclerosis, systemic connective tissue disease (Sjogren's syndrome, Behcet's disease, diffuse myofascitis etc.), interstitial myositis, inflammatory multiple joint disorder, inflammatory arthritis, arthrorheumatism, osteoarthritis, synovitis, bursitis, thecitis, chronic multiple myelitis, nephritis syndrome, tubulointerstitial nephritis, cystitis, prostatitis, orchitis, epididymitis, salpingitis, ovaritis, trachelitis, female pelvic inflammation, vulvovaginitis, organ transplant rejection, bone-marrow transplant rejection, and graft versus host disease, and/or an agent for treating thermal injury or traumatic inflammation.

As described above, in obesity and insulin resistance (metabolic syndrome), inflammatory change accompanying infiltration of macrophage into a fat tissue greatly contributes to a disease state (Tilg, H. and Moschen, A. R. (2006) Nat. Rev. Immunol. 6, 772-783). Therefore, it is understood that the compound of the present invention is useful in such an adult disease.

In another aspect, the present invention also relates to a method of treating or preventing a gastrointestinal disease or the state in a subject, by administration by joint use with other anti-inflammatory agent, for example, other drug such as a steroid agent or NSAID (aspirin, ibuprofen etc.). These drugs can be administered at the same time or two different times.

All results in the drawings and the text are expressed as an average±SE of n animals per group. A statistical significant difference was determined by a Student's t-test. What is expressed by p value<0.05 etc. (in some cases, 0.07, or 0.01) is deemed as a significant difference.

(Method of Analyzing Compound of Present Invention)

In one aspect, the present invention provides a method of analyzing the present invention. This can be directed for assaying these compounds with a human body fluid (blood, urine, breast milk), or a biopsy material, as a therapeutic marker for assessing a n−3 state level effective as an index for developing therapeutic base for anti-inflammation. This includes LC-MS-MS and GC-MS properties, and this can also result in far easy development for handling an ELISA assay for monitoring these novel products.

Figure 1C:
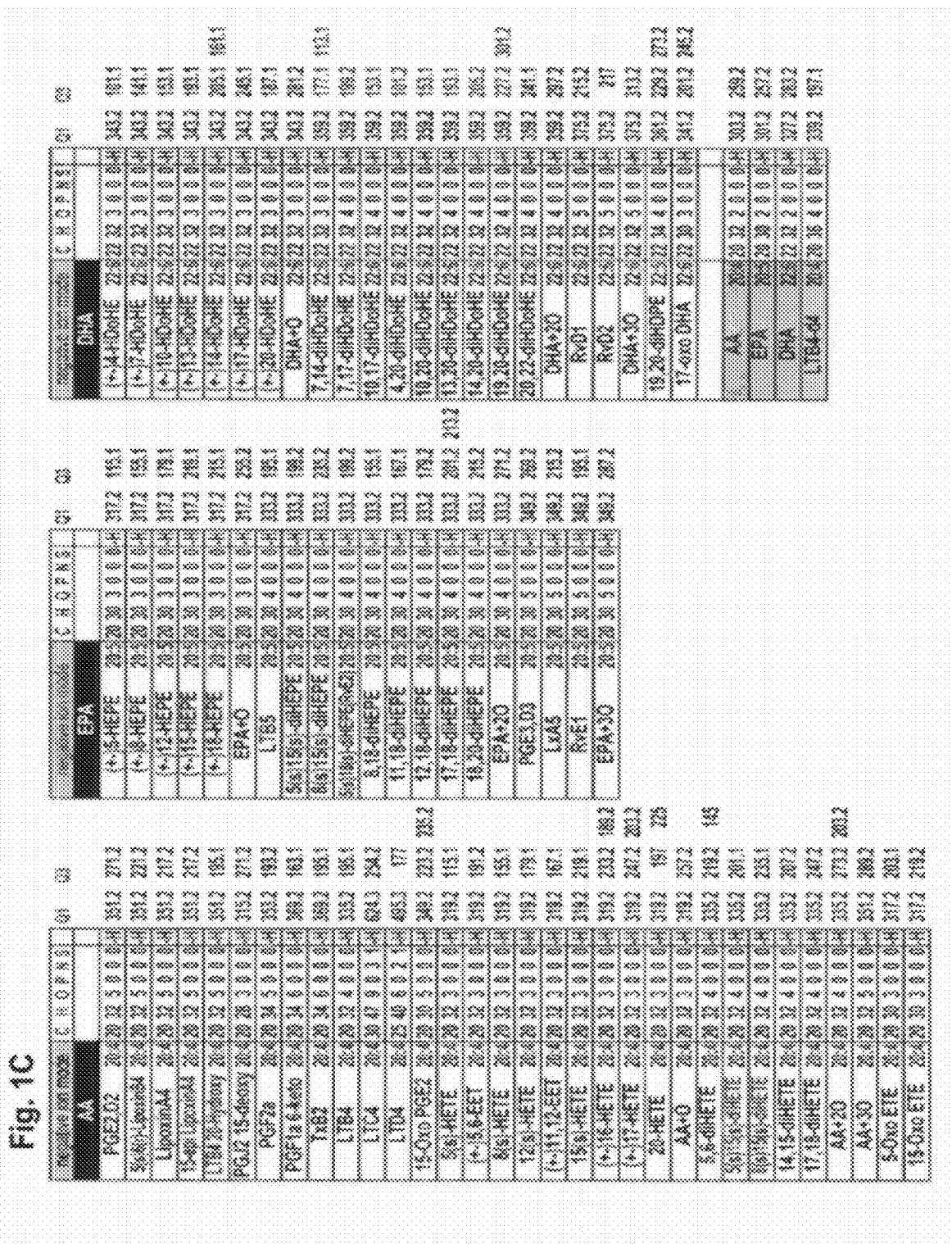
FIG. 1C is a list of polyunsaturated fatty acid (PUFA) metabolites to be measured by the conventional MRM. In the figure, EET represents epoxy eicosatrienoic acid, ETE represents eicosatetraenoic acid, HDoPE represents hydroxy docosapentaenoic acid, and DPE represents docosapentaenoic acid.

Therefore, the present invention provides a method of analyzing the compound of the present invention or a PUFA metabolite, including the following liquid chromatography condition:

using a solvent system using A liquid: water/acetic acid=100/0.1, and B liquid: acetonitrile/methanol=4/1, using a flow rate: 0 to 30 minutes→50 µL/minute, 30 to 33 minutes→80 µL/minute, 33 to 45 minutes→100 µL/minute, and a gradient described in FIG. 1B, and using multiple reaction monitoring including using parameters described in FIG. 1C.

In the condition setting, a pair of a parent mass and a child mass of MRM can be optimized (optimization of collision energy) from actually measured values of MS/MS, regarding a compound which could be synthesized (in the case of the present case, a compound synthesized with an enzyme, for example, 11,18-diHEPE and 17,18-diHEPE correspond thereto). In addition, when a calibration curve is produced, quantitative analysis becomes possible. Regarding a compound which cannot be synthesized (in the present case, corresponding to 12,18-diHEPE, 8,18-diHEPE), MRM for the purpose of detection can be performed by setting the hypothetical condition. By using this method, the novel compound of the present invention can be analyzed.

(General Technique)

A molecular biological procedure, a biochemical procedure, and a microbiological procedure used in the present specification are well-known and commonly used in the art, and described, for example, in Sambrook J. et al. (1989), Molecular Cloning: A Laboratory Manual, Cold Spring Harbor and its 3$^{rd}$ Ed. (2001); Ausubel, F. M. (1987), Current Protocols in Molecular Biology, Greene Pub. Associates and Wiley Interscience Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, separate volume (Experimental Medicine "Gene Introduction & Expression Analysis Experimental Method" YODOSHA CO., LTD., 1997 etc., and an associated part (all is possible) of them is in the present specification incorporated by reference.

DNA synthesis technique and nucleic acid chemistry for preparing an artificially synthesized gene are described, for example, in Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al., (1996). Nucleic Acids in Chemistry and Biology, Oxford University Press; Hermanson, G. T. (1996). Bioconjugate Techniques, Academic Press etc., and an associated part of them is in the present specification incorporated by reference.

Reference literatures such as scientific references, patents and patent applications cited in the present specification are incorporated by reference in their entirety in the present specification to the same extent as that each is specifically described.

In the foregoing, the present invention has been explained for easy understanding by showing preferable embodiments. The present invention will be explained below based on Examples, but the aforementioned explanation and following Examples are provided only for illustration, and are not provided for the purpose of limiting the present invention. Therefore, the scope of the present invention is not limited to embodiments or Examples which are specifically described in the present specification, and is limited only by claims.

EXAMPLES

The present invention will be explained in more detail below by way of Examples, but the technical scope of the present invention is not limited by the Examples etc. As reagents used below, commercially available ones are used except for the case where particularly mentioned.

Example 1

Analysis Regarding Metabolites of 18-HEPE and 20-HDoHE: Establishment of Highly Sensitive Method of Analyzing PUFA Metabolites In the present Example, in order to make it possible to also analyze a novel compound, first, establishment of a system capable of quantitatively analyzing many kinds of PUFA metabolites at once and at high sensitivity was tried. In the present Example, at once quantitative analysis system of polyvalent unsaturated fatty acid (PUFA) metabolites by Multiple Reaction Monitoring (MRM) using high performance liquid chromatography-tandem mass spectrometry (HPLC-MS/MS) was established.

MRM is a procedure which can analyze an objective metabolite selectively and at a high sensitivity using MS/MS (FIG. 1A). When MS/MS of a metabolite of PUFA is measured, for example, an oxide causes fragmentation at a carbon-carbon bond before and after its hydroxyl group. Then, a MS/MS value characteristic in a structure of the metabolite is detected. Then, a procedure of selectively detecting only a substance having a combination of parent MS value/child MS value, letting a MS value derived from a molecular weight of a certain metabolite (due to a negative ion mode, in the case of a PUFA metabolite, a MS value at extraction and ionization of a proton, molecular weight-1) to be a parent MS value ($M^-$), and a MS/MS value characteristic in a structure of the metabolite to be a child MS value ($A^-$) is MRM. Specifically, using triplicate quadrupole-type MS, a pre-set parent MS value is first selectively detected with Q1. At this time, other molecules are excluded, only molecules having passed through Q1 are given an energy at next q2, and are fragmented. Among generated fragments, only fragments having the pre-set child MS value are selectively detected at next Q3. A combination of this parent MS value/child MS value is adopted as one channel and, regarding all objective molecules, a combination of each parent mass value/child mass value, and a cone voltage, and a collision energy which are optimal for each of them are set as one channel. Since a scanning speed of one channel is about 30 msec., even when channels of 100 kinds of metabolites are analyzed, a time necessary for one time scanning is about 3 seconds. Therefore, when an elution time of a metabolite upon separation by LC is 3 seconds or longer, detection of the metabolite is possible. Since an actual elution time is around 10 and a few seconds, in principle, 300 or more kinds of metabolites can be detected. However, when performance of a detection around peak top is also taken into consideration, up to about one hundred and few tens kinds of metabolites can be analyzed at once while quantitative property is also retained. Further, by combining a separation system using LC, information of a retention time specific for each metabolite is obtained and, from information of them, at once quantitative analysis of an objective metabolite group at a high sensitivity can be performed.

In the present Example, as almost all compounds, synthesized products were purchased and used, but those which could not be purchased were prepared by an enzymatic reaction.

In order to examine metabolites generated from 18-HEPE and 20-HDoHE at inflammation, incubation of lymphocyte which is accumulating at an inflammation site at acute inflammation with 18-HEPE or 20-HDoHE can be performed, and comprehensive metabolome analysis of 18-HEPE metabolites and 20-HDoHE metabolites can be also performed by multiple reaction monitoring (MRM).

(Purification of Compound Using Normal Phase HPLC)
Hexane: Wako Pure Chemical Industries, Ltd
Isopropanol: Wako Pure Chemical Industries, Ltd
Acetic acid: Wako Pure Chemical Industries, Ltd
(Establishment of at Once Analysis System of PUFA Metabolites by MRM)

Standards of PUFA metabolites (standards having no particular description were purchased from Cayman)

$PGE_2$, 20-hydroxy-$PGE_2$, $PGD_2$, $PGF_{2\alpha}$, 6-keto-$PGF_{1\alpha}$, 15-deoxy-$\Delta^{12,14}$-$PGJ_2$, $LxA_4$, $LTB_4$, 20-hydroxy-$LTB_4$, $LTC_4$, $LTD_4$, $TxB_2$, 5-HETE, 5,6-EET, 8-HETE, 8,9-EET, 12-HETE, 11,12-EET, 15-HETE, 14,15-EET, 16-HETE, 17-HETE, 20-HETE, 5,15-diHETE, 8,15-diHETE, 14,15-diHETE, 17,18-diHETE, 5-oxo-ETE, 15-oxo-ETE, $LTB_5$: Biomol, RvE2 (gifted from the present department organic reaction chemistry laboratory), $PGE_3$, $PGD_3$, RvE1,5-HEPE, 8-HEPE, 12-HEPE, 15-HEPE, 14,15-EpETE, 18-HEPE, 17,18-EpETE, 11,18-diHEPE: synthesized using 18-HEPE (see the present specification), 17,18-diHEPE: synthesized using 18-HEPE (see the present specification), RvD1, 4-HDoHE, 7-HDoHE, 10-HDoHE, 13-HDoHE, 14-HDoHE, 17-HDoHE, 16,17-EpDPE, 20-HDoHE, 19,20-EpDPE, 7,17-diHDoHE: synthesized using DHA (see the present specification), 10,17-diHDoHE: synthesized using DHA (see the present specification)), arachidonic acid: SIGMA, DHA: SIGMA, EPA:SIGMA, DPA($\omega$6), DPA($\omega$3).

(Solvent of LC)
Acetic acid: Wako Pure Chemical Industries, Ltd
Methanol: Wako Pure Chemical Industries, Ltd
Acetonitrile: Wako Pure Chemical Industries, Ltd
(Establishment of at Once Quantitative Analysis System of PUFA Metabolites by MRM)
(MS/MS Measurement of Standard Compounds)

Compounds prepared as a standard were adjusted with a solution of methanol/milliQ/acetic acid=90/10/0.1 to about 1 $\mu$M, respectively, and MS/MS was measured with 4000Q-TRAP (Applied Biosystems) while about 150 $\mu$l was pumped at 10 $\mu$L/minute.

(Optimization of Cone Voltage and Collision Energy)

A MS/MS value characteristic in a structure of the compound was selected from measured MS/MS values, respectively, and measurement was performed by varying a cone voltage and a collision energy, thereby, the condition under which the MS/MS value was detected at the best sensitivity was determined.

(Study of Separation Condition by LC)

As a pump, HPLC (Waters) was used and, as a column, Acquity HPLC BEH $C_{18}$ 1.7 $\mu$m (1.0×150 mm) was used. A solvent was basically A liquid: milliQ/acetic acid=100/0.1, and B liquid: acetonitrile/methanol=4/1, a ratio and a flow rate were regulated every hour, and the condition under which a mixture of standard compounds was eluted at a good separation degree within 30 minutes was determined. Final LC condition is as follows:

For a solvent gradient, see FIG. 1B. Under this condition setting, regarding synthesized compounds (e.g., compounds synthesized with enzyme; 11,18-diHEPE and 17,18-diHEPE correspond thereto), a pair of a parent mass and a child mass of MRM can be optimized (optimization of collision energy) from measured values MS/MS. In addition, when a calibration curve is produced, quantitative analysis becomes possible. Regarding compounds which were not synthesized, MRM for the purpose of detection can be performed by setting the hypothetical condition.

Flow rate: 0 to 30 minutes→50 µL/minute.
30 to 33 minutes→80 µL/minute.
33 to 45 minutes→100 µL/minute.
(Production of Calibration Curve Using Standard Compounds)

Using standard compounds, a dilution series of 5 pg/10 µL to 1 ng/10 µL was prepared, and analysis was performed under the established LC condition and by a MRM program, and a calibration curve was produced. A height of a peak was adopted as a signal intensity.
(Results)
(Establishment of at Once Quantitative Analysis System of PUFA Metabolites by MRM)
(Establishment of at Once Analysis System of PUFA Metabolites)

Using standard compounds, a MRM channel specific for each compound was prepared. In addition, in the case of being no standard compound, such as a metabolite having an entirely novel structure, a channel was prepared hypothetically, with reference to a MS/MS value presumed from a structure, and a cone voltage and a collision energy of a metabolite having a similar structure. As a result of continuation of such work, at once analysis system of 100 or more kinds of metabolites was established by now (FIG. 1C). Regarding not only PUFA metabolites thought to be enzymatically produced, but also novel metabolites which had not previously been reported, 30 or more kinds were registered in a MRM program. In addition, almost all of these metabolites are position isomers of PUFA oxides, and have a common MS/MS value derived from dehydration and decarbonization. By using such a MS/MS value as a child mass value, a MRM channel for covering detection of monohydroxide, dihydroxide and trihydroxide of PUFA was also prepared.
(Study of Separation Condition of LC)

Then, the condition under which PUFA metabolites were separated well was studied. Since PUFA metabolites (oxides) are basically such that oxygen (hydroxyl group) is added to a variety of positions of a carbon chain of PUFA, and are structurally very similar, separation is difficult. When acetonitrile, methanol and water were mixed at a variety of amount ratios, and a flow rate was optimized, a system which separates PUFA metabolites very well in 45 minutes was established. A HEPE standard mixture was separated by LC, MRM analysis was performed, and a chromatogram of a channel specific for each metabolite is shown. For example, since 18-HEPE and 17,18-EpETE are the same in a fragment of structurally specific MS/MS, both of them are detected in one channel, but by establishing a system of LC having the high separation ability, each of them could be discriminated due to difference in a retention time.
(Production of Calibration Curve)

Using a MRM measuring method established in the present Example, a mixture of standard compounds was measured by varying an amount. As a result, a calibration curve having a high precision could be drawn in a range of 5 pg to 1 ng.

As described above, establishment of a high sensitivity at once quantitative analysis system of PUFA metabolites was successful.

Example 2

Analysis of Metabolism Route and Certification of Presence of Novel Compound

In the present Example, an 18-series EPA metabolism pathway was analyzed. Therein, it was found out that a novel compound which has not previously been found out in a living body is present.

Then, for the purpose of grasping what a metabolite is generated from 18-HEPE at inflammation, by amplification, incubation of 18-HEPE with lymphocyte which is infiltrating at an inflammation site was performed. A zymosan peritonitis model was used, in which many lymphocytes infiltrated at an inflammation site as PEC (Peritoneal Exudate Cells) and its recovery was easy. When peritonitis is elicited by zymosan administration, a pattern characteristic in acute inflammation is shown, in which first neutrophil infiltrates and, thereafter, this time monocyte • macrophage infiltrate with decrease in neutrophil. This time, using PEC after 4 hours from zymosan administration as an initial stage of inflammation, and after 48 hours as a later stage of inflammation, incubation with 18-HEPE was performed.
(Material and Method)
C57BL/6J mouse 8 to 10 weeks old, male: CLEA Japan, Inc.
12/15-LOX$^{-/-}$ mouse 8 to 10 weeks old, male: The Jackson Laboratory
Zymosan A: Wako Pure Chemical Industries, Ltd
Phosphate buffered physiological saline (PBS): 137 mM sodium chloride (NaCl), 2.7 mM potassium chloride (KCl), 10 mM hydrogen disodium phosphate ($Na_2HPO_4$), 2 mM dihydrogen potassium phosphate ($KH_2PO_4$); This was appropriately prepared.
Hanks' Balanced Salt Solution (HESS) (containing $Ca^{2+}$, $Mg^{2+}$): Gibco A23187:SIGMA: The solution was dissolved in dimethyl sulfoxide (DMSO) (Wako Pure Chemical Industries, Ltd), and stored as 2 mM at −20° C.
18-HEPE: Cayman.
(1. Incubation with PEC at Initial Stage and Later Stage of Inflammation)

Zymosan A was suspended in a physiological saline at 1 mg/mL, and the suspension was warmed at 37° C. for 30 minutes. This was intraperitoneally administered to a mouse at 1 mL. After 4 hours and 48 hours, the mouse was slaughtered, and 5 mL of PBS was injected into an abdominal cavity. After peritoneum was massaged 100 times, a total amount of an intra-abdominal fluid was recovered into a tube. After counting of cells, centrifugation was performed at 1200 rpm and 4° C. for 5 minutes, HBSS was added to cells (ppt), and 900 µL was transferred into a 50 mL tube ($5 \times 10^6$ cells/tube). The tube containing cells was pre-incubated at 37° C. and, during this, preparation of 18-HEPE and calcium ionophore A23187 was performed. 18-HEPE was first taken into a 1.5 mL tube, and a solvent was vaporized with nitrogen, to complete dryness. HBSS was added thereto, and this was ultrasound-treated to dissolve it (200 µM). A23187 was diluted with HBSS to 40 µM. Each 50 µL of the above-adjusted 18-HEPE and A23187 were added to the tube containing cells, and this was incubated at 37° C. for 30 minutes while a lid was opened partially (18-HEPE was 10 µM, A23187 was 2 µM final concentration). After 30 minutes, 2 mL of ice-cooled methanol was added, and this was vortex-treated and was allowed to stand at −20° C. for 1 hour or longer. A fraction of a fatty acid metabolite was prepared by solid phase extraction, and analysis by MRM was performed.
(Results)
(1. Incubation with PEC at Initial Stage and Later Stage of Inflammation)

Figures 1, 2A:
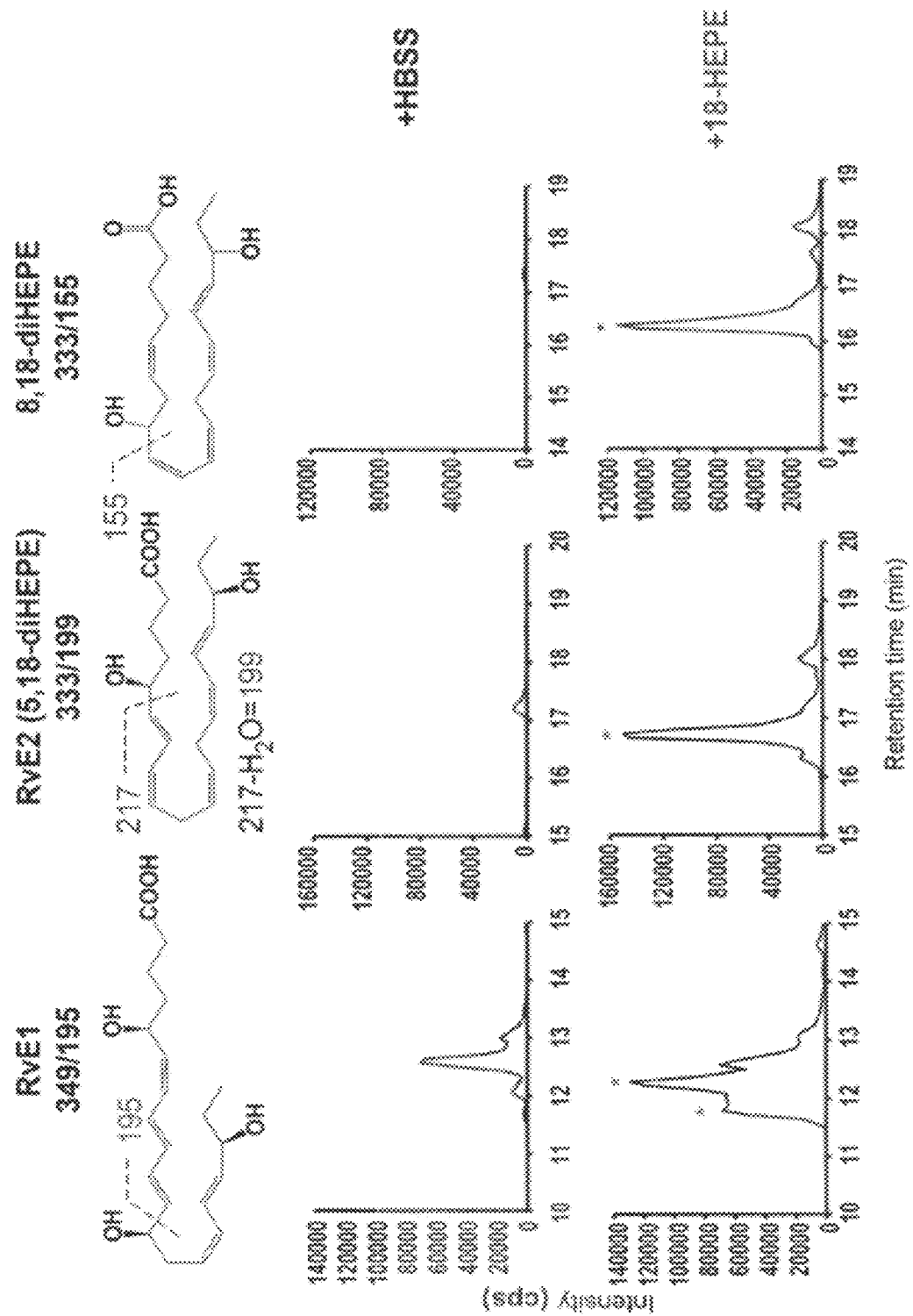
FIG. 2A-1 shows incubation of peritoneal exudate cells (PEC) at an inflammation early stage (after 4 hours) with 18-hydroxy eicosapentaenoic acid (HEPE). An asterisk indicates a peak of a metabolite including respective isomers. From the left side, an asterisk indicates Resolvin E1, Resolvin E2, and 8,18-dihydroxy eicosapentaenoic acid (diHEPE) in this order.
Figures 2, 2A:
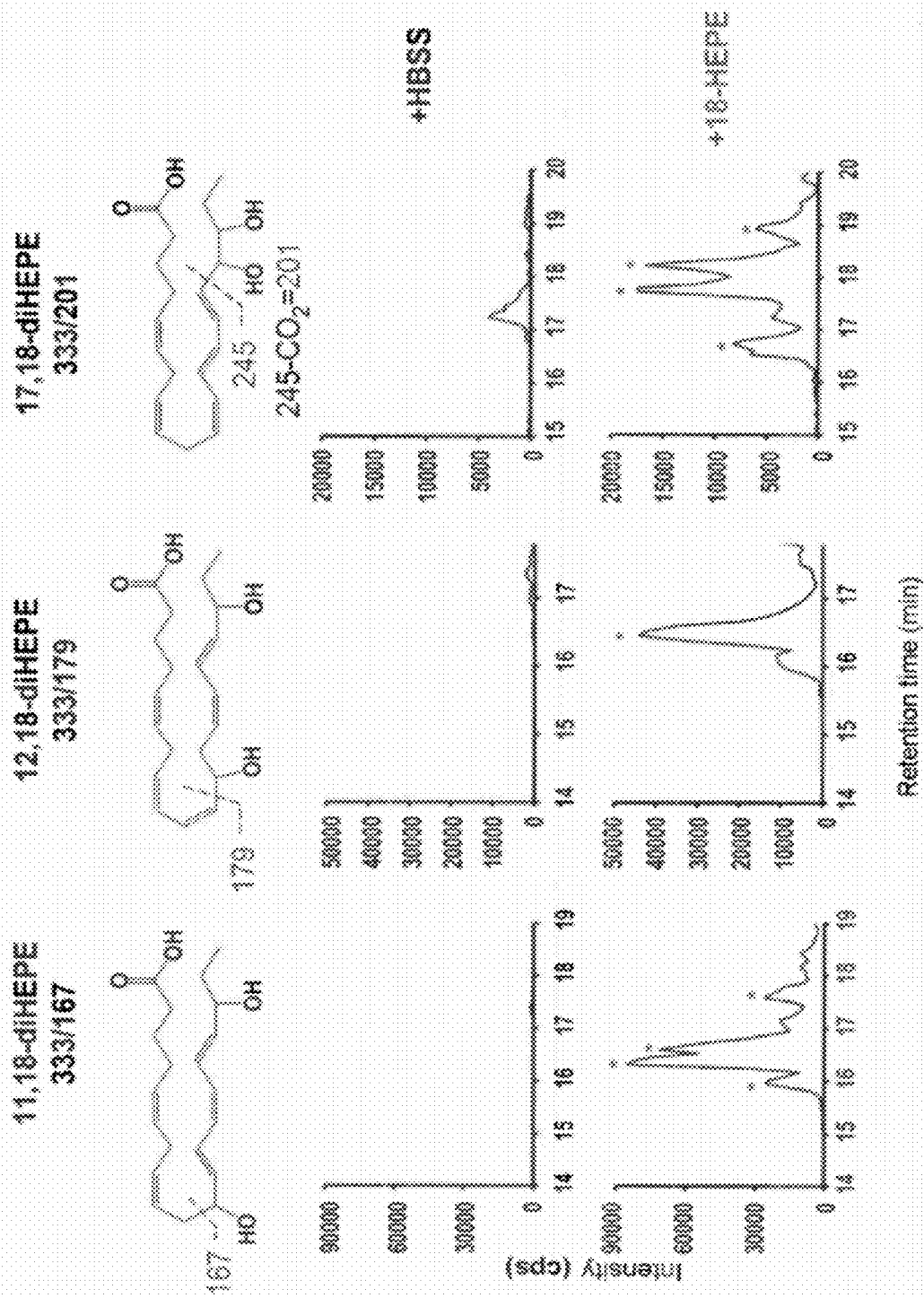

18-HEPE was incubated with PEC, and analysis by MRM was performed. As a result, in addition to RvE1 and RvE2 known as an anti-inflammatory mediator, 18-HEPE-dependant peaks were recognized in some MRM channels (FIG. 2A). These peaks were thought to be 8,18-diHEPE, 11,18-diHEPE, 12,18-diHEPE, and 17,18-diHEPE, respectively, from the MRM channel, and from that they were 18-HEPE-dependently recognized. A plurality of peaks are recognized regarding some channels, and it is thought to be due to difference in coordination of a double bond (cis, trans), and difference in steric configuration of a hydroxyl group (S body, R body).

Figures 2, 2B:
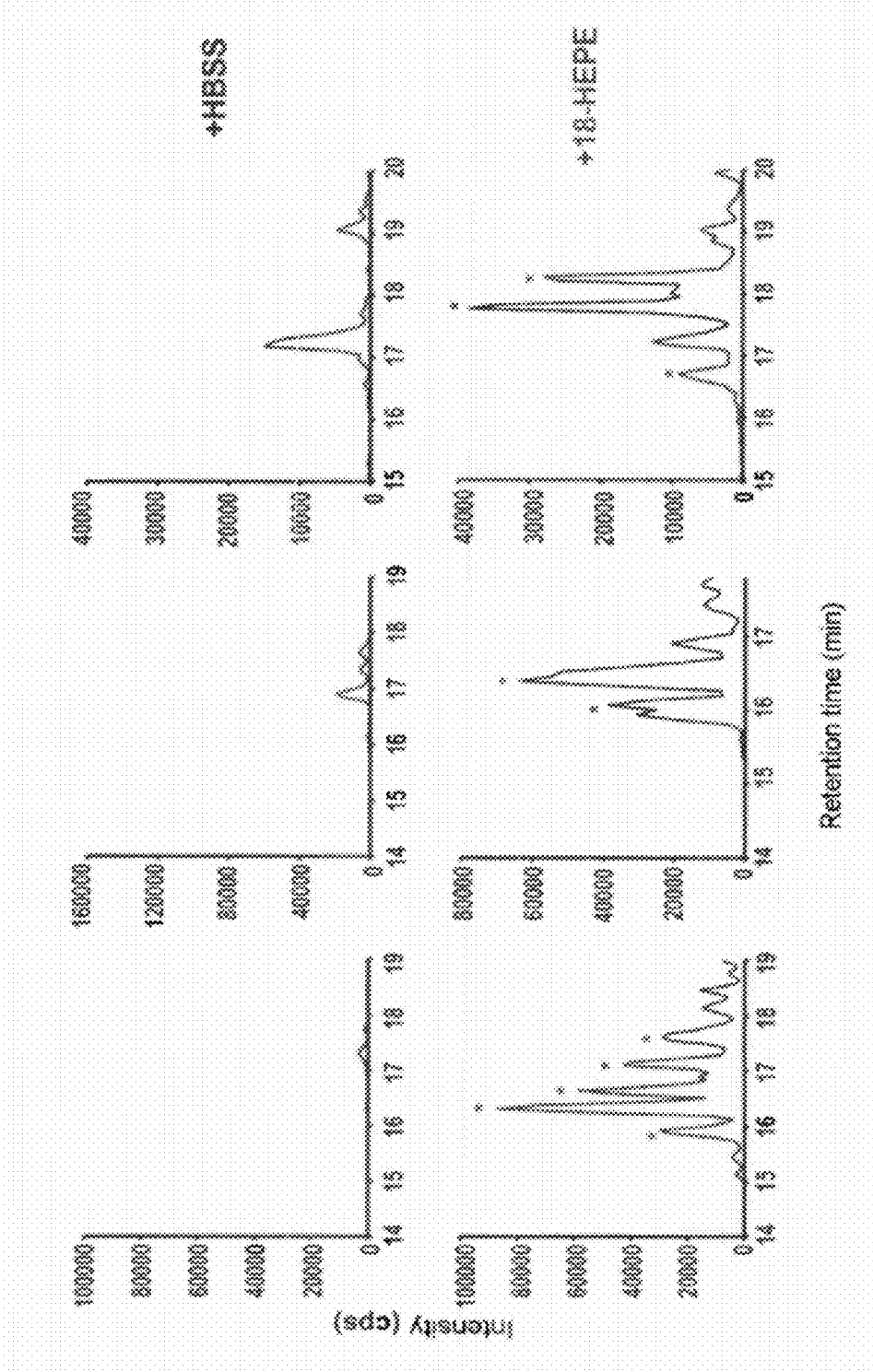
Figure 2C:
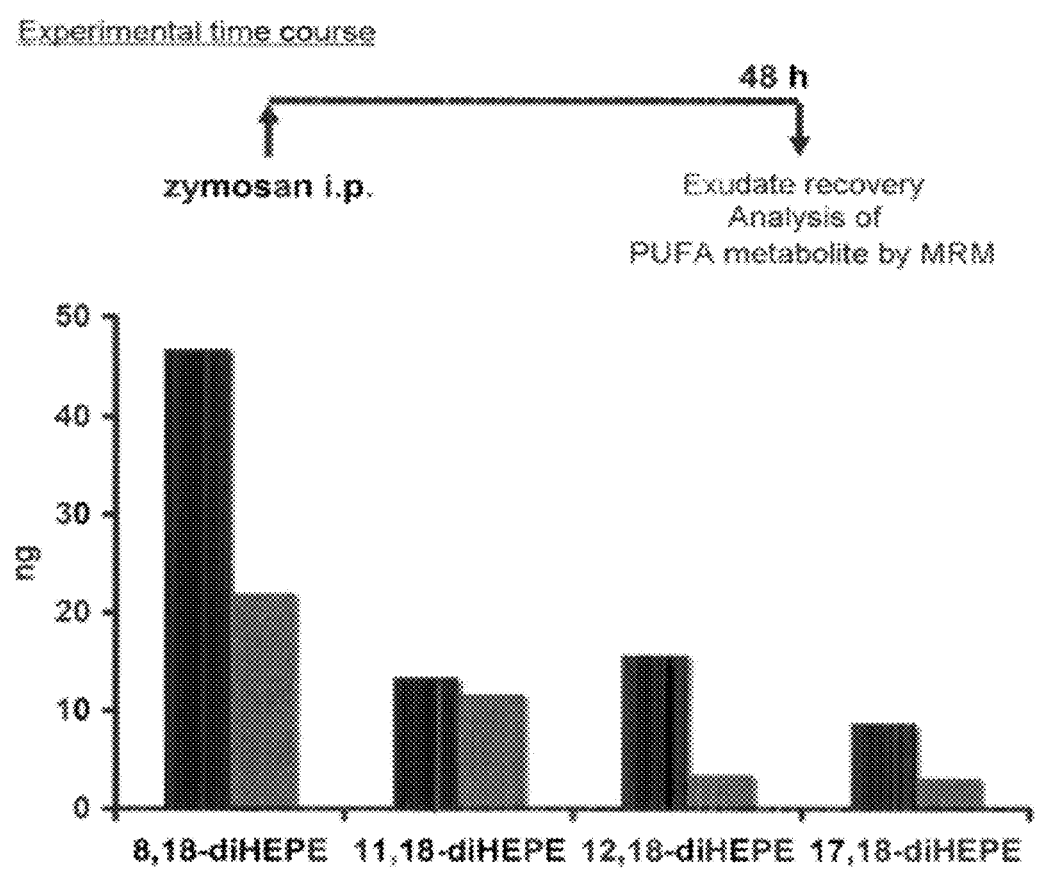
FIG. 2C shows the quantitation of a metabolite generated by incubation of PEC after 48 hours from inflammatory induction with 18-HEPE, which is performed using wild-type and $12/15\text{-LOX}^{-/-}$ mice. The left side black column shows the results in a wild-type mouse, and the right side gray column shows the results in a $12/15\text{-LOX}^{-/-}$ mouse.

In addition, although a tendency that RvE1 and RvE2 were produced at a large amount in incubation with PEC at an inflammation initial stage was recognized, there was a tendency that 12,18-diHEPE and 17,18-diHEPE were more in incubation with PEC at an inflammation later stage (FIG. 2B). Although it was made apparent that RvE1 and RvE2 are generated by acting 5-LOX on 18-HEPE (Non-Patent Literatures 3,4), there is no report that other metabolites are produced. In addition, 5-LOX and 12/15-LOX are thought in lipoxygenase present in PEC of a mouse. Then, when similar incubation with PEC was performed for 48 hours of inflammation inducement using a 12/15-LOX$^{-/-}$ mouse for the purpose of revealing an enzyme producing these novel metabolites, 8,18-, 12,18-, and 17,18-diHEPE were remarkably decreased in a 12/15-LOX$^{-/-}$ mouse (FIG. 2C). That is, it was suggested that those metabolites are produced by 12/15-LOX. It is thought that 11,18-diHEPE is produced by other enzyme. A reaction mechanism of an enzymatic reaction which is thought at this time is shown in FIGS. 2F to G. It is thought that since 12/15-LOX has activity of extracting hydrogen from carbon at a 10-position and a 13-position of EPA, it produces a novel metabolite of the present invention.

(a. Isolation of Eosinophil).

Zymosan A (Wako Pure Chemical Industries, Ltd.) was suspended in a physiological saline at a concentration of 1 mg/mL, and the suspension was warmed at 37° C. for 30 minutes. This zymosan A suspension (1 mL) was intraperitoneally administered to a C57BL/6J mouse (wild-type; 8 to 10 weeks old, female; Japan SLC, Inc.). After 48 hours, cells which had exuded into an abdominal cavity were recovered, and the cell number was counted. Centrifugation was performed at 1200 rpm and 4° C. for 5 minutes and the supernatant (exudate) was stored at −20° C. A precipitate (cells) was suspended in PBS, the suspension was passed through a 70 µm and 38 µm mesh, and an eosinophil population was selected by FACS Aria (BD Biosciences).

(b. Incubation of 18-HEPE or 20-HDoHE with Eosinophil).

18-HEPE (Cayman) or 20-HDoHE (Cayman) was taken into a 1.5 mL tube, a solvent was vaporized with nitrogen, and this was dissolved in HESS (containing $Ca^{2+}$, $Mg^{2+}$; Gibco) (100 µM). In addition, a solution of 2 mM calcium ionophore A23187 (SIGMA) in DMSO (Wako Pure Chemical Industries, Ltd.) was diluted with HESS (20 µM). Eosinophil derived from a wild-type mouse was diluted with HESS to $1.25\times10^6$ cells/mL, and this was placed into a 50 mL tube ($5\times10^5$ cells/tube). To this tube were added the above-prepared 18-HEPE or 20-HDoHE (both final concentration 10 µM) and A23187 (final concentration 2 µM), and the mixture was warmed at 37° C. for 30 minutes. To this tube was added a 2-fold volume of ice-cooled methanol (Wako Pure Chemical Industries, Ltd.) and this was vortexed, and stored at −20° C.

(c. Preparation of Fraction of Fatty Acid Metabolite by Solid Phase Extraction)

When a sample contains 10% or more of methanol, milliQ water was added so that a methanol content was less than 10% v/v. 1N hydrochloric acid (Wako Pure Chemistry Industries, Ltd.) was added to a sample to adjust a pH to about 3. Then, 1 ng of $LTB_4$-6,7,14,15-$d_4$ (Biomol) was added. Sep-pak $C_{18}$-cartridge (500 mg; manufactured by Waters) was mounted on a column stand equipped with a vacuum pump (Waters), 20 mL of methanol, and 20 mL of milliQ water were flown in this order to equilibrate a column. Then, the sample was flown, and washed with 20 mL of milliQ water. Thereafter, 10 mL of hexane (Wako Pure Chemical Industries, Ltd.) was flown to elute a neutral fat, then, 10 mL of methyl formate (Wako Pure Chemical Industries, Ltd.) was flown to elute a fat metabolite, and this fraction was recovered. A solvent was vaporized with nitrogen and this was dissolved in methanol.

(d. Analysis of Fat by Multiple Reaction Monitoring (MRM))

MRM is a measuring procedure of detecting specifically a compound from a combination of a MS value of a compound (Q1) and a MS/MS value characteristic in a structure (Q3). Metabolites derived from 18-HEPE identified in the present specification are such that MS values upon measurement in a negative ion mode are all equal, being 333 in which one oxygen is added to 18-HEPE, but structure-specific MS/MS values are different depending on a position at which oxygen is added. Channels for detecting each metabolite (Q1/Q3) were RvE1=(349/195), RvE2=(333/195), 8,18-diHEPE=(333/155), 11,18-diHEPE=(333/167), 12,18-diHEPE=(333/179), and 17,18-diHEPE=(333/201). In addition, regarding DHA metabolites, channels were 10,20-diHDoHE=(359/153), 13,20-diHDoHE=(359/193), 14,20-diHDoHE=(359/205), and 19,20-diHDoHE=(359/227). Further, this MRM was combined with LC to produce a chromatogram of each channel. As a measuring instrument, 4000Q-TRAP (Applied Biosystems) was used and, as a pump, HPLC (Waters) was used. The sample was finally dissolved in 30 µL of milliQ water/methanol=40/60, and 10 µL of it was used for measurement. LC condition was as follows:

(Composition of Mobile Phase)
A liquid: milliQ water/acetic acid=100/0.1
B liquid: acetonitrile/methanol=4/1
0 to 5 minutes A liquid 27%;
5 to 15 minutes A liquid 27%→70%;
15 to 25 minutes A liquid 70%→80%;
25 to 35 minutes A liquid 80%→100%;
35 to 45 minutes A liquid 100%
• Flow rate
0 to 30 minutes 50 µL/minute;
30 to 33 minutes 80 µL/minute;
33 to 45 minutes 100 µL/minute.
(Column)
X bridge $C_{18}$ 5.0 µm, 4.6 mm×100 mm (Waters).

Figure 2E:
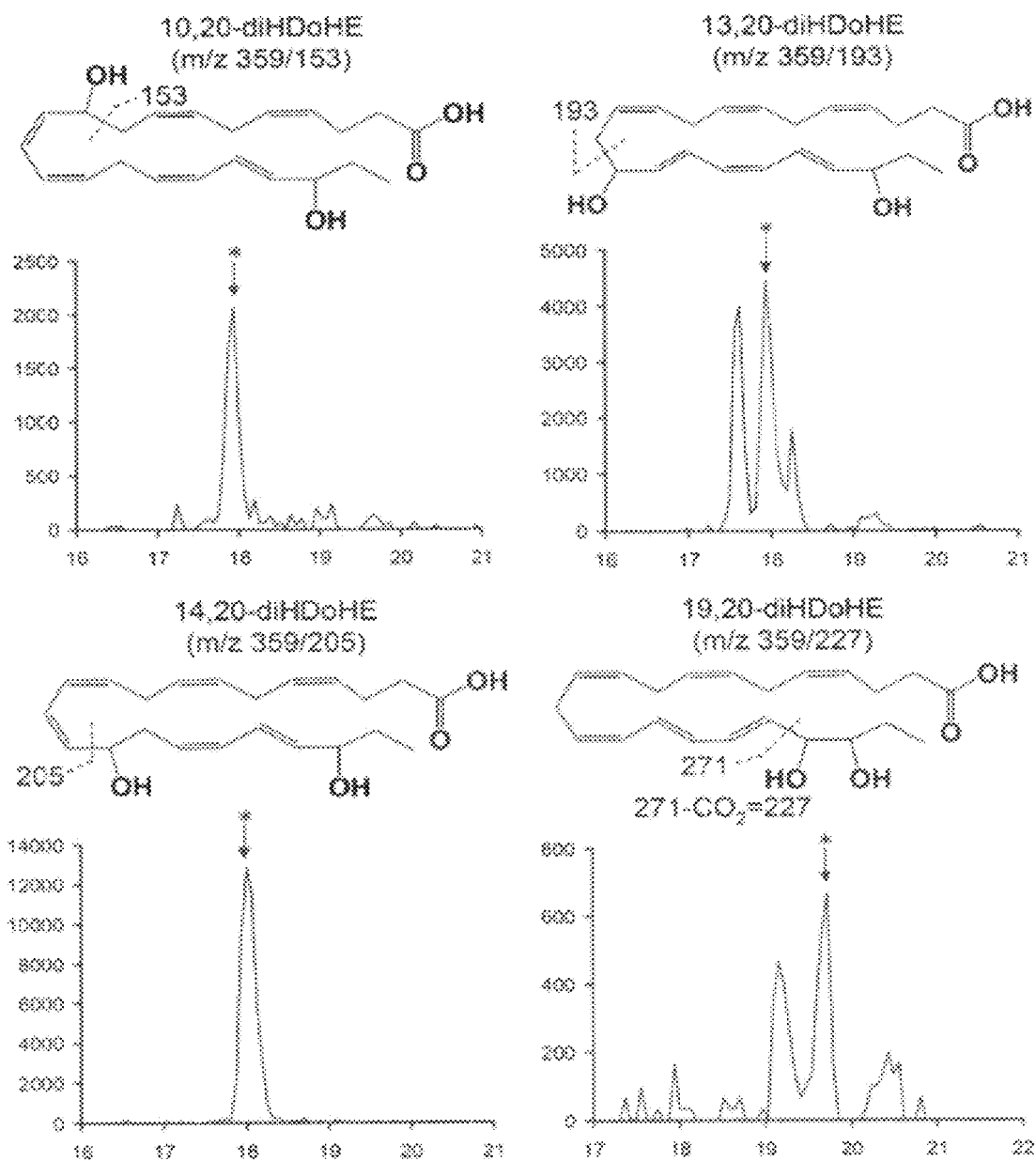
FIG. 2E shows the analysis result and relative quantitation of each metabolite generated as the result of incubation of 20-HDoHE with eosinophil. An asterisk indicates a peak of each main metabolite. From the left upper side to the right upper side, an asterisk indicates 10,20-diHDoHE, and 13,20-diHDoHE in this order and, from the left lower side to the right lower side, an asterisk indicates 14,20-diHDoHE and 19,20-diDoHE in this order.
Figure 2F:
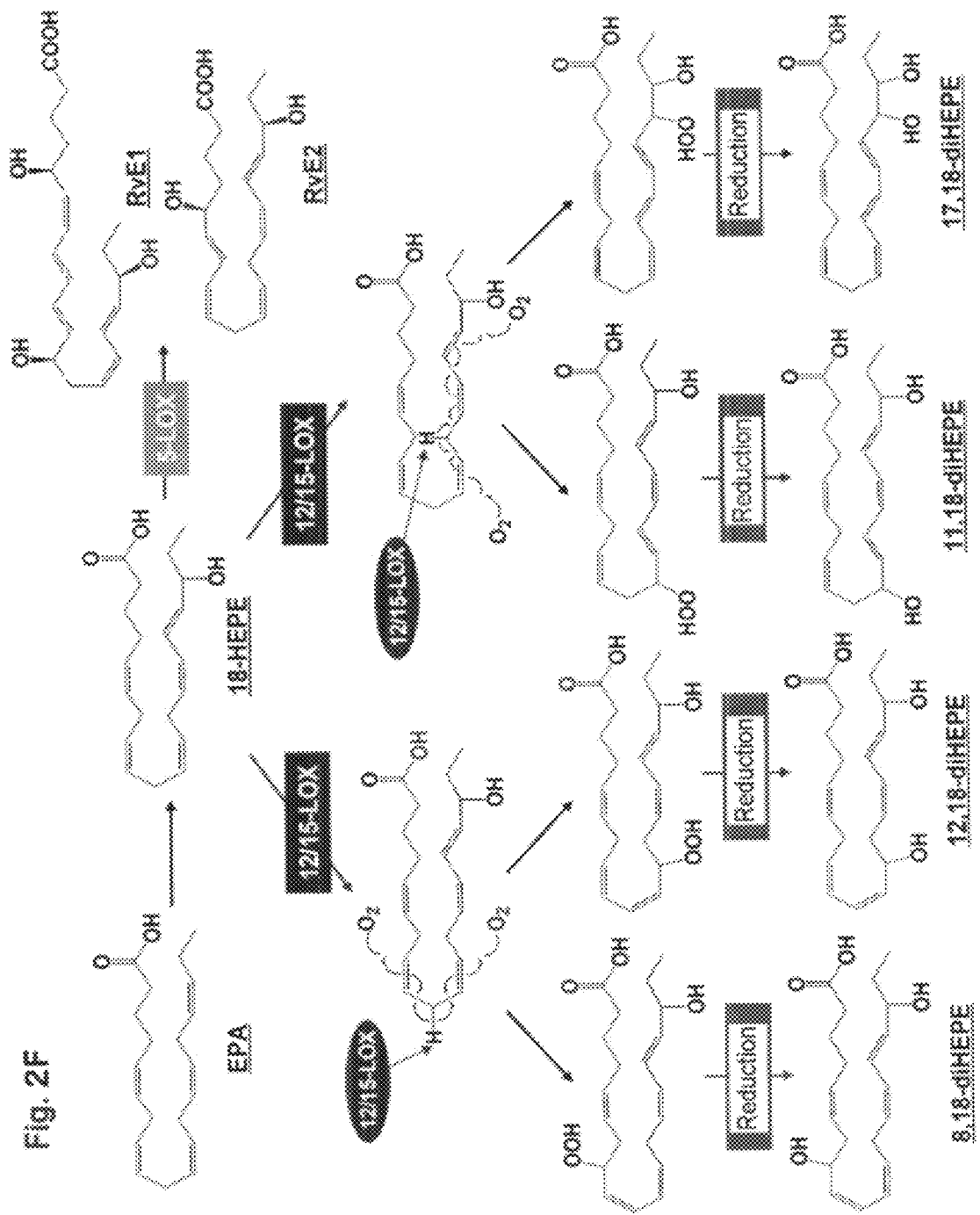
FIG. 2F shows a metabolism route using 18-HEPE which is a metabolite of eicosapentaenoic acid (EPA) as an origin.

As a result of comprehensive metabolome analysis of 18-HEPE metabolites and 20-HDoHE metabolites by MRM, it was made clear that, from 18-HEPE, in addition to the known metabolites such as RvE1 and RvE2, at least 4 novel metabolites (8,18-diHEPE, 11,18-diHEPE, 12,18-diHEPE and 17,18-diHEPE) were produced (FIG. 2D) and, from 20-HDoHE, 10,20-diHDoHE, 13,20-diHDoHE, 14,20-diHDoHE and 19,20-diHDoHE were produced (FIG. 2E). It is known that RvE1, RvE2 and 10,20-diHDoHE are produced by 5-LOX which is mainly highly expressed in eosinophil, while it was made clear that all of four 18-HEPE-derived novel metabolites (8,18-diHEPE, 11,18-diHEPE, 12,18-diHEPE and 17,18-diHEPE) identified in the present specification, as well as 13,20-diHDoHE, 14,20-diHDoHE and 19,20-diHDoHE are produced by enzymes other than 5-LOX (FIGS. 2F and 2G).

Therefore, in the present Example, it was made clear that novel compound of the present invention is produced by eosinophil.

Example 3

Synthesis of 18-HEPE-Derived Metabolites

In the present invention, it was demonstrated that novel compounds corresponding to novel metabolites derived from 18-HEPE and 20-HDoPE can be synthesized. It was found out that these are produced by 12/15-LOX or soybean LOX (sLOX), as a result of intensive study. Then, in order to assess activity of these metabolites, those metabolites were tried to synthesize using an enzymatic reaction therefor. In the present Example, an enzymatic reaction was performed using sLOX for the purpose of subjecting to general use, in place of mouse 12/15-LOX. In addition, whether produced metabolites were constituent with those produced by a living body was examined by a spike experiment.

(Material)

(1. Preparation of Dihydroxy Body of DHA by Enzymatic Reaction)

Enzymatic reaction using soybean lipoxygenase (sLOX)
Borate buffer (pH 9.0): Boric acid and potassium chloride (both Wako Pure Chemical Industries, Ltd.) were dissolved in milliQ. A 1N potassium hydroxide (Wako Pure Chemical Industries, Ltd.) solution was added to set a pH at 9.0 and, thereafter, boric acid and potassium chloride were diluted with milliQ to 50 mM.
Soybean lipoxygenase (sLOX): SIGMA
Sodium tetrahydroborate: Wako Pure Chemical Industries, Ltd.
DHA: SIGMA: Stored at $-20°$ C. as 100 mg/mL methanol (Wako Pure Chemical Industries, Ltd.) solution.

(2. Preparation of Fatty Acid Metabolite Fraction by Solid Phase Extraction)

Sep-pak$C_{18}$Cartridge (500 mg): Waters
Methanol: Wako Pure Chemical Industries, Ltd.
Methyl formate: Wako Pure Chemical Industries, Ltd.
Hexane: Wako Pure Chemical Industries, Ltd.
Hydrochloric acid: Wako Pure Chemical Industries, Ltd.: Diluted with milliQ to 1N, and stored at room temperature.
pH test paper: MACHEREY-NAGEL
Diluted in ethanol (Wako Pure Chemical Industries, Ltd.) to 100 pg/µL, and stored at $-20°$ C.

(3. Purification of Compound Using Reverse Phase HPLC)

Methanol: Wako Pure Chemical Industries, Ltd.
Acetic acid (Wako Pure Chemical Industries, Ltd.) was added to 0.01% v/v acetic acid: milliQ (pure water) to 0.01% v/v.

(4. Spike Experiment with Biological Sample)

Compound synthesized and purified in the present Example
Sample for incubation of 18-HEPE with PEC at an inflammation later stage (after 48 hours)

(Method)

(a. Synthesis by Enzymatic Reaction)

18-HEPE (Cayman) (300 µg) was taken into an eggplant flask, a solvent was vaporized with nitrogen, and 9 mL of a borate buffer (50 mM of each of boric acid and potassium chloride, pH 9.0) was added thereto to dissolve it. Soybean lipoxygenase (SIGMA) (1 mg) was added thereto to progress an enzymatic reaction and, thereafter, a reducing reaction was performed using NaBH$_4$ (Wako Pure Chemical Industries, Ltd.). Thereafter, a fraction of a fatty acid metabolite was prepared by solid phase extraction.

(b. Separation and Purification of Compound by Reverse Phase HPLC)

A solvent of the fraction of a fatty acid metabolite prepared as described above was vaporized with nitrogen, and was dissolved in an initial mobile phase (H$_2$O/MeOH/acetic acid=35/65/0.01) of HPLC. This was subjected to HPLC (Agilent Technologies), and peaks were fractionated into glass small test tubes. A solvent was vaporized with nitrogen to dryness, and a sample was finally stored as an ethanol solution at $-20°$ C. The condition of reverse phase HPLC was as follows:

Composition of Mobile Phase
A liquid: methanol
B liquid: milliQ water/acetic acid=100/0.01
0 to 21 minutes A65%
21 to 35 minutes A100%
Column
X bridge C$_{18}$ 5.0 µm, 4.6 mm×100 mm (Waters)
Flow Rate
0.7 mL/minute.

(Results)

Figure 3A:
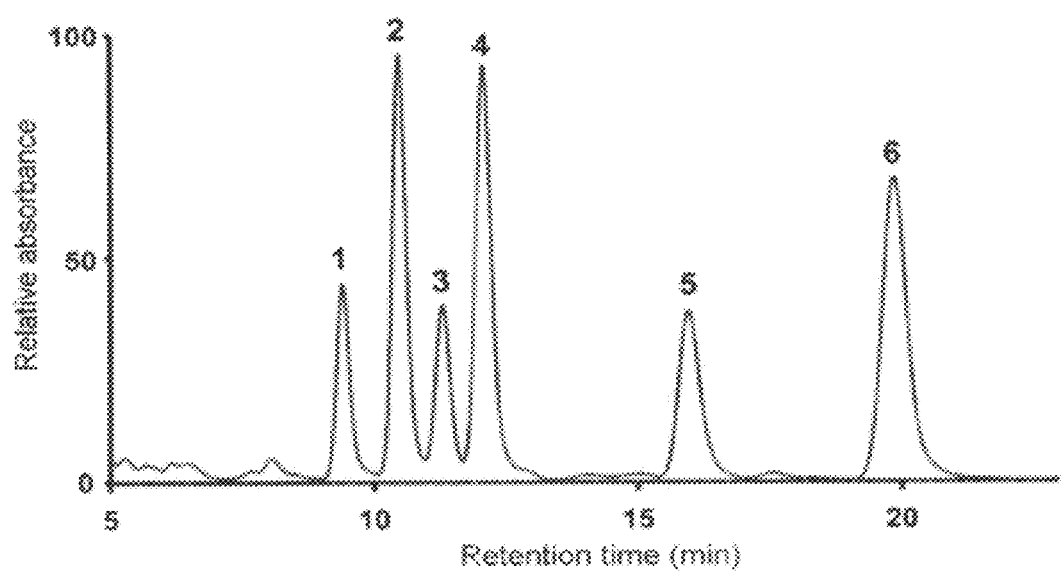
FIG. 3A is the result of reverse phase HPLC chromatogram (light absorption chromatogram at 270 nm) showing the result of incubation of 18-HEPE with sLOX, and the purification of the sample by reverse phase high performance liquid chromatography (HPLC).
Figure 3C:
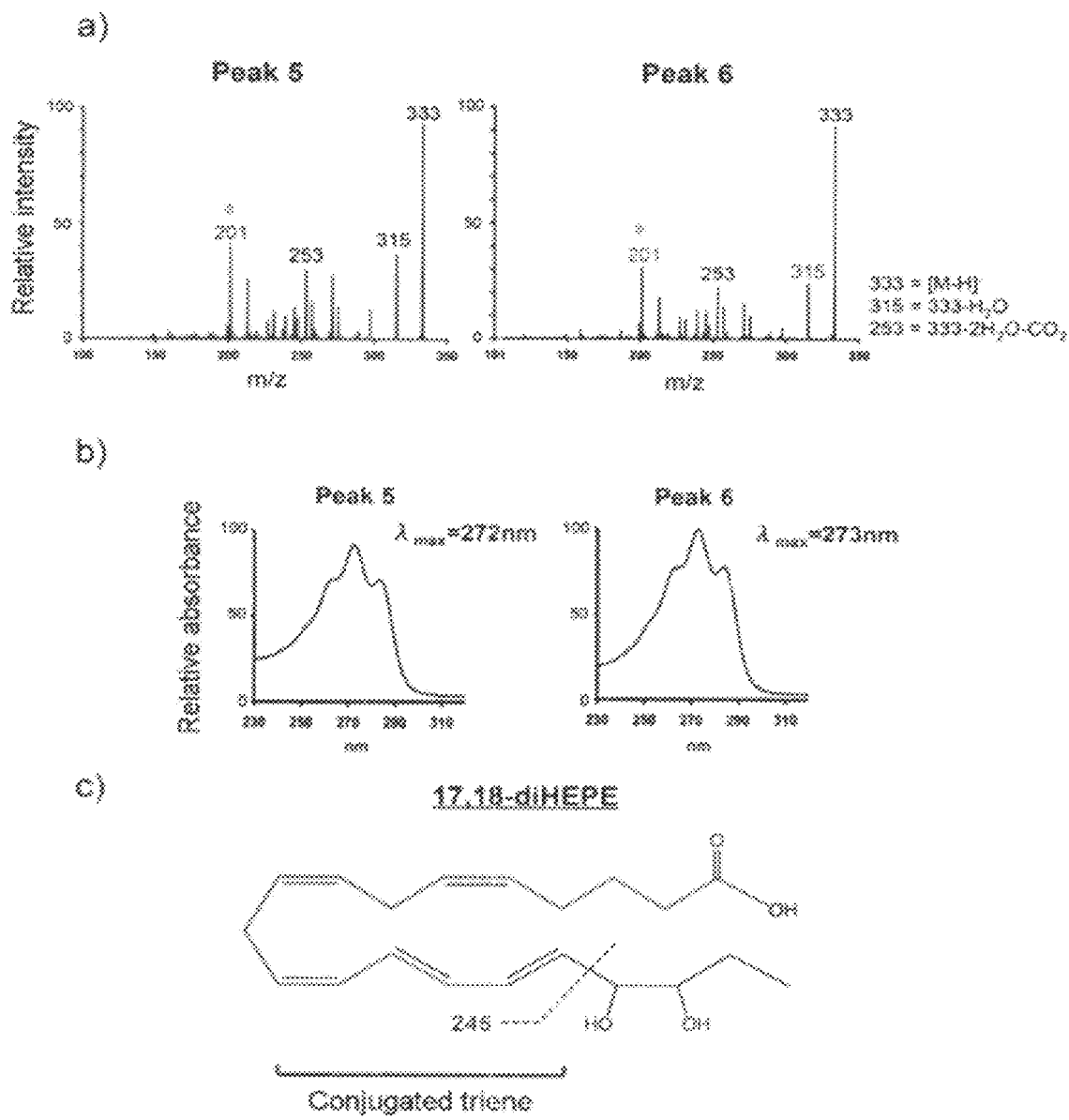
FIG. 3C shows (a) mass spectroscopy (MS/MS) and (b) light absorption spectrum of peaks 5 and 6 of Example 3, and (c) structure of 17,18-diHEPE.

When 18-HEPE and sLOX were reacted, and the reaction products were purified by reverse phase HPLC, six peaks were generated (FIG. 3A). Then, when all of the six were fractionated and measured by MS/MS, a mass value (167) of a fragment generated by addition of oxygen to a 11-position was recognized in peaks 1 to 4, and as a result of measurement of an absorption spectrum, a trimodal spectrum having $\lambda_{max}$ at around 270 nm characteristic when three double bonds were conjugated (triene) was recognized, and thus those peaks were thought to be 11,18-diHEPE (FIG. 3B). In addition, since a mass value (201) of a fragment generated by addition of oxygen to a 17-position was recognized in peaks 5 and 6, and similarly a spectrum characteristic in triene was recognized, those peaks were thought to be 17,18-diHEPE (FIG. 3C). A plurality of peaks were recognized, respectively, but since this is derived from cis or trans of a double bond, and 18-HEPE as a substrate is racemic, it is thought that they are thought to be derived from an enantiomer.

In incubation with lymphocyte, 8,18-, 12,18-, and 17,18-diHEPE were generated 12/15-LOX-dependently, but in a reaction using sLOX, 11,18-, and 17,18-diHEPE were generated. It is thought that this difference is probably due to difference in a nature of an enzyme, such as that 12-LOX activity is present in mouse 12/15-LOX, but only 15-LOX activity is present in sLOX.

Figure 3D:
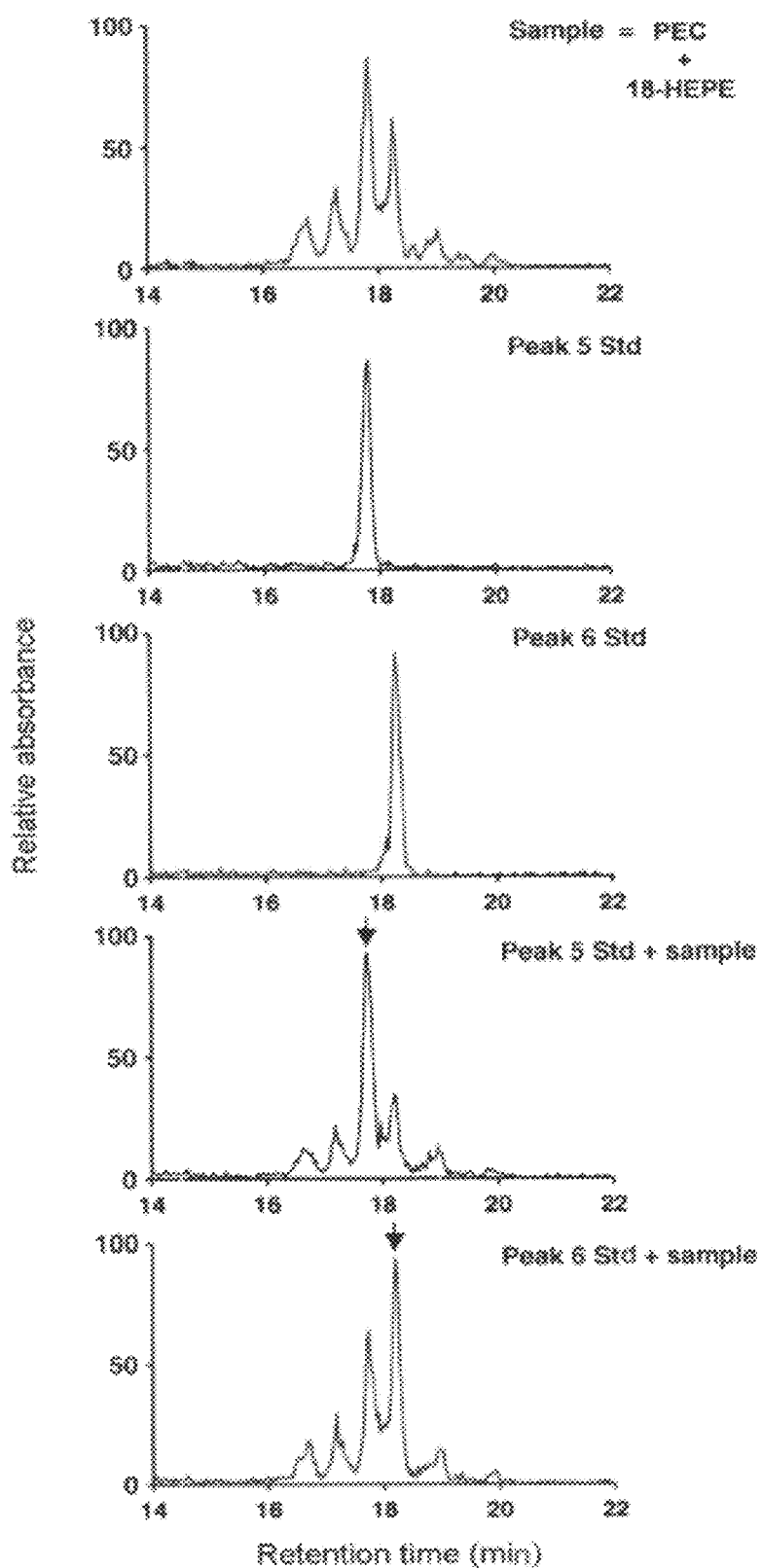
FIG. 3D shows the results of a spike experiment of a sample (biological sample; sample) obtained by incubation of PEC after 48 hours from peritonitis induction with 18-HEPE, with peaks 5 and 6 which are 17,18-diHEPE. From the upper side, reverse phase HPLC chromatograms of only sample, only peak 5, only peak 6, peak 5 and sample, and peak 6 and sample are shown in this order. As shown with an arrow, peak 5 and peak 6 are consistent with two measured peaks of a channel for specifically detecting 17,18-diHEPE among the biological samples.

In addition, when of the resulting compounds, regarding peaks 5 and 6 which are 17,18-diHEPE, a spike experiment with a biological sample (sample from incubation of PEC after 48 h from peritonitis inducement with 18-HEPE) was performed, these peaks were consistent with two major peaks of a channel for specifically detecting 17,18-diHEPE (FIG. 3D). It is thought that two isoforms of 17,18-diHEPE obtained by the enzymatic reaction are the same as those produced by a living body. It is expected that 11,18-diHEPE is similarly synthesized.

Example 4

Assessment of Physiological Activity of 18-HEPE-Derived Metabolites

In the present Example, physiological activity in a peritonitis model of the compound synthesized in Example 1 was assessed, and whether there was anti-inflammatory activity or not was assessed.

(Material)

(1. Inducement of Zymosan Peritonitis)

Mouse C57BL/6J 7 weeks old, male: CLEA Japan, Inc.
Physiological saline: Otsuka Pharmaceutical Co., Ltd.
Zymosan A: Wako Pure Chemical Industries, Ltd.
Phosphate buffered physiological saline (PBS)

(2. Three-Color Staining of FACS (CD11b, Gr-1, F4/80))

Anti-mouse CD16/CD32 (0.5 mg/mL): BDBiosciences
FITC anti-mouse F4/80 (0.5 mg/mL): eBiosciences PE anti-mouse Ly-6G & Ly-6C (Gr-1) (0.2 mg/mL): eBiosciences
PerCP-Cy5.5 anti-mouse CD11b (Mac-1) (0.2 mg/mL): eBiosciences
Staining Antibody Mix
1.0 μL/sample of FITC anti-mouse F4/80
0.5 μL/sample of PE anti-mouse Ly-6G & Ly-6C
0.5 μL/sample of PerCP-Cy5.5 anti-mouse CD11b
The antibodies are diluted in 50 μL/sample PBS. Preparation at use.
PBS: same as Example 2.
(3. Assessment Using Acute Lung Damage Model)
Mouse C57BL/6J 7 weeks old, male: CLEA Japan, Inc.
Hydrochloric acid: SIGMA
Nembutal: Dainippon Sumitomo Pharma Co., Ltd.
Ketamine: Daiichi Sankyo Propharma
Xylazine: Bayer Medical Ltd.
PBS: Appropriately prepared as in Example 2
Physiological saline: Otsuka Pharmaceutical Co., Ltd.
Simple Giemsa staining solution Diffquick: Sysmex Corporation
(Method)
(a. Assessment Using Zymosan Peritonitis Model)

For an inflammation model, zymosan peritonitis elicited by intraperitoneally administering zymosan being a cell wall component of yeast was used. Since an exudate in an abdominal cavity can be recovered, the present model is a model suitable for analyzing cytokines and eicosanoids.

Zymosan A (Wako Pure Chemical Industries, Ltd.) was suspended in a physiological saline to 1 mg/mL, and the suspension was warmed at 37° C. for 30 minutes. Thereafter, this zymosan A solution was vortexed, and returned to room temperature. The compound synthesized in the previous Example, 17,18-diHEPE was taken into a 1.5 mL tube, and a solvent was vaporized with nitrogen to complete dryness and, thereafter, a physiological saline was added to dissolve it. Then, 100 μL of this compound solution was injected (1 ng or 10 ng/mouse) through a tail vein of C57BL/6J mouse (7 weeks old, mail: CLEA Japan, Inc.). As a control, a group in which only a physiological saline was injected, and a group in which dexamethasone (10 μg/mouse) being an anti-inflammatory steroid was injected, were used. After about 2 minutes, 1 mL of a zymosan A solution was intraperitoneally administered. After 2 hours, cells exuded into an abdominal cavity were recovered into a tube with a PBS, and the cell number was counted. Thereafter, this tube was centrifuged at 1200 rpm and 4° C. for 5 minutes to remove the supernatant, a precipitate (pellet) was suspended in PBS, and a population was analyzed by three-color staining of FACS.

(b. Three-Color Staining of FACS)

Abdominal cavity cells were adjusted to $2.5 \times 10^6$ cells/mL, and 200 μL was placed into a 5 mL round-bottom tube (BD-Falcon) ($5 \times 10^5$ cells/tube). To this tube was added an anti-mouse CD16/CD32 antibody (0.5 mg/mL; BDBiosciences) at 1 μL per tube, and this was incubated at room temperature for 10 minutes. To this tube was added a staining antibody mix (prepared by diluting 1.0 μL of FITC bound anti-mouse F4/80 antibody (0.5 mg/mL; eBiosciences), 0.5 μL of PE bound anti-mouse Ly-6G & Ly-6C antibody (0.2 mg/mL; eBiosciences) and 0.5 μL of PerCP-Cy5.5 bound anti-mouse CD11b antibody (0.2 mg/mL; eBiosciences) in 50 μL of PBS, per sample) at 50 μL/tube, and this was incubated at room temperature for 15 minutes under light shielding. Measurement was performed by FACS Calibur (BDBiosciences).

Figure 4A:
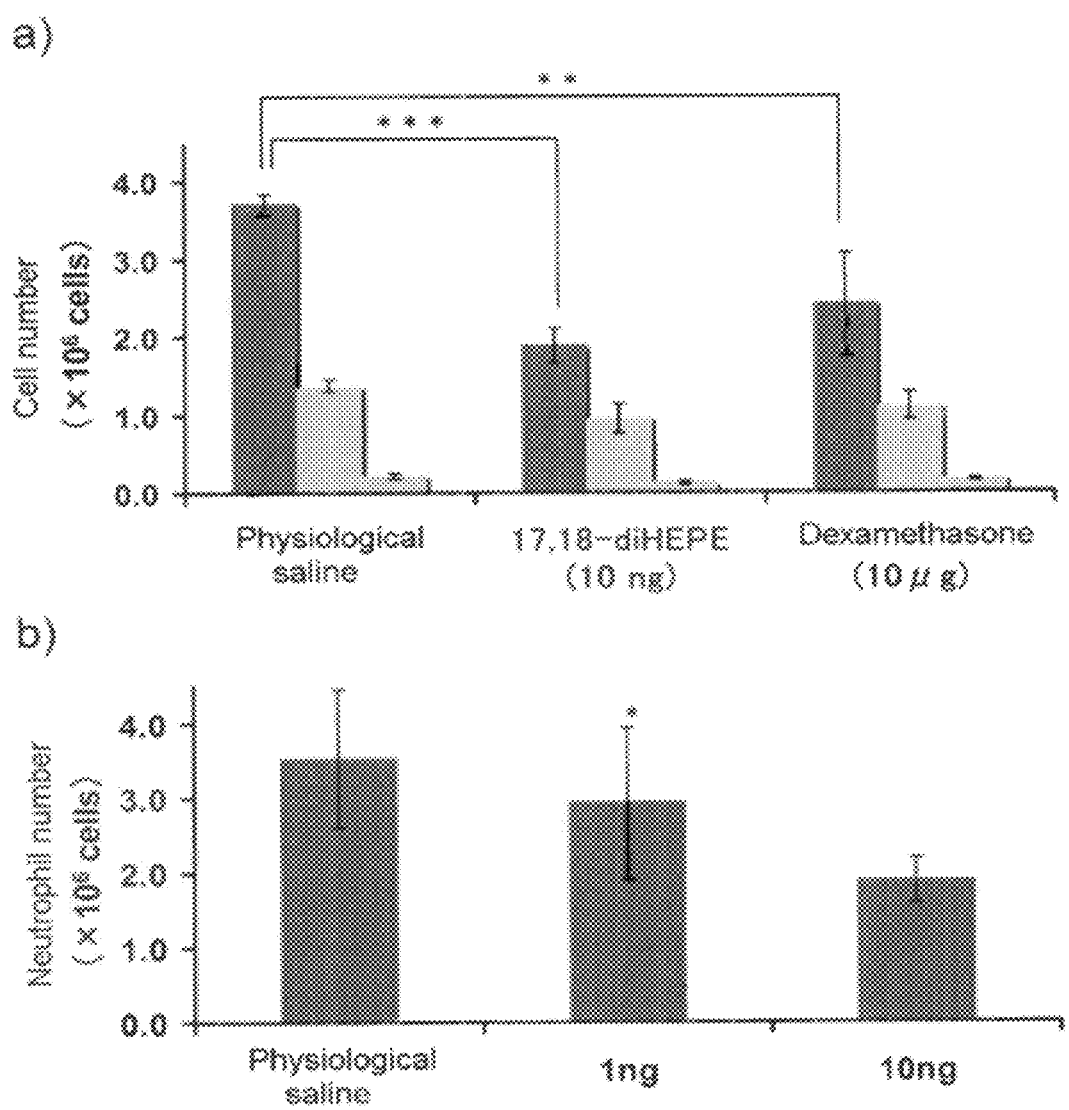
FIG. 4A shows assessment of physiological activity of an 18-HEPE-derived metabolite (17,18-diHEPE) in a zymosan peritonitis model. In (a), from the left side, physiological saline (control), 10 ng of 17,18-diHEPE, and 10 μg of dexamethasone are injected into a mouse tail vein, respectively, and 1 mg of zymosan is intraperitoneally administered after 5 minutes to initiate peritonitis. After 2 hours, intraperitoneal cells are recovered, and the number of PMN (neutrophil) (column at the left end regarding each group), the number of lymphocyte (central column regarding each group) and the number of macrophage (column at the right end regarding each group) are analyzed using FACS, respectively, and the results are shown. The average of three times experiments is taken, respectively, and the value is shown as an average±SEM.  represents p<0.01 for physiological saline, and * represents p<0.001 for physiological saline. In (b), this shows that activity of 17,18-diHEPE in a peritonitis model is dose-dependent. The results are shown as an average+SD, and * represents p<0.05 for physiological saline.

As a result, 17,18-diHEPE suppressed about 40% of infiltration of neutrophil at an extremely low dose of 10 ng/mouse (FIG. 4A). This neutrophil suppressing activity was almost equal to 10 μg/mouse of dexamethasone used as a control.

(c. Analysis Using Acute Lung Damage Model)

One hundred μL of a compound 17,18-diHEPE dissolved in a physiological saline was injected through a tail vein of a C57BL/6J mouse (7 weeks old, male; CLEA Japan, Inc.). After 15 minutes, this mouse was anesthetized by intraperitoneally administering a mixed solution of ketamine (Daiichi Sankyo Propharma) and xylazine (Bayer Medical Ltd.), a trachea was exposed, and 25 μL of hydrochloric acid (pH 1.0, 0.1 N; SIGMA) was administered into a left bronchium. As a control, a group in which only a physiological saline was injected and, after anesthesia, hydrochloric acid was administered into a left bronchium (saline/HCl), and a non-treated group (intact) were used. After 12 hours, this mouse was slaughtered, and bronchial alveolus washing (BAL) was performed with 0.7 mL of PBS two times. The cell number in the BAL solution was counted and a population of cells was quantitated by simple Giemsa staining using a simple Giemsa staining solution Diffquick (Sysmex Corporation).

Results are shown in FIG. 4B.

(Results)

Figure 4C:
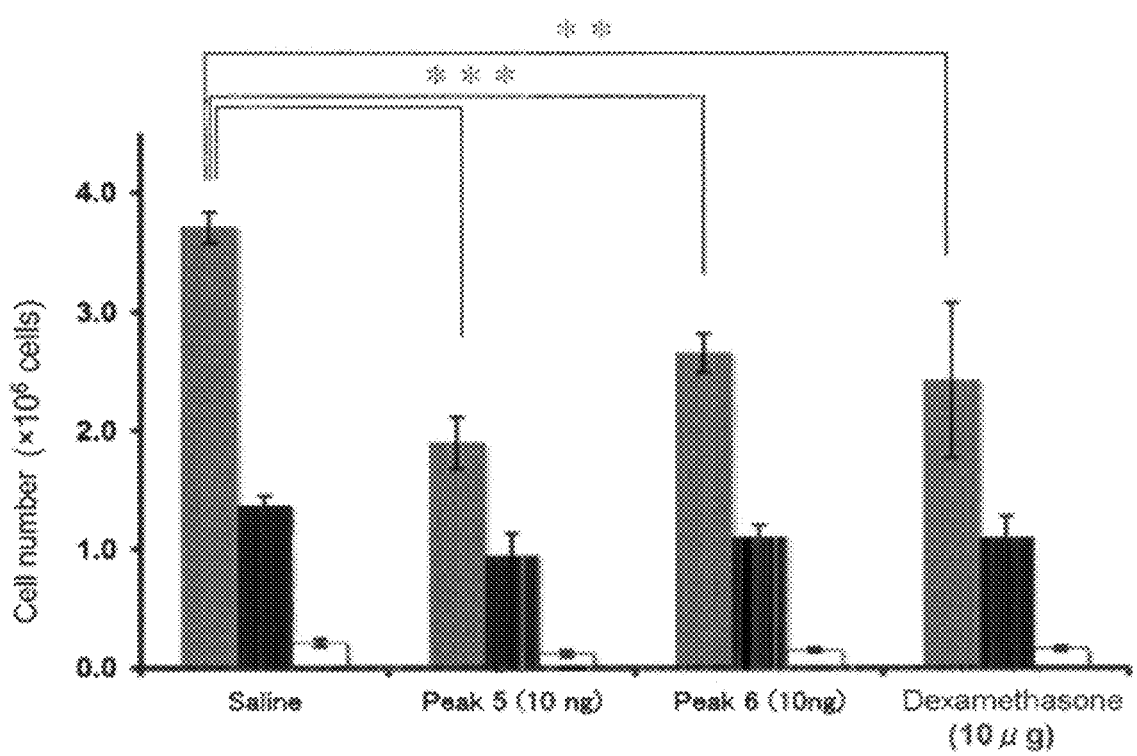
FIG. 4C shows assessment of physiological activity of peaks 5 and 6 in a zymosan peritonitis model. As a control, physiological saline and dexamethasone are used. The gray column indicates neutrophil, the black column indicates lymphocyte, and the white column indicates macrophage.
Figure 4D:
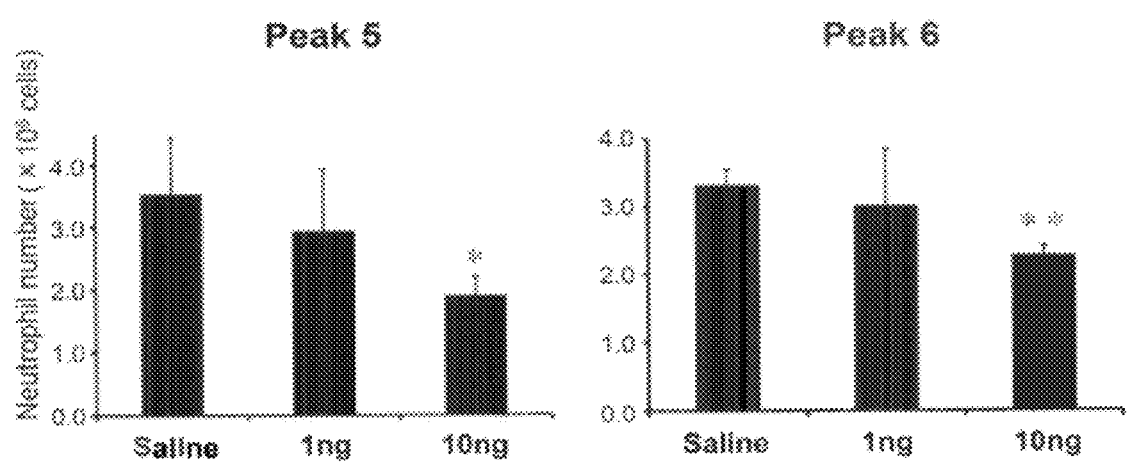
FIG. 4D shows that activity of a synthesized compound in a peritonitis model is dose-dependent. The result is shown as an average+SD, * represents p<0.05 for physiological saline, and ** represents p<0.001 for physiological saline.

When the synthesized compound was assessed in a zymosan peritonitis model, activities of suppressing infiltration of neutrophil at an inflammation initial stage were recognized at a low dose of 10 ng in peaks 5 and 6 corresponding to 17,18-diHEPE (FIG. 4C). In addition, these activities were dose-dependent (FIG. 4D), and neutrophil infiltration suppressing activity at 10 ng was equivalent to 10 μg of dexamethasone being an anti-inflammatory steroid (FIG. 4C). At this time, the suppressing effect for other cell group (macrophage etc.) was not recognized. Activity of 17,18-diHEPE has remarkably high activity on neutrophil as compared with other existing drugs (FIG. 4C).

Figure 4E:
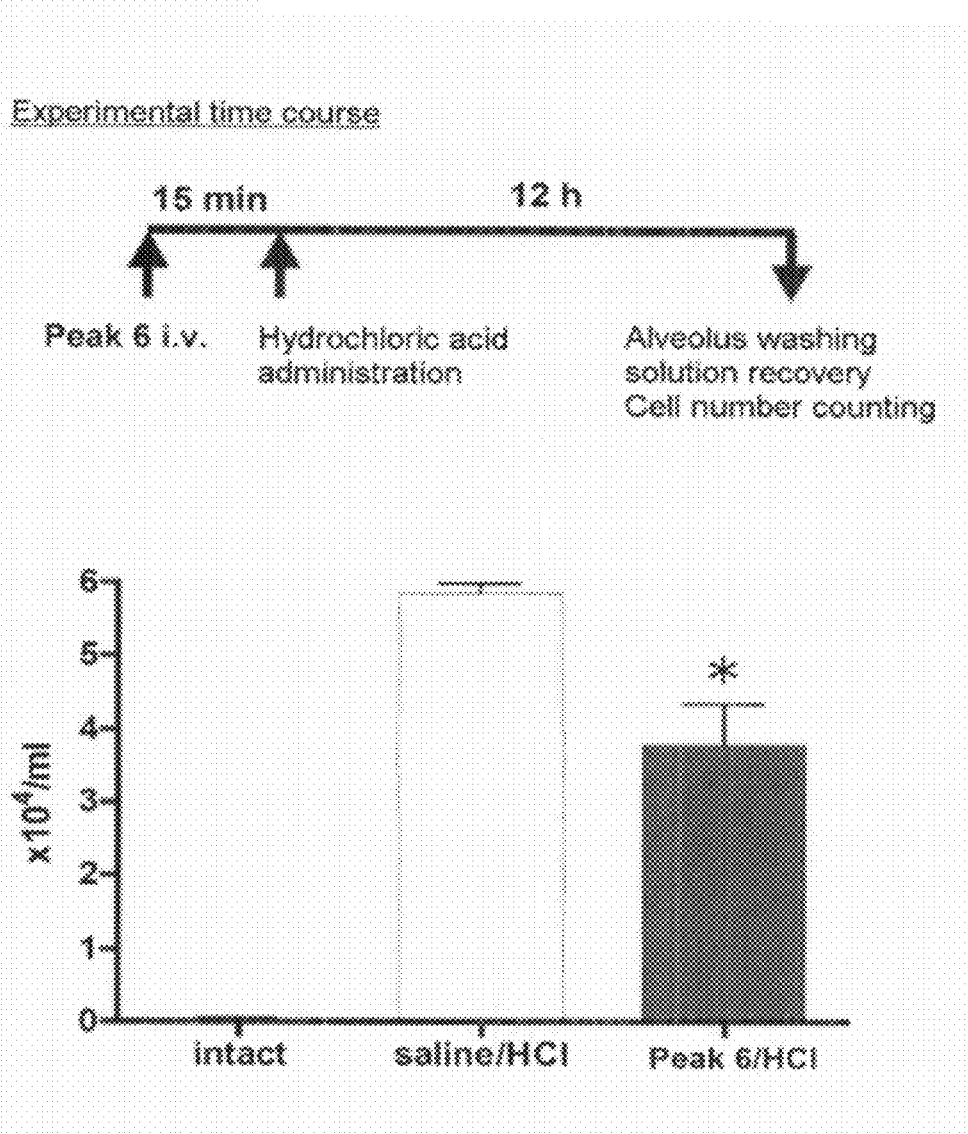
FIG. 4E shows assessment of activity of a synthesized compound in an acute lung damage model. From the left side, the number of neutrophil which have infiltrated into lung at the time point of 12 hours after non-treatment (intact), intrabronchial hydrochloric acid administration (saline/HCl), and intrabronchial hydrochloric acid administration after tail vale administration of 10 ng of peak 6 (Peak 6/HCl) are shown.

In addition, in order to assess infiltration of neutrophil in a model other than a peritonitis model, regarding 17,18-diHEPE for which activity was recognized in peritonitis, analysis of an acute lung damage model was performed. As a result, also in this model, regarding the peak 6, neutrophil-specific infiltration suppressing activity was recognized at 10 ng (FIG. 4E). By this result, it is expected that this compound exhibits the therapeutic effect on a respiratory disease having characteristic of infiltration of neutrophil (ischemic reperfusion disorder and idiopathic pulmonary fibrosis etc.).

This is expressed as $IC_{40}$ as in FIG. 4F. As seen from this graph, $IC_{40}$ was calculated to be approximately 8 ng. Since in the conventional compound, at highest around 100 ng was strongest, this results in that the compound of the present invention exhibits neutrophil suppressing activity which is one order or more stronger than the conventional activity.

When zymosan is intraperitoneally administered, persistent macrophage in an abdominal cavity senses this, and releases a neutrophil chemotactic factor. Then, neutrophil in peripheral blood interacts with a vascular endothelial cell via integrin, and infiltrates between endothelial cells and migrates to an inflammation site. Therefore, as a mechanism by which infiltration of neutrophil is suppressed, a possibility that 17,18-diHEPE acts on macrophage and suppresses release of a neutrophil chemotactic factor, and a possibility that it acts on a vascular endothelial cell or neutrophil and suppresses infiltration are thought. Assay using cells can reveal an acting point of 17,18-diHEPE.

A possibility that this time identified 17,18-diHEPE suppresses infiltration of neutrophil into an inflammation site by any mechanism, and contributes to termination of inflammation is shown.

Example 5

Example of Production by Recombinant LOX

It will be demonstrated that the compound of the present invention is produced using a recombinant enzyme expressing mouse 12/15-LOX or platelet-type 12-LOX in *Escherichia coli* in place of sLOX in Example 3.

A recombinant enzyme can be produced using the technique well-known in the art (e.g., Sambrook J. et al. which is incorporated into the present specification etc.) for recombinant technique etc., with reference to information regarding enzymes in Yoshimoto T. et al. Prostaglandins and Other Lipid Mediators Vol. 68-69, 245-262 (2002) for platelet type 12-LOX, and Kuhn H. et al. Prostaglandins and Other Lipid Mediators Vol. 68-69, 263-290 (2002) for lymphocyte-type 12/15-LOX.

Using the thus synthesized enzyme in place of sLOX used in Example 3, the compound of the present invention can be synthesized.

Since it is seen that, in incubation with lymphocyte, 8,18-diHEPE, 12,18-diHEPE, and 17,18-diHEPE are produced 12/15-LOX-dependently, it is expected that these compounds are mainly produced. In addition, also in the case of platelet-type 12-LOX, the similar result is expected.

In addition, when HDoPA is used as a raw material, it is expected that 13,20-diHDoPE, 14,20-diHDoPE, and 19,20-diHDoPE are produced.

Example 6

Physiological Activity of DHA Metabolites

Activity of substances produced in Example 5 is measured based on the protocol described in Example 4.

As a result, neutrophil suppressing activities of 8,18-diHEPE, 12,18-diHEPE, 17,18-diHEPE, 13,20-diHDoPE, 14,20-diHDoPE, and 19,20-diHDoPE can be measured.

Example 7

Example of Synthesis Using Recombinant Mouse LOX

In the present Example, it will be demonstrated that the compound of the present invention is produced using recombinant mouse 8-LOX in place of sLOX in Example 3.
(Material)
(1. Preparation of Dihydroxy Body by Enzymatic Reaction)
PBS
Recombinant mouse 8-lipoxygenase (8-LOX): RNA was extracted from a mouse skin, amplified by RT-PCR, incorporated into a pCold TF DNA (TaKaRa) vector, and transformed into a BL-21 competent cell. *Escherichia coli* with a gene introduced therein was cultured on a LB medium, IPTG was added to 1 mM, and a protein was induced at 15° C. *Escherichia coli* after inducement was ground, and the centrifuged supernatant was subjected to a nickel column to purify an objective protein.
Sodium tetrahydroborate (NaBH$_4$): Wako Pure Chemical Industries, Ltd.
18-HEPE and 20-HDoHE: Cayman
(2. Purification of Compound Using Reverse Phase HPLC)
  Methanol: Wako Pure Chemical Industries, Ltd.
  Acetic acid (Wako Pure Chemical Industries, Ltd.) was added to 0.01% v/v acetic acid: milliQ (pure water) to 0.01% v/v.

(Method)
(a. Synthesis by Enzymatic Reaction)
  18-HEPE or 20-HDoHE was taken into a reactor, a solvent was vaporized with nitrogen, and PBS was added thereto so that a concentration of 18-HEPE or 20-HDoHE was 30 μg/mL, to dissolve the material. 8-LOX was added thereto to 0.1 mg/mL to progress an enzymatic reaction and, thereafter, a reducing reaction was performed using NaBH$_4$. Thereafter, a fraction of a fatty acid metabolite was prepared by solid phase extraction.
(b. Separation and Purification of Compound by Reverse Phase HPLC)
  A solvent of the fraction of a fatty acid metabolite prepared as described above was vaporized with nitrogen, and this was dissolved in an initial stage mobile phase of HPLC (for reaction product of 18-HEPE, H$_2$O/MeOH/acetic acid=35/65/0.01 and, for reaction product of 20-HDoHE, H$_2$O/MeOH/acetic acid=30/70/0.01). This was subjected to HPLC (Agilent Technologies), and peaks were fractionated into glass small test tubes. A solvent was evaporated with nitrogen to dryness, and the fractions were finally stored as an ethanol solution at −20° C. The condition of reverse phase HPLC was as follows:
  Composition of Mobile Phase
  A liquid: methanol
  B liquid: milliQ water/acetic acid=100/0.01
  (Reaction Product of 18-HEPE)
  0 to 21 minutes A65%
  21 to 35 minutes A100%
  (Reaction Product of 20-HDoHE)
  0 to 21 minutes A70%
  21 to 35 minutes A100%
  Column
  TSK-GEL ODS-100V 3 μm, 4.6 mm×7.5 cm (Tosoh Corporation)
  Flow Rate
  0.7 mL/minute.
(Results)
  When 18-HEPE was reacted with 8-LOX, and the product was purified by reverse phase HPLC, one peak was generated (FIG. 5A). Then, when two were fractionated, and measured by MS/MS, a MS/MS value of a fragment ion generated by introduction of a hydroxyl group at an 8-position and an 18-position of EPA was recognized and, therefore, this was thought to be 8,18-diHEPE (FIG. 5B).
  Regarding the reaction product at a reaction between 20-HDoHE and 8-LOX, one peak was similarly generated (FIG. 6A), and this was similarly thought to be 10,20-diHDoHE from the result of MS/MS (FIG. 6B).
  From the above results, it was demonstrated that the compound of the present invention can be synthesized also in the case of use of 8-LOX, like 12/15-LOX or sLOX.

Example 8

Synthesis of Metabolites Derived from 12-HpEPE and 14-HpDoHE

In the present Example, it is demonstrated that the compound of the present invention is produced using, as a substrate, 12-HpEPE and 14-HpDoHE in place of 18-HEPE and 20-HDoHE.
(Material)
(1. Preparation of Dihydroxy Body by Enzymatic Reaction)
  Enzymatic reaction using soybean lipoxygenase (sLOX)
  Borate buffer (pH 9.0)

Figure 7:
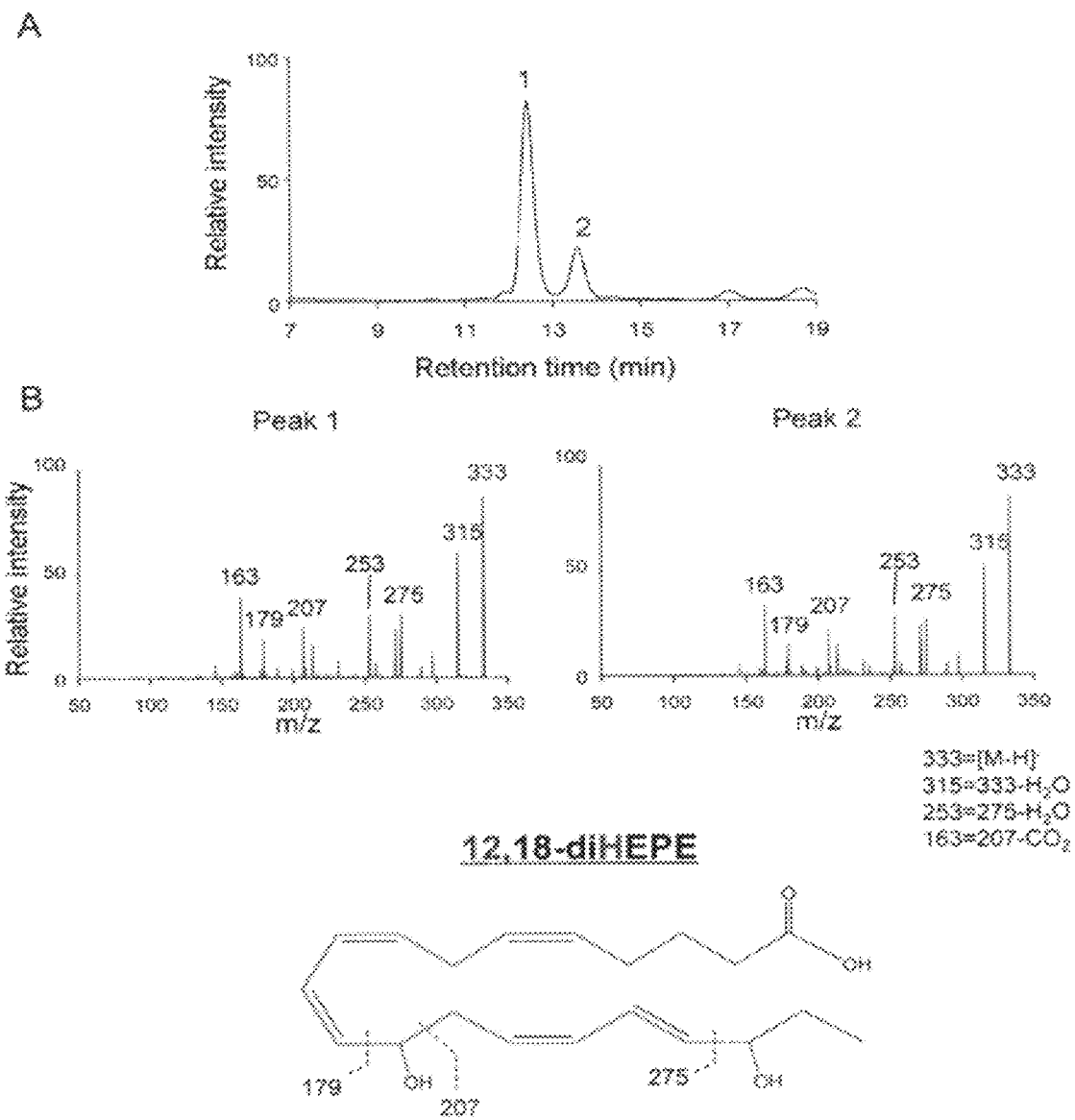
FIG. 7 shows (A) reverse phase HPLC chromatogram of a sample obtained by incubation of 12-HpEPE with sLOX, and (B) mass spectroscopy (MS/MS) of peaks 1 and 2 and the structure of 12,18-diHEPE.

Boric acid and potassium chloride (both Wako Pure Chemical Industries, Ltd.) were dissolved in milliQ water. A 1N potassium hydroxide (Wako Pure Chemical Industries, Ltd.) solution was added to set a pH at 9.0 and, thereafter, boric acid and potassium chloride were diluted with milliQ water to 50 mM.
Soybean lipoxygenase (sLOX): SIGMA
Sodium tetrahydroborate ($NaBH_4$): Wako Pure Chemical Industries, Ltd.
12-HpEPE and 14-HpDoHE: EPA and DHA were reacted with mouse 12-LOX (prepared as mouse 8-LOX of Example 7), respectively, and the products were extracted, and prepared.
(2. Purification of Compound Using Reverse Phase HPLC)
Methanol: Wako Pure Chemical Industries, Ltd.
Acetic acid (Wako Pure Chemical Industries, Ltd.) was added to 0.01% v/v acetic acid: milliQ (pure water) to 0.01% v/v.
(Method)
(a. Synthesis by Enzymatic Reaction)
12-HpEPE or 14-HpDoHE was taken into a reactor, a solvent was vaporized with nitrogen, and a borate buffer was added thereto so that a concentration of 12-HpEPE or 14-HpDoHE was 30 µg/mL, to dissolve it. Then, sLOX was added thereto to 0.1 mg/mL to progress an enzymatic reaction and, thereafter, a reducing reaction was performed using $NaBH_4$. Thereafter, a fraction of a fatty acid metabolite was prepared by solid phase extraction.
(b. Separation and Purification of Compound by Reverse Phase HPLC)
A solvent of the fraction of a fatty acid metabolite prepared as described above was vaporized with nitrogen, and the product was dissolved in an initial stage mobile phase of HPLC (for reaction product of 12-HpEPE, $H_2O$/MeOH/acetic acid=35/65/0.01 and, for reaction product of 14-HpDoHE, $H_2O$/MeOH/acetic acid=30/70/0.01). This was subjected to HPLC (Agilent Technologies), and peaks were fractionated into glass small test tubes. A solvent was vaporized with nitrogen to dryness, and the product was finally stored as an ethanol solution at −20° C. The condition of reverse phase HPLC was as follows:
Composition of Mobile Phase
A liquid: methanol
B liquid: milliQ water/acetic acid=100/0.01
(Reaction Product of 12-HpEPE)
0 to 21 minutes A65%
21 to 35 minutes A100%
(Reaction Product of 14-HpDoHE)
0 to 21 minutes A70%
21 to 35 minutes A100%
Column
TSK-GEL ODS-100V 3 µm, 4.6 mm×7.5 cm (Tosoh Corporation)
Flow Rate
0.7 mL/minute.
(Results)
When 12-HpEPE was reacted with sLOX, and the product was purified by reverse phase HPLC, two peaks were generated (FIG. 7A). Then, when two were fractionated, and MS/MS was measured, a MS/MS value of a fragment ion generated by introduction of a hydroxyl group at a 12-position and an 18-position of EPA was recognized in both of them, and thus the product was thought to be 12,18-diHEPE (FIG. 7B). A plurality of peaks were recognized, but they were thought to be derived from cis or trans of a double bond, or to be due to that configuration of a hydroxyl group was a S body or a R body.

Regarding the reaction product of 14-HpDoHE and sLOX, five peaks were generated (FIG. 8A). Regarding two of them, they were similarly thought to be 14,20-diHDoHE from MS/MS (FIG. 8B).
From the above result, it was demonstrated that, also when 12-HpEPE or 14-HpDoHE is used as a substrate, the compound of the present invention can be synthesized like 18-HEPE or 20-HDoHE. A reaction mechanism of an enzymatic reaction to be thought at this time is shown in FIGS. 9A to B. It is thought that sLOX produces the metabolite of the present invention, as a result of extraction of hydrogen from carbon at a 16-position of EPA, and an 18-position of DHA.

Example 9

Comparison of Physiological Activity Regarding Various Compounds

Figure 10:
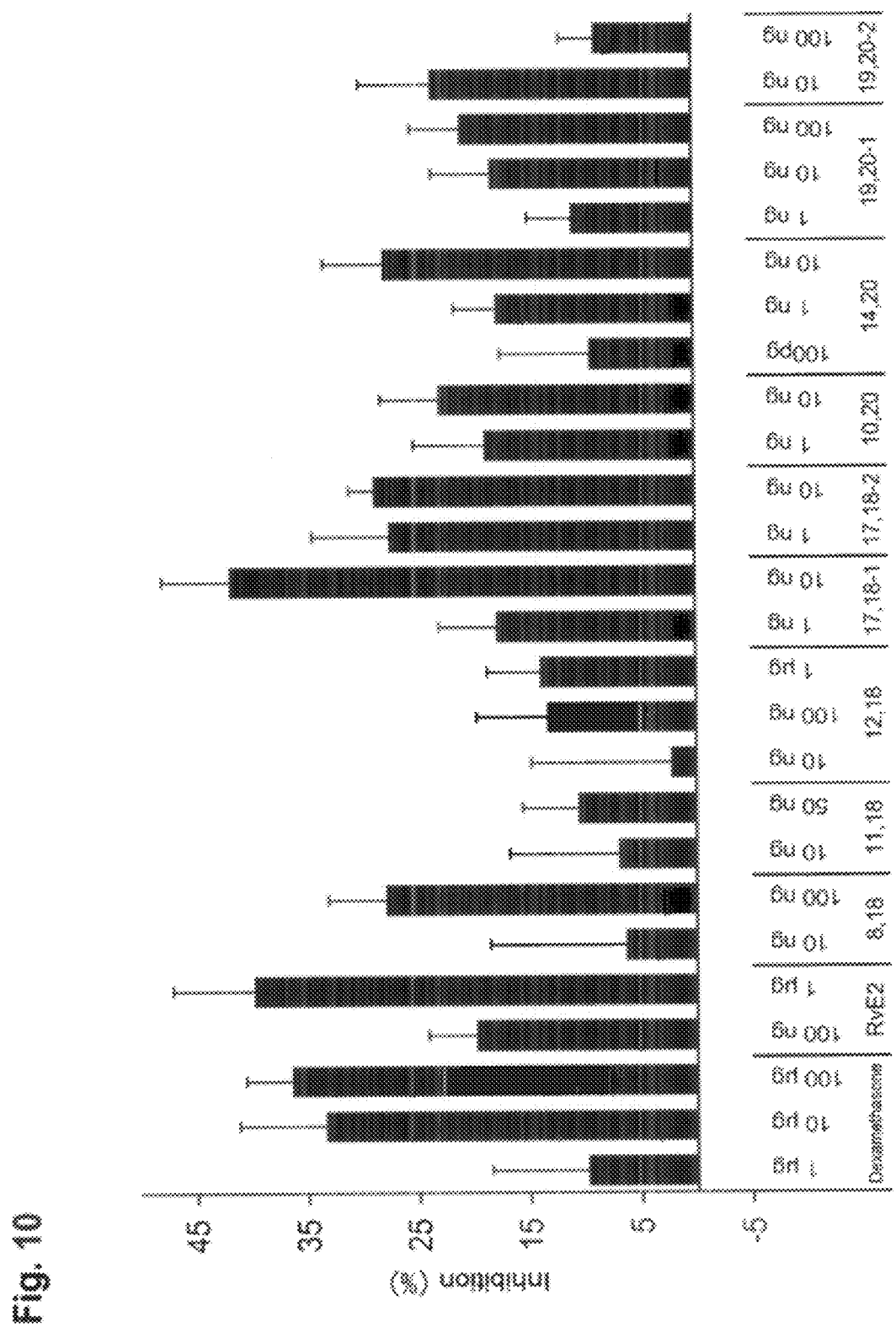
FIG. 10 shows comparison of activities regarding a variety of compounds.

According to a procedure of the zymosan peritonitis model of Example 4, regarding each of dexamethasone, Resolvin E2 (RvE2), 8,18-diHEPE, 11,18-diHEPE, 12,18-diHEPE and 17,18-diHEPE, 10,20-diHDoHE, 13,20-diHDoHE, 14,20-diHDoHE and 19,20-diDoHE, physiological activities were studied by comparison.
(Material)
Mouse C57BL/6J 7 weeks old, male: CLEA Japan, Inc.
Physiological saline: Otsuka Pharmaceutical Co., Ltd.
Zymosan A: Wako Pure Chemical Industries, Ltd.
Phosphate buffered physiological saline (PBS)
Dexamethasone: SIGMA
Resolvin E2 (RvE2): This was prepared according to Ogawa S. et al., Org. Lett. 11, 3602-3605 (2009).
8,18-diHEPE, 11,18-diHEPE, 12,18-diHEPE and 17,18-diHEPE, 10,20-diHDoHE, 13,20-diHDoHE, 14,20-diHDoHE and 19,20-diDoHE: Each was prepared by an enzymatic reaction described in the aforementioned Examples etc. using 18-HEPE or 20-HDoHE as a substrate.
(Method)
For an inflammation model, zymosan peritonitis elicited by intraperitoneally administering zymosan being a cell wall component of yeast was used. Since the present model can recover an exudate in an abdominal cavity, it is a model suitable for analyzing cytokines and eicosanoids.
Zymosan A (Wako Pure Chemical Industries, Ltd.) was suspended in a physiological saline to 1 mg/mL, and the suspension was warmed at 37° C. for 30 minutes. Thereafter, this zymosan A solution was vortexed, and returned to room temperature. Various compounds were taken into a 1.5 mL tube, a solvent was vaporized with nitrogen to complete dryness, and a physiological saline was added to dissolve the compound. Then, 100 µL of this compound solution was injected through a tail vein of C57BL/6J mouse (7 weeks old, male: CLEA Japan, Inc.) (for EPA metabolites and DHA metabolites, 100 pg, 1 ng, 10 ng, 50 ng or 100 ng/mouse, for RvE2, 100 ng or 1 µg/mouse, for dexamethasone, 1 µg, 10 µg or 100 µg/mouse; each see FIG. 10). As a control, a group in which only a physiological saline was injected, and a group in which dexamethasone (10 µg/mouse) being an anti-inflammatory steroid was injected, were used. After about 2 minutes, 1 mL of a zymosan A solution was intraperitoneally administered. After 2 hours, cells exuded into an abdominal cavity were recovered into a tube with PBS, and the cell number was counted.
(Results)
When a variety of compounds were assessed in a zymosan peritonitis model, dose-dependent neutrophil infiltration suppressing activities were seen regarding a variety of compounds (FIG. 10). In 17,18-diHEPE and 14,20-diHDoHE, activity exceeding that of 1 µg of dexamethasone being an anti-inflammatory steroid was seen at 1 ng, and it is seen that neutrophil infiltration suppressing activities of 17,18-diHEPE and 14,20-diHDoHE are very strong.

Putting together, in 8,18-diHEPE, 12,18-diHEPE, 17,18-diHEPE, 10,20-diHDoHE, 14,20-diHDoHE, and 19,20-diHDoHE, the statistically significant effect is seen, and it was found out that there is a tendency that 11,18-diHEPE also has neutrophil infiltration suppressing activity. Since 13,20-diHDoHE has a structure similar to those of these seven compounds, there is a possibility that it has anti-inflammatory activity, and it is greatly expected that anti-inflammatory activity is measured in another measuring system.

Example 10

Production by Human Eosinophil

In the present Example, production of the novel compound of the present invention by human eosinophil was demonstrated.

Eosinophil was purified from human peripheral blood using the known technique. Specifically, neutrophil was removed and separated from a granulocyte fraction obtained from peripheral blood using CD16 Microbeads (Miltenyl Biotec) (Hansel et al. (1991) J. Immunol. Methods 145, 105-110). This human eosinophil was stimulated by adding 10 µM of 18-HEPE or 20-HDoHE to $1.0 \times 10^6$ cells/ml in HESS, and adding 10 µM of calcium ionophore A23187 (SIGMA), ice-cooled methanol was added after 30 minutes to stop the reaction, and solid phase extraction was performed. Solid phase extraction was performed as described in Examples etc.

Analysis was performed using MRM, as described in Examples 1 and 2 etc.

(Results)

Figure 11:
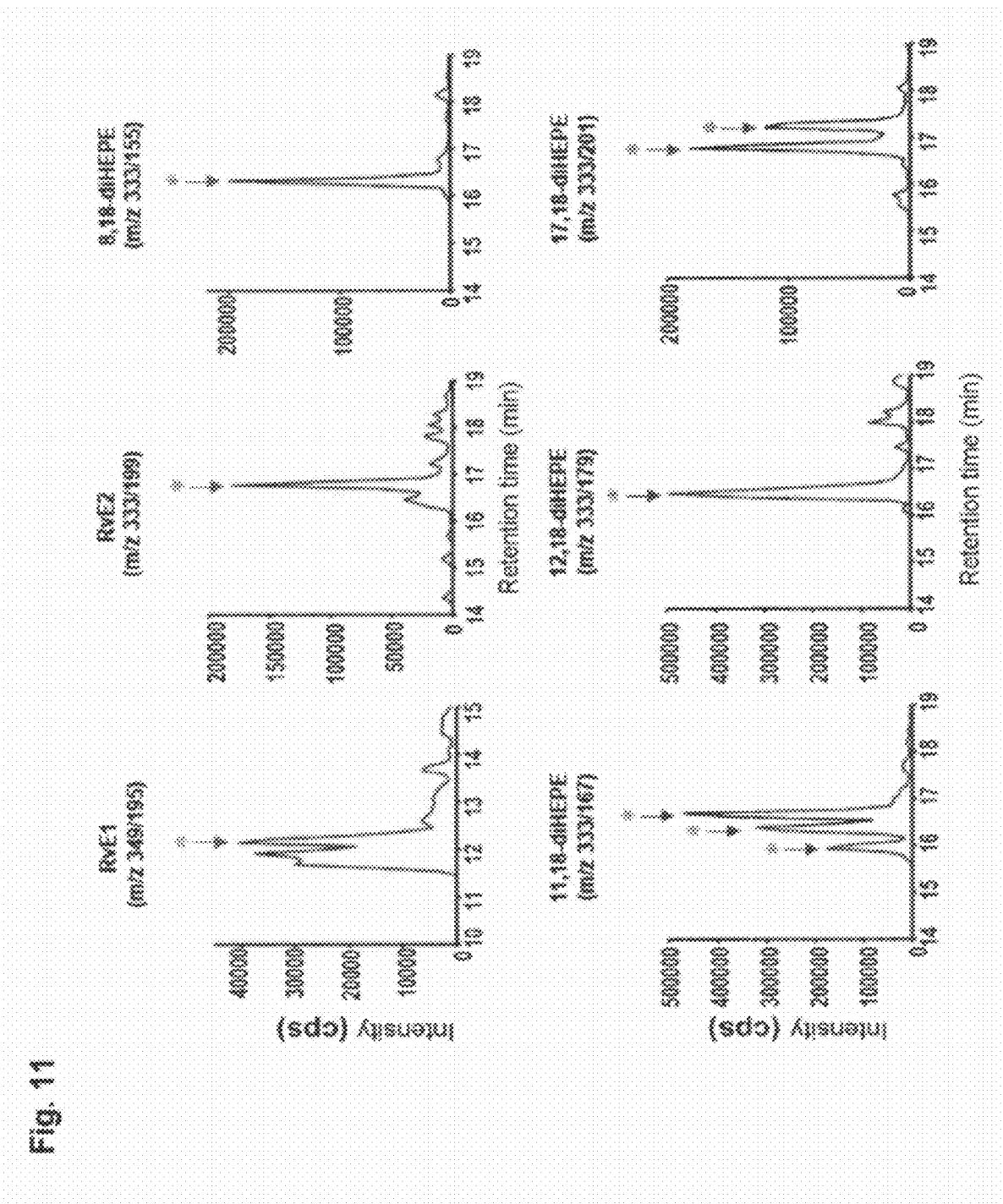
FIG. 11 shows the analysis results of each metabolite generated as the result of incubation of 18-HEPE with human eosinophil. An asterisk indicates a peak of each main metabolite. From the left upper side to the right upper side, an asterisk indicates Resolvin E1, Resolvin E2, and 8,18-diHEPE in this order and, from the left lower side to the right lower side, an asterisk indicates 11,18-diHEPE, 12,18-diHEPE and 17,18-diHEPE in this order.
Figure 12:
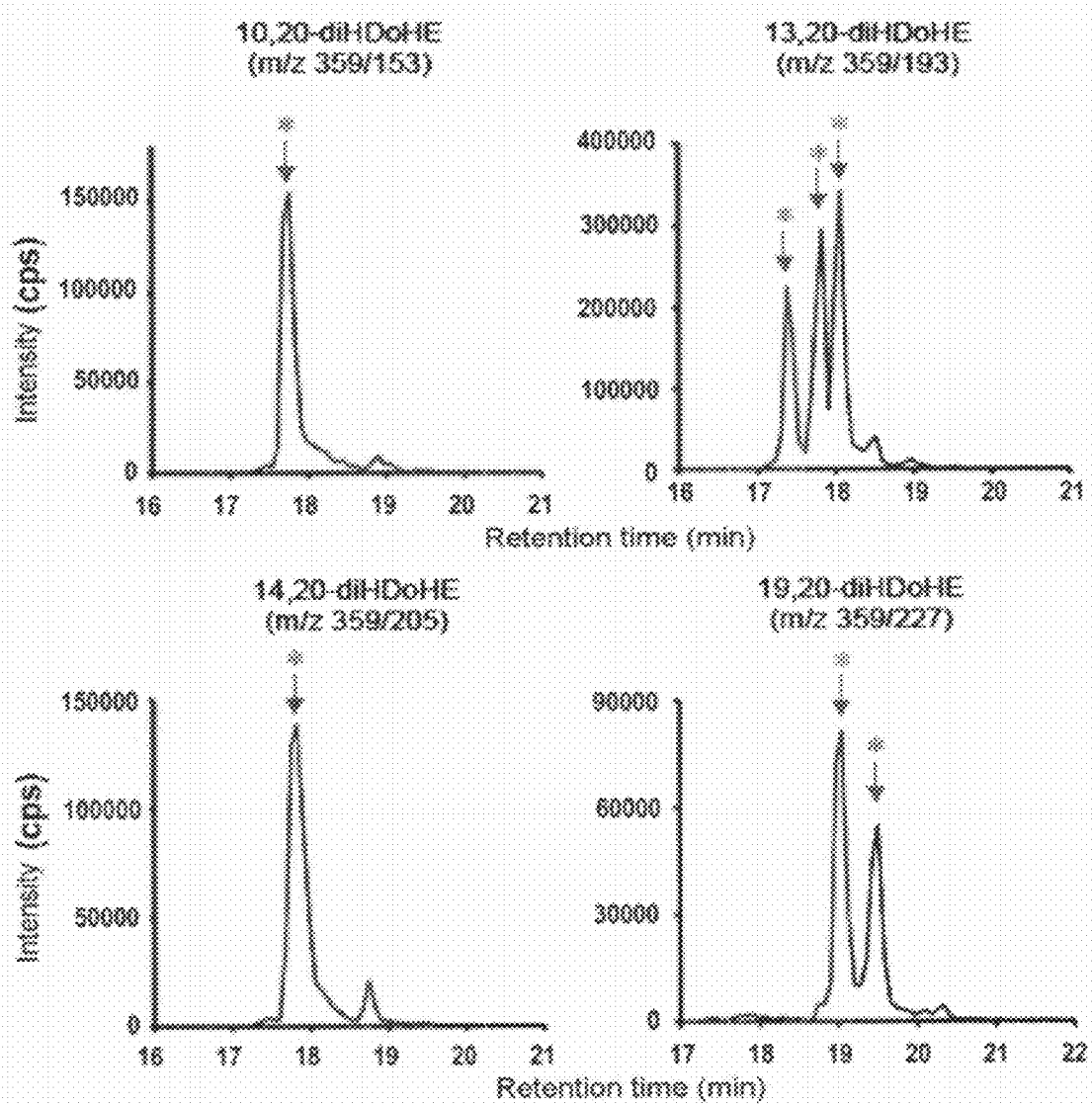
FIG. 12 shows the analysis results of each metabolite generated as the result of incubation of 20-HDoHE with human eosinophil. An asterisk indicates a peak of each main metabolite. From the left upper side to the right upper side, an asterisk indicates 10,20-diHDoHE, and 13,20-diHDoHE in this order and, from the left upper side to the right upper side, an asterisk indicates 14,20-diHDoHE and 19,20-diDoHE in this order.

As described in FIGS. 11 and 12, when 18-HEPE was used as a raw material, 8,18-diHEPE, 11,18-diHEPE, 12,18-diHEPE, and 17,18-diHEPE of the present invention were generated. In addition, production of Resolvin E1 and Resolvin E2 was also observed. When 20-HDoHE was used as a raw material, 10,20-dHDoHE, 13,20-dHDoHE, 14,20-dHDoHE, and 19,20-dHDoHE were generated. From these things, it was found out that a MRM chromatogram as a result is basically similar to the result of mouse eosinophil.

From the foregoing, it is understood it can be said that the compound of the present invention is present in a living body also in human.

In addition, it was made clear that the compound of the present invention can be produced not only by mouse eosinophil, but also by human eosinophil.

Example 11

Experiment of Inhibition of Migration of Human Neutrophil

In order to measure suppressing activity on neutrophil from another viewpoint, an experiment of inhibition of migration of human neutrophil is performed.

Compounds produced in Examples 3 and 5 are used.

Neutrophil is isolated from human peripheral blood (see Serhan C. N. et al. Biochemistry. 34, 14609-14615 (1995)), mixed into a culturing solution (RPMI-0.1% BSA) to which a target compound has been added, to $3 \times 10^5$ cells/200 µl, and this is incubated at 37° C. for 15 minutes. Thereafter, this is transferred to a cell culture insert (24 well, 3 µm pore; manufactured by Falcon), LTB4 (5 nM) as a chemotactic factor is added to a lower layer, and the number of neutrophil transferred to a lower layer after 2 hours is measured.

Like this, a compound which performs migration inhibition can be analyzed.

(Discussion)

From the results of the present Example and other Examples, the compound of the present invention can be discussed as follows. The compound of the present invention exhibits neutrophil suppression in vitro and in vivo. Therefore, the pharmaceutical composition of the present invention can be used as an agent for preventing and/or treating diseases such as encephalitis, myelitis and encephalomyelitis, meningitis, inflammatory multiple neuropathy, neuritis, dacryoadenitis, orbital inflammation, conjunctivitis (allergic conjunctivitis, spring keratoconjuctivitis etc.), keratitis, chorioretinal scar, endophthalmitis, retrobulbar neuritis, retinopathy, glaucoma, cellulitis, external otitis, perichondritis, tympanitis, salpingitis, mastoiditis, myringitis, labyrinthitis, pulpitis, periodontitis, sialitis, stomatitis, glossitis, thyroiditis, pericarditis, endocarditis, myocarditis, hypertension, cardiac failure, arteriosclerosis (atherosclerosis etc.), restenosis, ischemic reperfusion disorder, thrombosis (cardiac infarct, cerebral infarct etc.), obesity, angiitis, vasculitis, multiple arteritis, lymphadenitis, lymphoma, Hodgkin's disease, eosinophilic disease (eosinophilia, pulmonary eosinophilia, pulmonary aspergillosis etc.), inflammatory or obstructive airway disease (allergic rhinitis, chronic sinusitis, pneumonia, laryngitis, laryngotracheitis, bronchitis, asthma, acute lung disorder, acute respiratory distress syndrome, emphysema, chronic obstructive pulmonary disease etc.), pleurisy, pneumoconiosis, mesothelioma, esophagitis, gastro-jejunal ulcer, gastritis, duodenitis, food allergy, sepsis, hepatitis, hepatic fibrosis, hepatic cirrhosis, cholecystitis, pancreatitis, peritonitis, diabetes (type I diabetes, type II diabetes), inflammatory or allergic skin disease (atopic dermatitis, contact dermatitis (allergic contact dermatitis, irritant contact dermatitis etc.), psoriasis, hives, light allergic response, alopecia greata etc.), skin hypertrophic disorder (skin eosinophilic granuloma etc.), skin polymyositis, inflammation of subcutaneous adipose tissue, hyperthyroidism, sarcoidosis, autoimmune blood disease (hemolytic anemia, idiopathic thrombocytopenic purpura etc.), (systemic) lupus erythematodes, relapsing polychondritis, multiple leptomeningitis, sclerodoma, Wegener's granulomatosis, dermatomyositis, chronic active hepatitis, myasthenia gravis, Stevens-Johnson syndrome, idiopathic sprue, autoimmune inflammatory bowel disease (ulcerative colitis, Crohn's disease etc.), endocrine ophthalmopathy, sarcoidosis, alveolitis, chronic hypersensitivity pneumonitis, multiple sclerosis, primary biliary cirrhosis, uveitis, keratoconjunctivitis sicca, interstitial pulmonary fibrosis, iridocyclitis, psoriatic arthritis, glomerular nephritis, systemic sclerosis, systemic connective tissue disease (Sjogren's syndrome, Behcet's disease, diffuse myofascitis etc.), interstitial myositis, inflammatory multiple joint disorder, inflammatory arthritis, arthrorheumatism, osteoarthritis, synovitis, bursitis, thecitis, chronic multiple myelitis, nephritis syndrome, tubulointerstitial nephritis, cystitis, prostatitis, orchitis, epididymitis, salpingitis, ovaritis, trachelitis, female pelvic inflammation, vulvovaginitis, organ transplant rejection, bone-marrow transplant rejection, and graft versus host disease, and/or an agent for treating thermal injury or traumatic inflammation.

Example 12

Solubility Test

The solubility of a compound can be determined under the condition of addition of 1% DMSO. A 10 mmol/L compound solution is prepared with DMSO, and 6 μL of the compound solution can be added to 594 μL of an artificial intestine fluid having a pH of 6.8 (118 mL of a 0.2 mol/L sodium hydroxide (NaOH) test solution, and water was added to 250 mL of a 0.2 mol/L dihydrogen potassium phosphate test solution to 1000 mL). After allowing to stand at 25° C. for 16 hours, a mixed solution can be suction-filtered. The filtrate was diluted 2-fold with methanol/water=1/1, and a concentration in the filtrate can be measured using HPLC or LC/MS/MS by an absolute calibration curve method.

Example 13

Metabolism Stability Test

Using commercially available pooled human hepatic microsome, a subject compound is reacted for a certain time, a remaining rate is calculated by comparison between the reacted sample and unreacted sample, and a degree metabolized in liver can be assessed.

A reaction can be performed at 37° C. for 0 minutes or 30 minutes in the presence of 1 mmol/L NADPH, in 0.2 mL of a buffer (50 mmol/L Tris-HCl pH 7.4, 150 mmol/L potassium chloride, 10 mmol/L magnesium chloride) containing human hepatic microsome 0.5 mg protein/mL (oxidative reaction). After the reaction, 50 μL of a reaction liquid can be added to 100 μL of a methanol/acetonitrile=1/1 (v/v) solution, mixed, and centrifuged at 3000 rpm for 15 minutes. A test compound in the centrifugation supernatant can be quantitated by LC/MS/MS, and a remaining rate of the test compound after the reaction for 30 minutes can be calculated by assuming that a compound amount at 0 minutes reaction time is 100%.

Regarding the result, various cases such as the case where a compound concentration is 0.5 μmol/L and the case where a compound concentration is 2 μmol/L can be assessed.

Example 14

CYP Inhibiting Test

Using a commercially available pooled human hepatic microsome, a degree of inhibition of each metabolite production amount by a test compound can be assessed using, as an index, O-deethylation of 7-ethoxyresoruf in (CYP1A2), methyl-hydroxylation of tolbutamide (CYP2C9), 4'-hydroxylation of mephenyloin (CYP2C19), O-demethylation of dextromethorphan (CYP2D6), hydroxylation of terfenadine (CYP3A4) as a typical substrate metabolism reaction of human main CYP5 molecular species (CYP1A2, 2C9, 2C19, 2D6, 3A4).

The reaction condition is as follows: substrate, 0.5 μmol/L ethoxyresoruf in (CYP1A2), 100 μmol/L tolbutamide (CYP2C9), 50 μmol/L S-mephenyloin (CYP2C19), 5 μmol/L dextromethorphan (CYP2D6), 1 μmol/L terfenadine (CYP3A4); reaction time, 15 minutes; reaction temperature, 37° C.; enzyme, pooled human hepatic microsome 0.2 mg protein/mL; test drug concentration, 1, 5, 10, 20 μmol/L (4 points).

As a reaction solution, each five kinds of substrates, human hepatic microsome, and a test drug are added in the aforementioned composition to a 50 mmol/L Hepes buffer in a 96-well plate, NADPH which is a coenzyme is added to initiate a metabolism reaction as an index, the reaction is performed at 37° C. for 15 minutes, and a methanol/acetonitrile=1/1 (v/v) solution is added to stop the reaction. After centrifugation operation at 3000 rpm for 15 minutes, resorufin (CYP1A2 metabolite) in the centrifugation supernatant can be quantitated with a fluorescent multilabel counter, and tolbutamide hydroxide body (CYP2C9 metabolite), mephenyloin 4'-hydroxide body (CYP2C19 metabolite), dextromethorphan (CYP2D6 metabolite), and terfenadine alcohol body (CYP3A4 metabolite) can be quantitated by LC/MS/MS.

A sample in which only DMSO being a solvent for dissolving a drug can be added to a reaction system is defined as a control (100%), remaining activity (%) at each concentration at which a test drug solution is added, is calculated, and $IC_{50}$ can be calculated by reverse presumption with a logistic model using a concentration and a suppression rate.

Example 15

CYP3A4 Fluorescent MBI Test)

A CYP3A4 fluorescent MBI test is a test which examines potentiation of CYP3A4 inhibition of a compound by a metabolism reaction, Escherichia coli-expressing CYP3A4 is used as an enzyme, 7-benzyloxytrifluoromethylcoumarine (7-BFC) is debenzylated with the CYP3A4 enzyme, and the test is performed using, as an index, a reaction which generates a metabolite which emits fluorescence, 7-hydroxytrifluoromethylcoumarine (HFC).

The reaction condition is as follows: substrate, 5.6 μmol/L 7-BFC; pre-reaction time, 0 or 30 minutes; reaction time, 15 minutes; reaction temperature 25° C. (room temperature); CYP3A4 content (Escherichia coli-expressing enzyme), 62.5 pmol/mL at pre-reaction, 6.25 pmol/mL at reaction (at 10-fold dilution); test drug concentration, 0.625, 1.25, 2.5, 5, 10, 20 μmol/L (6 points).

As a pre-reaction solution, an enzyme and a test drug solution are added in the aforementioned pre-reaction composition to a K-Pi buffer (pH 7.4) in a 96-well plate, a part thereof is transferred to another 96-well plate so that it is 1/10 diluted with a substrate and a K-Pi buffer, NADPH being a coenzyme is added to initiate a reaction as an index (no pre-reaction) and, after a reaction for a predetermined time, acetonitrile/0.5 mol/L Tris (trishydroxyaminomethane)=4/1 is added to stop the reaction. Separately, NADPH is also added to a remaining pre-reaction solution to initiate a pre-reaction (presence of pre-reaction) and, after a pre-reaction for a predetermined time, a part thereof is transferred to another plate so that it is 1/10 diluted with a substrate and a K-Pi buffer, thereby, a reaction as an index can be initiated. After the reaction for a predetermined time, the reaction can be stopped by adding acetonitrile/0.5 mol/L Tris (trishydroxyaminomethane)=4/1. For the plate in which each index reaction has been performed, a fluorescent value of 7-HFC being a metabolite can be measured with a fluorescent plate reader (Ex=420 nm, Em=535 nm).

A sample in which only DMSO being a solvent with a drug dissolved therein is added to a reaction system is defined as a control (100%), and remaining activity (%) at each concentration at which a test drug solution is added is calculated, and $IC_{50}$ can be calculated by reverse presumption with a logistic model using a concentration and a suppression rate. The case where a difference in an $IC_{50}$ value is 5 μmol/L or more can be (+), and the case where the difference is 3 μmol/L or less can be (−).

Example 16

Fat Test

Twenty μL of freezing-stored murine Salmonella typhimurium (TA98 strain, TA100 strain) was inoculated on a 10 mL liquid nutrient medium (2.5% Oxoid nutrient broth No. 2), and this can be cultured before shaking at 37° C. for 10 hours. For the TA98 strain, 9 mL of a bacterium cell solution is centrifuged (2000×g, 10 minutes) to remove a culturing solution, and a bacterium is suspended in 9 mL of a Micro F buffer (hydrogen dipotassium phosphate ($K_2NPO_4$): 3.5 g/L, dihydrogen potassium phosphate ($KH_2PO_4$): 1 g/L, ammonium sulfate (($NH_4$)$_2SO_4$): 1 g/L, trisodium citrate dihydrate: 0.25 g/L, magnesium sulfate heptahydrate ($MgSO_4.7H_2O$): 0.1 g/L), and this is added to 110 mL of an Exposure medium (Micro F buffer containing biotin: 8 µg/mL, histidine: 0.2 µg/mL, and glucose: 8 mg/mL) and, for the TA100 strain, 3.16 mL of a bacterium cell solution is added to 120 mL of an Exposure medium, thereby, a test bacterium cell solution can be prepared. Each 12 µL of a test substance DMSO solution (8-stage dilution at a 2-fold ratio from maximum dose 50 mg/mL), DMSO as a negative control, 50 µg/mL of a 4-nitroquinoline-1-oxide DMSO solution for the TA98 strain, 0.25 µg/mL of 2-(2-furyl)-3-(5-nitro-2-furyl)acrylamide DMSO solution for the TA100 strain under non-metabolism activation condition, 40 µg/mL of 2-aminoanthracene DMSO solution for the TA98 strain, 20 µg/mL of 2-aminoanthracene DMSO solution for the TA100 strain under metabolism activation condition, as a positive control, and 588 µL of a test bacterium cell solution (under metabolism activation condition, a mixed solution of 498 µL of a test bacterium cell solution and 90 µL of S9 mix) are admixed, and this can be cultured by shaking at 37° C. for 90 minutes. 460 µL of a bacterium cell solution in which a test substance can be exposed is admixed with 2300 µL of an Indicator medium (Micro F buffer containing biotin: 8 µg/mL, histidine: 0.2 µg/mL, glucose: 8 mg/mL, bromocresol purple: 37.5 µg/mL), each 50 µL is dispensed in microplate 48 wells/dose, and this is subjected to static culturing at 37° C. for 3 days. Since a well containing a bacterium which has acquired the proliferation ability by mutation of an amino acid (histidine) synthesizing enzyme gene turns from purple to yellow by pH change, a bacterium proliferating well which can turn to yellow in 48 wells per dose is counted and can be assessed by comparing with a negative control group. Assessment can be performed by indicating negative mutagenicity as (−), and positive mutagenicity as (+).

Example 17 hERG Test

For the purpose of assessing a risk of extension of an electric cardiogram QT interval, using HEK293 cells which have expressed a human ether-a-go-go related gene (hERG) channel, an action on a delayed rectification $K^+$ current ($I_{Kr}$) which plays an important role on a cardiac ventricle repolarization stage can be studied.

Using a full automatic patch clamp system (PatchXpress 7000A, Axon Instruments Inc.), a cell is retained at a membrane potential of −80 mV by a whole cell patch clamp method and, thereafter, $I_{Kr}$ which induced when depolarization stimulation at +50 mV is given for 2 seconds and, further, repolarization stimulation at −50 mV is given for 2 seconds is recorded. After a generated current is stabilized, a cell external solution in which a test substance has been dissolved at an objective concentration (NaCl: 137 mmol/L, potassium chloride (KCl): 4 mmol/L, calcium chloride dihydrate ($CaCl_2.2H_2O$): 1.8 mmol/L, magnesium chloride hexahydrate ($MgCl_2.6H_2O$): 1 mmol/L, glucose: 10 mmol/L, HEPES (4-(2-hydroxyethyl)-1-piperazineethanesulfonic acid: 10 mmol/L, pH=7.4) is applied to cells under room temperature condition for 10 minutes. From the resulting $I_{Kr}$, an absolute value of a maximum tail current can be measured using a current value at a retained membrane potential as a standard, and employing an analysis software (DataXpress ver. 1, Molecular Devices Corporation). Further, an inhibition rate relative to a maximum tail current before application of a test substance is calculated, this is compared with a medium application group (0.1% dimethyl sulfoxide solution), and influence of the test substance on $I_{Kr}$ can be assessed. The result can indicate an inhibition rate at a compound concentration of 1 µmol/L.

Example 21

BA Test

Oral absorbability can be performed using the following BA test.

The following is an experimental material and a method.
(1) Animal to be used: A rat or a mouse was used.
(2) Rearing condition: A rat ingested a solid feed and sterilized tap water ad-libitum.
(3) Dose and setting of grouping: A predetermined dose was administered orally or intravenously. A group was set as follows (a dose varied for every compound).
Oral administration 1 to 30 mg/kg (n=2 to 3)
Intravenous administration 0.5 to 10 mg/kg (n=2 to 3)
(4) Preparation of administration solution: For oral administration, a solution or a suspension was administered. For intravenous administration, a compound which was solubilized was administered.
(5) Administration method: For oral administration, the administration solution was forcibly administered to stomach by oral sonde. For intravenous administration, the administration solution was administered with a syringe equipped with an injection needle through a tail vein.
(6) Assessment item: Blood was collected with time, and a plasma drug concentration was measured using LC/MS/MS.
(7) Statistical analysis: Regarding plasma concentration transition, an area under a plasma concentration-time curve (AUC was calculated using a non-linear minimum square method program WinNonlin (registered trademark), and bioavailability (BA) was calculated from AUC of an oral-administered group and an intervenous-administered group.

The results can be indicated, for example, as a BA value at oral administration 1 mg/kg in a rat.

Example 22

Formulation Example 1 Tablets

Regarding a medicament component identified by the present invention, tablets consisting of the following composition are produced by the ordinary method.

| | |
|---|---|
| Compound of the present invention | 100 mg |
| Lactose | 60 mg |
| Potato starch | 30 mg |
| Polyvinyl alcohol | 2 mg |
| Magnesium stearate | 1 mg |
| Tar dye | Minor amount |

Example 23

Formulation Example 2 Powders

Regarding a medicament component identified by the present invention, powders consisting of the following composition are produced by the ordinary method.

| Compound of the present invention | 150 mg |
| Lactose | 280 mg |

Example 24

Formulation Example 3 Syrups

Regarding a medicament component identified by the present invention, syrups consisting of the following composition are produced by the ordinary method.

| Compound of the present invention | 100 mg |
| Purified white sugar | 40 g |
| Ethyl p-hydroxybenzoate | 40 mg |
| Propyl p-hydroxybenzoate | 10 mg |
| Chocolate flavor | 0.1 cc |

To this is added water to a total amount of 100 cc.

As described above, the present invention has been exemplified using preferable embodiments of the present invention, but the present invention should not be construed to be limited to the embodiments. It is understood that the scope of the present invention should be construed only by the claims. It is understood that a person skilled in the art can carry out the equivalent range based on the description of the present invention and general technical knowledge from the description of specific preferable embodiments of the present invention. It is understood that a content of patents, patent applications and references cited in the present specification should be incorporated into the present specification by reference as if the content itself is specifically described in the present specification.

The present application also claims the priority based on Japanese Patent Application No. 2009-037939 filed on Feb. 20, 2009, and it is understood that a content of Patent Application No. 2009-037939 should be incorporated into the present specification by reference as if the content is specifically described in the present specification.

INDUSTRIAL APPLICABILITY

The present invention provides a medicament for treating a disease or a disorder associated with neutrophil suppression, a compound used therefor, a pharmaceutically acceptable salt thereof, or a prodrug such as a hydrate thereof. The compound of the present invention exhibits excellent neutrophil suppression activity as described in the present specification. Therefore, the present invention is useful in the pharmaceutical industry.

The invention claimed is:

1. A compound selected from the group consisting of:

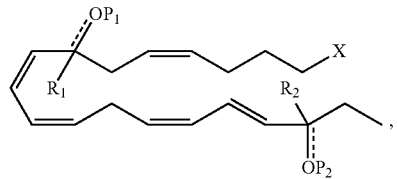

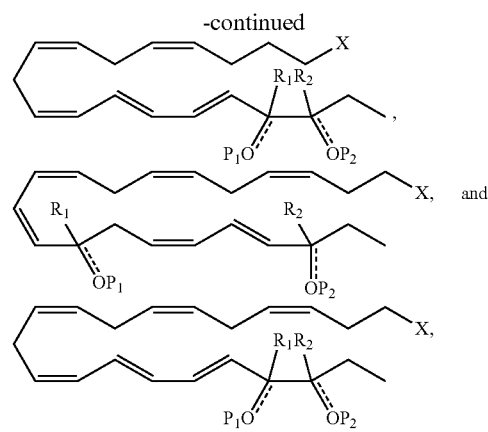

or a pharmaceutically acceptable salt thereof,
wherein,
$P_1$ and $P_2$ are each independently, a hydrogen atom, alkyl, a hydroxyl group or a substituted hydroxyl group, benzyl ether, trityl ether, alkyl ether, tetrahydropyranyl ether, trialkylsilyl ether, glycol ether, or allyl ether, when ===== indicates a single bond, $P_1$, $P_2$, $R_1$ and $R_2$ are not present, when ===== indicates a double bond, and when ===== is a single bond, $R_1$ and $R_2$ are each independently a hydrogen atom, a halogen atom, a substituted or unsubstituted branched or non-branched alkyl group, a substituted or unsubstituted aryl group, a substituted or unsubstituted branched or non-branched alkylaryl group, or a combination thereof;

X is —C(O)O$R_3$, —C(O)N$R_4R_5$, —C(O)H, —C(NH)N$R_4R_5$, —C(S)H, —C(S)O$R_3$, —C(S)N$R_4R_5$, or —CN;

$R_3$ is hydrogen, benzyl ether, trityl ether, alkyl ether, tetrahydropyranyl ether, trialkylsilyl ether, glycol ether, allyl ether, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle or a group of the formula: —N$R_aR_b$, wherein $R_a$ and $R_b$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or $R_a$ and $R_b$ are optionally taken together with an adjacent nitrogen atom to form a substituted or unsubstituted nitrogen-comprising heterocyclic ring;

$R_4$ and $R_5$ are each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocycle, or $R_4$ and $R_5$ are optionally taken together with an adjacent nitrogen atom to form a substituted or unsubstituted nitrogen-comprising heterocyclic ring; and double bond configuration of the compound can be any of cis or trans.

2. The compound, or salt, of claim 1, wherein the compound is selected from the group consisting of:

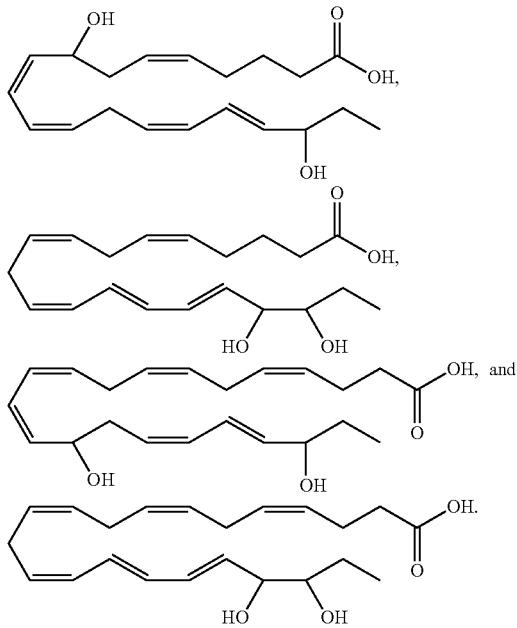

3. A pharmaceutical, comprising the compound, or salt of claim 1.

4. The pharmaceutical of claim 3, adapted for treating at least one disease, disorder, or state which is improved by inhibiting neutrophil selected from the group consisting of a pulmonary disease, an ischemic disease, an inflammatory disease, and a stress related disease.

5. A method of producing the compound, or salt of claim 1, comprising:
   A) contacting eicosapentaenoic acid (EPA), docosahexaenoic acid (DHA), 18-hydroxyl eicosapentaenoic acid (HEPE), or 20-hydroxyl docosahexaenoic acid (HDoHE) with at least one selected from the group consisting of 8-lipoxygenase (8-LOX), 12-lipoxygenase (12-LOX), 12/15-lipoxygenase (12/15-LOX), soybean lipoxygenase (sLOX), and eosinophil, or an extract thereof, to obtain an enzyme metabolite; and
   B) reducing or oxidizing the enzyme metabolite as necessary, optionally introducing a substituent, and optionally separating or purifying an objective compound, or salt thereof.

6. A method of producing the compound, or salt of claim 1, comprising:
   A) contacting eicosapentaenoic acid (EPA), docosahexaenoic acid (DHA), 18-hydroxyl eicosapentaenoic acid (HEPE) or 20-hydroxyl docosahexaenoic acid (HDoHE) with at least one selected from the group consisting of 8-lipoxygenase (8-LOX), 12-lipoxygenase (12-LOX), 12/15-lipoxygenase (12/15-LOX), soybean lipoxygenase (sLOX), and eosinophil, or an extract thereof, to obtain an enzyme metabolite;
   B) contacting the enzyme metabolite obtained in the contacting A), after purification or without purification, with at least one selected from the group consisting of 8-lipoxygenase (8-LOX), 12-lipoxygenase (12-LOX), 12/15-lipoxygenase (12/15-LOX), soybean lipoxygenase (sLOX), and eosinophil, or an extract, thereof to obtain a secondary enzyme metabolite; and
   C) reducing or oxidizing the secondary enzyme metabolite as necessary, optionally introducing a substituent, and optionally separating or purifying the objective compound, or salt thereof.

7. A method of treating an inflammatory disease, comprising administering an effective amount of the compound, or salt of claim 1 to a subject in need of the treating.

8. A method of treating a disease, a disorder, or a state associated with neutrophil, the method comprising administering to a subject in need thereof, an effective amount of the compound, or salt of claim 1.

9. A method of analyzing the compound of claim 1 or a PUFA metabolite, comprising introducing the compound or metabolite onto a liquid chromatograph employing the following liquid chromatography conditions:
   A liquid: water/acetic acid=100/0.1, and B liquid: acetonitrile/methanol=4/1 as a solvent system, with a flow rate: 0 to 30 minutes→50 μL/minute, 30 to 33 minutes→80 μL/minute, 33 to 45 minutes→100 μL/minute, with a solvent gradient of FIG. 1B or an altered system thereof, and parameters described in FIG. 1C.

10. A method of treating a pulmonary disease, comprising administering to a subject in need thereof, an effective amount of the compound or salt claim 1,
   wherein the pulmonary disease is at least one selected from the group consisting of pulmonary distress syndrome, adult respiratory distress syndrome, and chronic obstructive pulmonary disease (COPD).

11. A method of treating an ischemic disease, comprising administering to a subject in need thereof, an effective amount of the compound or salt of claim 1,
   wherein the ischemic disease is at least one selected from the group consisting of ischemic cardiac disease, ischemic renal disease, ischemic brain disease, and ischemic hepatic disease.

12. A method of treating a stress related disease, comprising administering to a subject in need thereof, an effective amount of the compound or salt of claim 1,
   wherein the stress related disease is at least one selected from the group consisting of erosive gastritis, gastric ulcer, duodenal ulcer, bronchial asthma, ulcerative colitis, arteriosclerosis, Crohn disease, malignant tumor, ovarian cyst, salpingitis, hysteromyoma, endometriosis, spontaneous abortion, gestosis, infertility, and dysmenorrhea.

13. The compound, or salt of claim 1, having a structure of

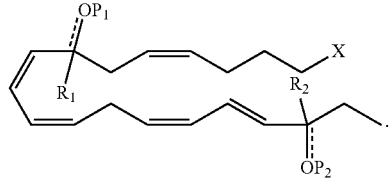

14. The compound, or salt of claim 1, having a structure of

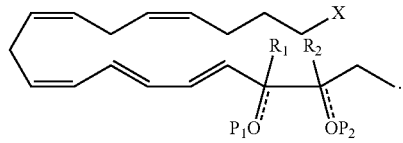

* * * * *